US011001614B2

(12) United States Patent
Kumar et al.

(10) Patent No.: US 11,001,614 B2
(45) Date of Patent: *May 11, 2021

(54) METHOD FOR TREATING A MUSCLE-RELATED DISORDER WITH FOLLISTATIN-RELATED FUSION PROTEINS

(71) Applicant: Acceleron Pharma Inc., Cambridge, MA (US)

(72) Inventors: Ravindra Kumar, Acton, MA (US); Asya Grinberg, Lexington, MA (US); Dianne S. Sako, Medford, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/957,026

(22) Filed: Apr. 19, 2018

(65) Prior Publication Data

US 2018/0305427 A1    Oct. 25, 2018

Related U.S. Application Data

(63) Continuation of application No. 15/081,629, filed on Mar. 25, 2016, now Pat. No. 9,975,934.

(60) Provisional application No. 62/138,886, filed on Mar. 26, 2015.

(51) Int. Cl.
| | |
|---|---|
| *A61K 38/17* | (2006.01) |
| *A61P 21/06* | (2006.01) |
| *A61K 47/68* | (2017.01) |
| *C07K 14/47* | (2006.01) |
| *C07K 19/00* | (2006.01) |
| *A61K 38/00* | (2006.01) |

(52) U.S. Cl.
CPC ...... *C07K 14/4703* (2013.01); *A61K 38/1709* (2013.01); *A61K 47/6811* (2017.08); *A61P 21/06* (2018.01); *C07K 19/00* (2013.01); *A61K 38/00* (2013.01); *C07K 14/4702* (2013.01); *C07K 2319/21* (2013.01); *C07K 2319/30* (2013.01); *C07K 2319/74* (2013.01)

(58) Field of Classification Search
CPC .... C07K 14/47; C07K 14/4703; C07K 19/00; A61K 38/1709
See application file for complete search history.

(56) References Cited

U.S. PATENT DOCUMENTS

| | | |
|---|---|---|
| 5,041,538 A | 8/1991 | Ling et al. |
| 5,182,375 A | 1/1993 | Ling et al. |
| 5,545,616 A | 8/1996 | Woodruff |
| 5,654,404 A | 8/1997 | Roos et al. |
| 6,004,937 A | 12/1999 | Wood et al. |
| 6,599,876 B2 | 7/2003 | Kojima |
| 6,686,198 B1 | 2/2004 | Melton et al. |
| 7,264,968 B2 | 9/2007 | Melton et al. |
| 7,988,973 B2 | 8/2011 | Sherman |
| 8,895,016 B2 | 11/2014 | Sherman et al. |
| 8,895,309 B2 | 11/2014 | Kaspar et al. |
| 8,956,608 B2 | 2/2015 | Walsh et al. |
| 2003/0162714 A1 | 8/2003 | Hill et al. |
| 2004/0209805 A1 | 10/2004 | Phillips et al. |
| 2005/0106154 A1 | 5/2005 | Hill et al. |
| 2005/0260194 A1 | 11/2005 | Peters et al. |
| 2007/0135336 A1 | 6/2007 | De Kretser et al. |
| 2007/0149458 A1 | 6/2007 | Han et al. |
| 2007/0248609 A1 | 10/2007 | De Kretser et al. |
| 2010/0028331 A1 | 2/2010 | Sherman et al. |
| 2010/0028332 A1 | 2/2010 | Sherman et al. |
| 2010/0061997 A1 | 3/2010 | Lee et al. |
| 2010/0286374 A1 | 11/2010 | Kannan et al. |
| 2011/0070233 A1 | 3/2011 | Seehra et al. |
| 2012/0003218 A1 | 1/2012 | Sherman et al. |
| 2012/0149876 A1 | 6/2012 | Von Kreudenstein et al. |
| 2015/0023981 A1 | 1/2015 | De Kretser et al. |
| 2015/0158923 A1 | 6/2015 | Sherman et al. |
| 2015/0183845 A1 | 7/2015 | Sherman et al. |
| 2016/0185836 A1 | 6/2016 | Kumar et al. |
| 2016/0256526 A1 | 9/2016 | Kumar et al. |
| 2016/0311874 A1 | 10/2016 | Kumar et al. |

FOREIGN PATENT DOCUMENTS

| | | |
|---|---|---|
| CN | 1993048 A | 7/2001 |
| CN | 102770458 A | 11/2012 |
| CN | 103387616 A | 11/2013 |
| CN | 103554268 A | 2/2014 |
| CN | 104293834 A | 1/2015 |
| EP | 1 174 149 A1 | 1/2002 |

(Continued)

OTHER PUBLICATIONS

Alignment of human follistatin with EMBOSS Needle performed Oct. 14, 2016 at http://www.ebi.ac.uk!Tools/psa/emboss_needle/).
Bowie, J.U., et al., "Deciphering the Message in Protein Sequences: Tolerance to Amino Acid Substitutions," Science, 257:1306-1310 (1990).
Borgnon et al, "Follistatin Allows Efficient Retroviral-Mediated Gene Transfer into Rat Liver," Biochemical and Biophysical Research Communications 328: pp. 937-943 (2005).
Bork, "Powers and Pitfalls in Sequence Analysis: The 70% Hurdle," Genome Research, 10:398-400 (2000).

(Continued)

*Primary Examiner* — Zachary C Howard
(74) *Attorney, Agent, or Firm* — White & Case LLP

(57) ABSTRACT

In certain aspects, the present disclosure provides compositions and methods for inhibiting activity of TGFβ superfamily ligands, particularly ligands such as GDF8, GDF11, activin A, activin B, activin C and activin E, in vertebrates, including rodents and primates, and particularly in humans. In some embodiments, the compositions of the disclosure may be used to treat or prevent diseases or disorders that are associated with abnormal activity of a follistatin-related polypeptide and/or a follistatin ligand.

28 Claims, 2 Drawing Sheets
(1 of 2 Drawing Sheet(s) Filed in Color)
Specification includes a Sequence Listing.

(56) References Cited

FOREIGN PATENT DOCUMENTS

| WO | WO-92/13947 A1 | 8/1992 |
|---|---|---|
| WO | WO-1994/006456 A1 | 3/1994 |
| WO | WO-1995/10611 A1 | 4/1995 |
| WO | WO-97/15321 A1 | 5/1997 |
| WO | WO-1999/06559 A1 | 2/1999 |
| WO | WO-99/45949 A2 | 9/1999 |
| WO | WO-2001/009368 A1 | 2/2001 |
| WO | WO-2002/10214 A2 | 2/2002 |
| WO | WO-2002/085306 A2 | 10/2002 |
| WO | WO-2003/006057 A1 | 1/2003 |
| WO | WO-03/072714 A2 | 9/2003 |
| WO | WO-2004082710 A1 | 9/2004 |
| WO | WO-2004/108157 A2 | 12/2004 |
| WO | WO-2005/001025 A2 | 1/2005 |
| WO | WO-2006/012627 A2 | 2/2005 |
| WO | WO-2005025601 A1 | 3/2005 |
| WO | WO-2005/033134 A2 | 4/2005 |
| WO | WO-2005032578 A1 | 4/2005 |
| WO | WO-2005100563 A1 | 10/2005 |
| WO | WO-2006/020884 A2 | 2/2006 |
| WO | WO-2006083182 A1 | 8/2006 |
| WO | WO-2007/067616 A2 | 6/2007 |
| WO | WO-2008030367 A2 | 3/2008 |
| WO | WO-2008/060156 A1 | 5/2008 |
| WO | WO-2009/158025 A2 | 12/2009 |
| WO | WO-2009158035 A2 | 12/2009 |
| WO | WO-2012/025536 A1 | 3/2012 |
| WO | WO-2013/151665 A2 | 10/2013 |
| WO | WO-2013/157953 A1 | 10/2013 |
| WO | WO-2013/170315 A1 | 11/2013 |
| WO | WO-2014/003553 A1 | 1/2014 |
| WO | WO-2014/116981 A1 | 7/2014 |
| WO | WO-2014/187807 A1 | 11/2014 |
| WO | WO-2015/187977 A1 | 12/2015 |
| WO | WO-2016/154601 A1 | 9/2016 |

OTHER PUBLICATIONS

Brenner, "Errors in genome annotation," Trends in Genetics, vol. 15(4): 132-133 (1999).

Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 111:2129-2138 (1990).

Cash, et al., "Characterization of Follistatin-Type Domains and Their Contribution to Myostatin and Activin A Antagonism," Mol. Endocrinol. vol. 26(7): 1167-1178 (2012).

Datta-Mannan, A., et al., "An Engineered Human Follistatin Variant: Insights into the Pharmacokinetic and Pharmocodynamic Relationships of a Novel Molecule with Broad Therapeutic Potential" The Journal of Pharmacology and Experimental Therapeutics (2013) 344 (3): 616-623.

Datta-Mannan, et al., "Insights into the Impact of Heterogeneous Glycosylation on the Pharmacokinetic Behavior of Follistatin-Fc-Based Biotherapeutics", Drug Metabolism & Disposition, 43(12), pp. 1882-90 (Dec. 2015).

Doerks et al., "Protein annotation: detective work for function prediction," Trends in Genetics, vol. 14(6): 248-250 (1998).

Foley, et al, "Evaluation of Systemic Follistatin as an Adjuvant to Stimulate Muscle Repair and Improve Motor Function in Pompe Mice," Molecular Therapy, vol. 18, No. 9 pp. 1584-1591 (Sep. 2010).

Gonzalez, et al., "A coreceptor interaction between the CD28 and TNF receptor family members B and T lymphocyte attenuator and herpesvirus entry mediator," Pro Natl Acad Sci USA, 102:1116-1121 (2005).

Guo, et al., "Overexpression of Mouse Follistatin Causes Reproductive Defects in Transgenic Mice," Molecular Endocrinology, vol. 12 No. 1, 11 pages (1998).

Haidet, et al., "Long-term Enhancement of Skeletal Muscle Mass and Strength by Single Gene Administration of Myostatin Inhibitors," PNAS, vol. 105, No. 11, pp. 4318-4322, (Mar. 18, 2008).

Inouye, et al., "Recombinant Expression of Human Follistatin with 315 and 288 Amino Acids: Chemical and Biological Comparison with Native Porcine Follistatin," Endocrinology, vol. 129, No. 2, pp. 815-822, (1991).

International Search Report (PCT/US2016/024368) dated Jun. 7, 2016.

Klein, et al., "Progress in overcoming the chain association issue in bispecific heterodimeric IgG antibodies," mAbs, vol. 4(6): 653-663 (2012).

Kota, et al., "Follistatin Gene Delivery Enhances Muscle Growth and Strength in Nonhuman Primates," Sci Transl Med. 17 pages (Nov. 2009).

Lazar, E., et al., "Transforming Growth Factor a: Mutation of Aspartic Acid 47 and Leucine 48 Results in Different Biological Activities," Molecular and Cellular Biology, 8(3):1247-1252 (1988).

Lin, et al., "Regulation of ovarian functions by the TGF-β superfamily and follistatin," Reproduction, vol. 126: 133-148 (2003).

Miller, et al., "Gene Transfer Demonstrates that Muscle is not a Primary Target for Non-cell-autonomous Toxicity in Familial Amyotrophic Lateral Sclerosis," PNAS, vol. 103, No. 51, pp. 19546-19551 (Dec. 19, 2006).

Nakatani, et al., "Transgenic Expression of a Myostatin Inhibitor Derived from Follistatin Increases Skeletal Muscle Mass and Ameliorates Dystrophic Pathology in mdx Mice," the FASEB Journal, vol. 22, pp. 477-487 (Feb. 2008).

Ngo, J.T., et al., "Computational Complexity, Protein Structure Prediction, and the Levinthal Paradox," The Protein Folding Problem and Tertiary Structure Prediction, Merz et al., eds., Birkhauser, Boston, 433-440 and 492-495 (1994).

Rodino-Klapac, et al., "Inhibition of Myostatin with Emphasis on Follistatin as a Therapy for Muscle Disease," Muscle Nerve, Mar: 39(3) 22 pages (Mar. 2009).

Rose, et al., "Delivery of Recombinant Follistatin Lessens Disease Severity in a Mouse Model of Spinal Muscular Atrophy," Human Molecular Genetics, vol. 18, No. 6, pp. 997-1005 (Dec. 12, 2008).

Sahin, et al., (Encyclopedia of Cancer Jun. 1, 2015; pp. 1-4).

Sidis, et al., "Heparin and Activin-Binding Determinants in Follistatin and FSTL3," Endocrinology, 146(1): pp. 130-136 (Jan. 2005).

Shimasaki, et al., "Primary structure of the human follistatin precursor and its genomic organization," Proc Natl Acad Sci USA, 85:4218-4222 (1988).

Skolnick and Fetrow, "From Genes to protein structure and function: novel applications of computational approaches in the genomic era," Trends in Biotech. vol. 18(1): 34-39 (2000).

Stamler, et al., "The Structure of FSTL3.Actinvin A Complex: Differential Binding of N-Terminal Domains Influences Follistatin-Type Antagonist Specificity," The Journal of Biological Chemistry, vol. 283(47): 32831-32838 (2008).

Sugino, et al., "Molecular Heterogeneity of Follistatin, an Activin-binding Protein," The Journal of Biological Chemistry, vol. 268(21): 15579-15587 (1993).

Supplementary European Search Report EP 16769819 dated Jun. 28, 2018.

Takabe, et al., "AdenovirMediated Overexpression of Follistatin Enlarges Intact Liver of Adult Rats," Hepatology, vol. 38, No. 5 pp. 1107-1115 (2003).

Tilbrook, et al., "Human Recombinant Follistatin-288 Suppresses Plasma Concentrations of Follicle-Stimulating Hormone But is Not a Significant Regulator of Luteinizing Hormone in Castrated Rams," Biology of Reproduction, pp. 1353-1358 (1995).

Trexler, et al., "Distinct Expression Pattern of Two Related Human Proteins Containing Multiple Types of Protease-Inhibitory Modules," Biol. Chem., vol. 383: 223-228 (2002).

Walker, et al., "Alternative Binding Modes Identified for Growth and Differentiation Factor-associated Serum Protein (GASP)-family Antagonism of Myostatin," J. Biol. Chem; Papers in Press: Binding modes for GASP anatagonism of myostatin: pp. 1-23 http://www.jbc.org/cgi/doi/10.1074/jbc.M114.624130 (2015).

Wang, et al., "Analysis of Human Follistatin Structure: Identification of Two Discontinuous N-Terminal Sequences Coding for Activin A Binding and Structural Consequences of Activin Binding to Native Proteins," Endocrinology, vol. 141(9): 3183-3193 (2000).

(56) References Cited

OTHER PUBLICATIONS

Wells, J.A., "Additivity of Mutational Effects in Proteins," Biochemistry, 29(37):8509-8517 (1990).
Yaden, B. C., et al., "Follistatin: A Novel Therapeutic for the Improvement of Muscle Regeneration" The Journal of Pharmacology and Experimental Therapeutics (2014) 349 (2): 355-371.
Ying, "Inhibins, Activins, and Follistatins: Gonadal Proteins Modulating the Secretion of Follicle-Stimulating Hormone," Endocrine Reviews, vol. 9(2): 267-293 (1998).
Zhu, et al., "Follistatin Improves Skeletal Muscle Healing after Injury Disease through an Interaction with Muscle Regeneration, Angiogenesis, and Fibrosis," The American Journal of Pathology, vol. 179, No. 2, pp. 915-930 (Aug. 2011).
Hill et al., "Regulation of Myostatin in Vivo by Growth and Differentiation Factor-Associated Serum Protein-1 A Novel Protein with Protease Inhibitor and Follistatin Domains," Molecular Endocrinology, vol. 17(6): 1144-1154 (2003).
Pearsall et al., "Follistatin-based ligand trap ACE-083 induces localized hypertrophy of skeletal muscle with functional improvement in models of neuromuscular disease," Nature (Scientific Reports); vol. 9:11392 (14 pages (2019).

```
IgG1    --------THTCPPCPAPELLGGPSVFLFPPKPKDTLMISRTPEVTCVVVDVSHEDPEVKF  53
IgG4    ---ESKYGPPCPSCPAPEFLGGPSVFLFPPKPKDTLMISRTPEVTCVVVDVSQEDPEVQF  57
IgG2    --------VECPPCPAPPVAG-PSVFLFPPKPKDTLMISRTPEVTCVVVDVSHEDPEVQF  51
IgG3    EPKSCDTPPPCPRCPAPELLGGPSVFLFPPKPKDTLMISRTPEVTCVVVDVSHEDPEVQF  60
                ** ****  . * ******************************:*****:*

IgG1    NWYVDGVEVHNAKTKPREEQYNSTYRVVSVLTVLHQDWLNGKEYKCKVSNKALPAPIEKT  113
IgG4    NWYVDGVEVHNAKTKPREEQFNSTYRVVSVLTVLHQDWLNGKEYKCKVSNKGLPSSIEKT  117
IgG2    NWYVDGVEVHNAKTKPREEQFNSTFRVVSVLTVVHQDWLNGKEYKCKVSNKGLPAPIEKT  111
IgG3    KWYVDGVEVHNAKTKPREEQYNSTFRVVSVLTVLHQDWLNGKEYKCKVSNKALPAPIEKT  120
        :**************************:***.*******.*****************  **:.****

IgG1    ISKAKGQPREPQVYTLPPSREEMTKNQVSLTCLVKGFYPSDIAVEWESNGQPENNYKTTP  173
IgG4    ISKAKGQPREPQVYTLPPSQEEMTKNQVSLTCLVKGFYPSDIAVEWESNGQPENNYKTTP  177
IgG2    ISKTKGQPREPQVYTLPPSREEMTKNQVSLTCLVKGFYPSDIAVEWESNGQPENNYKTTP  171
IgG3    ISKTKGQPREPQVYTLPPSREEMTKNQVSLTCLVKGFYPSDIAVEWESSGQPENNYNTTP  180
        ***:*************** *************************** .*******:***

IgG1    PVLDSDGSFFLYSKLTVDKSRWQQGNVFSCSVMHEALHNHYTQKSLSLSPGK  225
IgG4    PVLDSDGSFFLYSRLTVDKSRWQEGNVFSCSVMHEALHNHYTQKSLSLSLGK  229
IgG2    PMLDSDGSFFLYSKLTVDKSRWQQGNVFSCSVMHEALHNHYTQKSLSLSPGK  223
IgG3    PMLDSDGSFFLYSKLTVDKSRWQQGNIFSCSVMHEALHNRFTQKSLSLSPGK  232
        *:***********:********* **:***********:.********  **
```

METHOD FOR TREATING A MUSCLE-RELATED DISORDER WITH FOLLISTATIN-RELATED FUSION PROTEINS

RELATED APPLICATIONS

This application is a continuation application of U.S. application Ser. No. 15/081,629, filed Mar. 25, 2016, which claims the benefit of U.S. Provisional Application No. 62/138,886, filed on Mar. 26, 2015 (now expired). The specifications of each of the foregoing applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 18, 2018, is named 1848179-0002-086-102_Seq.txt and is 138,816 bytes in size.

BACKGROUND OF THE INVENTION

The transforming growth factor-β (TGFβ) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. Superfamily members have diverse, often complementary effects. By manipulating the activity of a member of the TGFβ family, it is often possible to cause significant physiological changes in an organism. Changes in muscle, bone, cartilage and other tissues may be achieved by increasing or antagonizing signaling that is mediated by an appropriate TGFβ superfamily member.

Naturally occurring proteins often referred to as ligand traps function as extracellular regulators of TGFβ superfamily ligands. Such ligand traps act either in soluble form or attached to the extracellular matrix and typically sequester ligand by binding to epitopes required for receptor activation. One family of ligand traps includes follistatin and follistatin-related proteins, which possess desirable functional activity based on multiple lines of evidence but have proven difficult to use as therapeutic agents. Thus, there is a need for such agents that function as potent regulators of TGFβ superfamily signaling.

SUMMARY OF THE INVENTION

In part, the disclosure provides heteromeric protein complexes that comprise a follistatin-related fusion protein. Such heteromeric protein complexes optionally exhibit high affinity binding and inhibition of ligands, such as activin A, activin B, activin C, activin E, GDF8, and GDF11, and, optionally, exhibit improved production in recombinant cell lines, improved properties for purification and/or extended serum half-life relative to native forms of follistatin-related proteins.

In certain aspects, protein complexes described herein comprise a first polypeptide covalently or non-covalently associated with a second polypeptide wherein the first polypeptide comprises the amino acid sequence of a follistatin-related polypeptide and the amino acid sequence of a first member of an interaction pair and the second polypeptide comprises the amino acid sequence of a second member of the interaction pair. In other aspects, protein complexes described herein comprise a first polypeptide non-covalently associated with a second polypeptide wherein the first polypeptide comprises the amino acid sequence of a follistatin-related polypeptide and the amino acid sequence of a first member of an interaction pair and the second polypeptide comprises the amino acid sequence of a second member of the interaction pair.

Follistatin-related polypeptides described herein include polypeptides comprising, consisting essentially of, or consisting of an amino acid sequence that is at least 80%, 85%, 90%, 91%, 92%, 93%, 94%, 95%, 96%, 97%, 98%, 99% or 100% to any one of SEQ ID Nos: 1-33. Optionally, the follistatin-related polypeptide is connected directly to the first member of the interaction pair, or an intervening sequence, such as a linker, may be positioned between the amino acid sequence of the follistatin-related polypeptide and the amino acid sequence of the first member of the interaction pair. Examples of linkers include the sequences TGGG (SEQ ID NO: 73), TGGGG (SEQ ID NO: 74), SGGGG (SEQ ID NO: 75), GGGGS (SEQ ID NO: 76), and GGG. Optionally, the first polypeptide may comprise additional amino acids (e.g., 1-50, 1-40, 1-30, 1-20, or 1-10 amino acids) positioned C-terminal and/or N-terminal to the first member of the interaction pair or the follistatin-related polypeptide. Such additional amino acids positioned C-terminal or N-terminal to the first member of the interaction pair or the follistatin-related polypeptide may confer a biological activity. Alternatively, such additional amino acids may confer no, or substantially no, biological activity. Optionally, such additional amino acids are heterologous to the follistatin-related polypeptide and preferably are not a follistatin-related polypeptide.

The second polypeptide may consist essentially of or consist of the second member of the interaction pair. Optionally, the second polypeptide may comprise additional amino acids (e.g., 1-50, 1-40, 1-30, 1-20, or 1-10 amino acids) positioned C-terminal and/or N-terminal to the second member of the interaction pair. Such additional amino acids positioned C-terminal or N-terminal to the second member of the interaction pair may confer a biological activity. Alternatively, such additional amino acids positioned C-terminal or N-terminal to the second member of the interaction pair may confer no, or substantially no, biological activity. Optionally, such additional amino acids positioned C-terminal or N-terminal to the second member of the interaction pair should be heterologous to the follistatin-related polypeptide and preferably are not a follistatin-related polypeptide.

Interaction pairs described herein are designed to promote dimerization or form higher order multimers. In some embodiments, the interaction pair may be any two polypeptide sequences that interact to form a complex, particularly a heterodimeric complex although operative embodiments may also employ an interaction pair that forms a homodimeric complex. The first and second members of the interaction pair may be an asymmetric pair, meaning that the members of the pair preferentially associate with each other rather than self-associating. Accordingly, first and second members of an asymmetric interaction pair may associate to form a heterodimeric complex. Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimeric complex or a heterodimeric complex. Optionally, the first member of the interaction action pair (e.g., an asymmetric pair or an unguided interaction pair) associates covalently with the second member of the interaction pair. Optionally, the first member of the interaction action pair (e.g., an asymmetric pair or an unguided interaction pair) associates non-covalently with the second member of the interaction pair.

Traditional Fc fusion proteins and antibodies are examples of unguided interaction pairs, whereas a variety of engineered Fc domains have been designed as asymmetric interaction pairs. Therefore, a first member and/or a second member an interaction pair described herein may comprise a constant domain of an immunoglobulin, including, for example, the Fc portion of an immunoglobulin. Optionally, a first member of an interaction pair may comprise an amino acid sequence that is derived from an Fc domain of an IgG1, IgG2, IgG3, or IgG4 immunoglobulin of a mammal, preferably a human. For example, the first member of an interaction pair may comprise, consists essentially of, or consist of an amino acid sequence that is at least 80%, 85%, 90%, 91%, 92%, 93%, 94%, 95%, 96%, 97%, 98%, 99% or 100% to any one of SEQ ID Nos: 34-46. Optionally, a second member of an interaction pair may comprise an amino acid sequence that is derived from an Fc domain of an IgG1, IgG2, IgG3, or IgG4. For example, the second member of an interaction pair may comprise, consists essentially of, or consist of an amino acid sequence that is at least 80%, 85%, 90%, 91%, 92%, 93%, 94%, 95%, 96%, 97%, 98%, 99% or 100% to any one of SEQ ID Nos: 34-46. In some embodiments, a first member and a second member of an interaction pair comprise Fc domains derived from the same immunoglobulin class and subtype. In other embodiments, a first member and a second member of an interaction pair comprise Fc domains derived from different immunoglobulin classes or subtypes. Optionally, a first member and/or a second member of an interaction pair (e.g., an asymmetric pair or an unguided interaction pair) comprise a modified constant domain of an immunoglobulin, including, for example, a modified Fc portion of an immunoglobulin. For example, protein complexes of the disclosure may comprise a first modified Fc portion of an IgG comprising an amino acid sequence that is at least 80%, 85%, 90%, 91%, 92%, 93%, 94%, 95%, 96%, 97%, 98%, or 99% identical to an amino acid sequence selected from the group: SEQ ID Nos 34-46 and a second modified Fc portion of an IgG, which may be the same or different from the amino acid sequence of the first modified Fc portion of the IgG, comprising an amino acid sequence that is at least 80%, 85%, 90%, 91%, 92%, 93%, 94%, 95%, 96%, 97%, 98%, or 99% identical to an amino acid sequence selected from the group: SEQ ID Nos 34-46.

In some embodiments, the first member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 39 and, optionally, the second member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 40. In other embodiments, the first member of the interaction pair comprises an amino acid sequence that is at least 80%, 85%, 90%, 91%, 92%, 93%, 94%, 95%, 96%, 9'7%, 98%, 99%, or 100% identical to the amino acid sequence of SEQ ID NO: 40 and, optionally, the second member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 39.

In some embodiments, the first member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 41 and, optionally, the second member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 42. In other embodiments, the first member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 42 and, optionally, the second member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 41.

In some embodiments, the first member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 43 and, optionally, the second member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 44. In other embodiments, the first member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 44 and, optionally, the second member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 43.

In some embodiments, the first member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 45 and, optionally, the second member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 46. In other embodiments, the first member of the interaction pair comprises an amino acid sequence that is at least 80%, 85%, 90%, 91%, 92%, 93%, 94%, 95%, 96%, 9'7%, 98%, 99%, or 100% identical to the amino acid sequence of SEQ ID NO: 46 and, optionally, the second member of the interaction pair comprises an amino acid sequence that is at least 80%, 85%, 90%, 91%, 92%, 93%, 94%, 95%, 96%, 97%, 98%, 99%, or 100% identical to the amino acid sequence of SEQ ID NO: 45.

In some embodiments, the disclosure provides a fusion polypeptide comprising an amino acid sequence of a follistatin-related polypeptide and the amino acid sequence of a member of an asymmetric interaction pair. Such fusion proteins may comprise a follistatin-related polypeptide comprising an amino acid sequence that is at least 80%, 85%, 90%, 95%, 97%, 98%, 99%, or 100% identical to the amino acid sequence of any of SEQ ID Nos: 1-33. Optionally, the fusion polypeptide may comprise a linker polypeptide positioned between the amino acid sequence of the follistatin-related polypeptide and the amino acid sequence of the member of the asymmetric interaction pair. In certain embodiments, the member of the asymmetric interaction pair comprises a constant domain of an immunoglobulin such as an Fc domain of an immunoglobulin. For example, follistatin-related polypeptide fusion proteins of the disclosure may comprise an asymmetric interaction pair that comprises an amino acid sequence that is derived from an Fc domain of an IgG1, IgG2, IgG3 or IgG4. In some embodiments, the asymmetric interaction pair of the fusion protein comprises, consists essentially of, or consists of an amino acid sequence that is at least 80%, 85%, 90%, 95%, 97%, 98%, 99% or 100% identical to any one of SEQ ID NOs: 34-46. In some embodiments, the member of the asymmetric interaction pair of the fusion protein comprises, consists essentially of, or consists of an amino acid sequence that is at least 80%, 85%, 90%, 95%, 97%, 98%, 99% or 100% identical to any one of SEQ ID NOs: 39-46.

Preferably protein complexes of the disclosure bind to one or more ligands selected from the group consisting of: GDF8, GDF-11, activin A, activin B, activin C, or activin E. Optionally, protein complexes of the disclosure bind to one or more of these ligands with a $K_D$ of greater than or equal to $10^{-8}$, $10^{-9}$, $10^{-10}$, $10^{-11}$, or $10^{-12}$. In some embodiments, protein complexes of the disclosure may inhibit signaling (e.g., signaling by SMADs 1, 2, 3, 5, and/or 8) by one or more ligands selected from the group consisting of: GDF8, GDF-11, activin A, activin B, activin C, or activin E. Optionally, protein complexes of the disclosure may inhibit signaling (e.g., signaling by SMADs 1, 2, 3, 5, and/or 8) by one or more of these ligands as measured in a cell-based assay.

Optionally, protein complexes of the disclosure exhibit improved purification compared to native, monomeric follistatin-related peptides. Optionally protein complexes of the disclosure exhibit a serum half-life of at least 4, 6, 12, 24, 36, 48, or 72 hours in a mammal (e.g., a mouse or a human). Optionally, protein complexes of the disclosure may exhibit a serum half-life of at least 6, 8, 10, 12, 14, 20, 25, or 30 days in a mammal (e.g., a mouse or a human).

In certain aspects the disclosure provides nucleic acids encoding any of the first and/or second polypeptides disclosed herein. Nucleic acids disclosed herein may be operably linked to a promoter for expression, and the disclosure further provides cells transformed with such recombinant polynucleotides. Preferably the cell is a mammalian cell such as a COS cell or a CHO cell.

In certain aspects, the disclosure provides methods for making any of the first and second polypeptides disclosed herein as well as protein complexes comprising such a first and second polypeptide of the disclosure. Such a method may include expressing any of the nucleic acids disclosed herein in a suitable cell (e.g., CHO cell or a COS cell). Such a method may comprise: a) culturing a cell under conditions suitable for expression of the first and/or second polypeptide of the disclosure, wherein said cell is transformed with a first and/or second polypeptide expression construct; and b) recovering the first and/or second polypeptide so expressed. Similarly, a method may comprise: a) culturing a cell under conditions suitable for expression of the first and second polypeptide of the disclosure, wherein said cell is transformed with a first and second polypeptide expression construct; and b) recovering the protein complex of the disclosure so expressed. First and/or second polypeptides described herein, as well as protein complex comprising first and second polypeptides of the disclosure, may be recovered as crude, partially purified, or highly purified fractions using any of the well-known techniques for obtaining protein from cell cultures.

Any of the protein complexes described herein may be incorporated into a pharmaceutical preparation. Optionally, such pharmaceutical preparations are at least 80%, 85%, 90%, 95%, 97%, 98% or 99% pure with respect to other polypeptide components. In some embodiments, pharmaceutical preparation described herein comprises less than 20%, 15%, 10%, 5%, 3%, 2%, or 1% of homodimers formed by the self-association of the first or second polypeptides. Optionally, pharmaceutical preparations disclosed herein may comprise one or more additional active agents.

In certain aspects, compositions of the present disclosure, including for example various protein complexes comprising follistatin-related fusion polypeptides disclosed herein, can be used for treating or preventing a disease or condition that is associated with abnormal activity of a follistatin-related fusion polypeptide and/or a follistatin ligand (e.g., myostatin, activins, GDF11). These diseases, disorders or conditions are generally referred to herein as "follistatin-associated conditions." In certain embodiments, the present disclosure provides methods of treating or preventing an individual in need thereof through administering to the individual a therapeutically effective amount of a protein complex described herein. These methods are particularly aimed at therapeutic and prophylactic treatments of animals, and more particularly, humans.

BRIEF DESCRIPTION OF THE DRAWINGS

This patent or patent application filed contains at least one drawing executed in color. Copies of this patent or patent application publication with color drawings(s) will be provided by the Office upon request and payment of the necessary fee.

FIG. 1 shows multiple sequence alignment of Fc domains from human IgG isotypes using Clustal 2.1. Hinge regions are indicated by dotted underline. Double underline indicates examples of positions that may be engineered in IgG1 Fc (SEQ ID NO: 34) to promote asymmetric chain pairing and the corresponding positions with respect to other isotypes (SEQ ID NOs: 38, 35, and 36, respectively, in order of appearance).

DETAILED DESCRIPTION OF THE INVENTION

1. Overview

Figure 2:
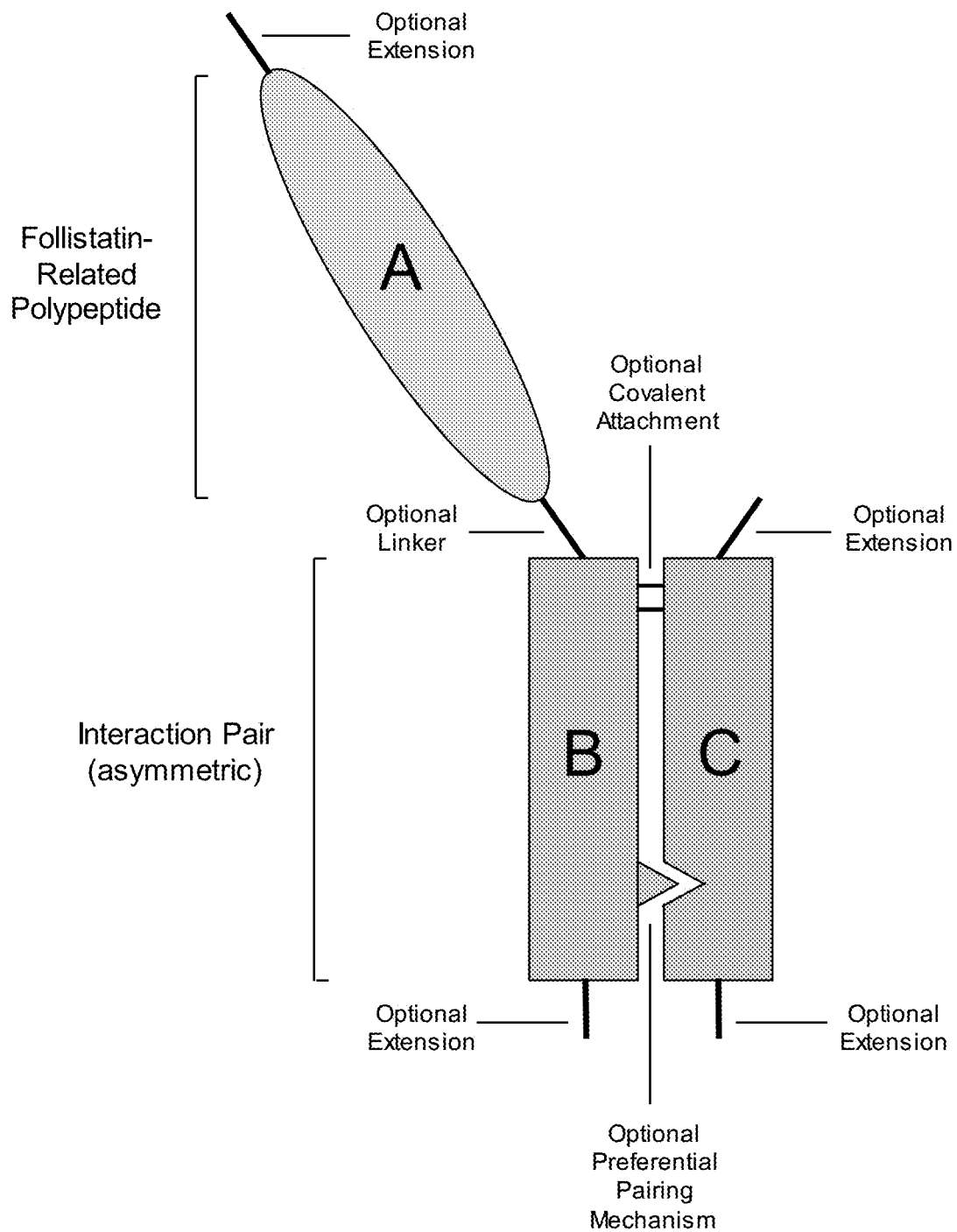
FIG. 2 shows a schematic example of a heteromeric protein complex comprising a follistatin-related polypeptide for therapeutic use. The "follistatin-related polypeptide" (A) may be positioned C-terminal to, or N-terminal to, the "first member of an interaction pair" (B). A linker, as well as other amino acid sequences, may be positioned between the follistatin-related polypeptide and the first member of an interaction pair. The first and second members of the interaction pair (B, C) may be an asymmetric pair, meaning that the members of the pair preferentially associate with each other rather than self-associate, or the interaction pair may be unguided, meaning that the members of the pair may associate with each other or self-associate without substantial preference, and may have the same or different amino acid sequences. Traditional Fc fusion proteins and antibodies are examples of unguided interaction pairs, whereas a variety of engineered Fc domains have been designed as asymmetric interaction pairs. In the second polypeptide, additional amino acids may be positioned C-terminal or N-terminal to the second member of the interaction pair, and such amino acids may or may not confer a biological activity but should be heterologous to the follistatin-related polypeptide and preferably are not a follistatin-related polypeptide.

A. Regulation of Tissue Homeostasis by TGFβ Superfamily Ligands

TGFβ superfamily signaling pathways are critical for prenatal and postnatal regulation of diverse cell types and tissues, including muscle, bone, adipose tissue, pancreatic function, hematopoietic cells, and others. Protein complexes described herein may bind to one or more ligands of the TGFβ superfamily, including for example a member of the activin group, the Growth and Differentiation Factor (GDF) group, the Bone Morphogenetic Protein (BMP) group or one or more other members of the superfamily. The superfamily ligand myostatin, encoded by the MSTN gene and also known as growth differentiation factor-8 (GDF8), is widely recognized as an endogenous inhibitor of skeletal muscle mass. Mice homozygous for a deletion of Mstn display robust increases in skeletal muscle mass due to a combination of increased fiber number and muscle fiber hypertrophy [McPherron et al. (1997) Nature 387:83-90]. Selective postnatal loss of myostatin signaling causes significant muscle fiber hypertrophy, thereby indicating that myostatin is an important regulator of muscle homeostasis in adults [Lee et al. (2010) Mol Endocrinol 24:1998-2008]. Naturally occurring mutations of myostatin are associated with increased skeletal muscle mass in humans, cattle, sheep, and dogs. For example, the Piedmontese and Belgian Blue cattle breeds carry a loss-of-function mutation in MSTN that causes a marked increase in muscle mass [Grobet et al. (1997) Nat Genet 17:71-74]. In humans, inactive alleles of MSTN are associated with increased muscle mass and, reportedly, exceptional strength [Schuelke et al (2004) N Engl J Med 2004, 350:2682-8.] Conversely, muscle wasting in humans associated with infection by human immunodeficiency virus is accompanied by increased MSTN expression [Gonzalez-Cadavid et al. (1998) Proc Natl Acad Sci USA 95:14938-14943].

Inhibition of myostatin activity may be an effective strategy for increasing muscle mass and strength in patients with inherited and acquired clinical conditions associated with debilitating muscle loss [Lee (2004) Annu Rev Cell Dev Biol 20:61-86; Tsuchida (2008) Curr Opin Drug Discov Dev 11:487-494; Rodino-Klapac et al. (2009) Muscle Nerve 39:283-296]. Studies with mouse models of muscle disease have suggested that loss of myostatin signaling has beneficial effects in a wide range of disease settings, including muscular dystrophy, spinal muscular atrophy, cachexia, steroid-induced myopathy, and age-related sarcopenia. Moreover, loss of myostatin signaling has been shown to decrease fat accumulation and improve glucose metabolism in models of metabolic diseases, raising the possibility that targeting myostatin may also have applications for diseases such as obesity and type 2 diabetes. Thus there is considerable interest in identifying methods for therapeutic inhibition of myostatin signaling in vivo.

Like other superfamily ligands, myostatin is synthesized as a precursor consisting of a signal peptide, an N-terminal prodomain, and a C-terminal mature domain. During synthesis, the myostatin prodomain interacts noncovalently with mature myostatin to maintain these molecules in a conformation that facilitates dimerization [Harrison et al (2011) Growth Factors 29:174-186]. After cleavage of the dimeric precursor, the twin prodomains initially remain attached to the mature protein, forming a latent complex [(Miyazono et al (1988) J Biol Chem 263:6407-6415; Wakefield et al (1988) J Biol Chem 263:7646-7654; Brown et al (1990) Growth Factors 3:35-43]. To a greater degree than most TGFβ ligands, secreted myostatin initially exists in a latent or semilatent form whose activity can then be unmasked by other factors [Wolfman et al (2003) Proc Natl Acad Sci USA 100:15842-15846; Szlama et al (2013) FEBS J 280:3822-3839]. Latent myostatin resides in the extracellular space, where the prodomain interacts with matrix proteins to regulate myostatin bioavailability [Anderson et al (2008) J Biol Chem 283:7027-7035; Sengle et al (2011) J Biol Chem 286:5087-5099], or enters the circulation, where the majority of myostatin exists in this latent form [Hill et al (2002) J Biol Chem 277:40735-40741]. In the extracellular compartment, interaction of the myostatin prodomain with the proteoglycan perlecan increases concentrations of the latent complex near target cells. Latent myostatin is converted to an active form by site-specific cleavage of one or both associated prodomains by metalloproteases located in the extracellular matrix [Wolfman et al (2003) Proc Natl Acad Sci USA 100:15842-15846].

Once released from its prodomain, myostatin exerts its cellular effects by inducing formation of ternary complexes incorporating an activin type II receptor (ActRIIA or ActRIIB) and an activin type I receptor (generally ALK4 or ALK7). These activated receptor complexes in turn phosphorylate Smad proteins (Smad2 and Smad3, Smad2/3), which enables the Smad proteins to form a transcriptional complex with Smad4 that regulates expression of specific target genes [see, e.g., Mathews and Vale (1991) Cell 65:973-982; Attisano et al. (1992) Cell 68: 97-108; Massagué (2000) Nat. Rev. Mol. Cell Biol. 1:169-178]. Type I and type II receptors are transmembrane proteins, composed of a ligand-binding extracellular domain with cysteine-rich region, a transmembrane domain, and a cytoplasmic domain with predicted serine/threonine specificity. Type II receptors are required for binding ligands, while type I receptors are essential for signaling.

Although myostatin is the best established case, one or more additional ligands that signal through ActRIIA and/or ActRIIB have also been implicated as endogenous inhibitors of muscle hypertrophy [Lee et al (2005) Proc Natl Acad Sci USA 102:18117-18122]. Activins are a family of dimeric ligands within the TGFβ superfamily and are composed of inhibin-β subunits. Specifically, activins include the homodimeric forms activin A ($\beta_A\beta_A$), activin B ($\beta_B\beta_B$), activin C ($\beta_C\beta_C$), and activin E ($\beta_E\beta_E$), as well as heterodimeric forms, including activin AB ($\beta_A\beta_B$) and heterodimers containing $\beta_C$ or $\beta_E$. In addition, the structurally related heterodimer inhibin is an important inhibitory regulator of activin signaling in various tissues.

Activins play diverse physiologic and pathologic roles. Multiple lines of evidence implicate activins as functioning in concert with myostatin to limit muscle mass, and activin antagonists can promote muscle growth or counteract muscle loss in vivo. [Link et al (1997) Exp Cell Res 233:350-362; He et al (2005) Anat Embryol (Berl) 209:401-407; Souza et al (2008) Mol Endocrinol 22:2689-2702; Gilson et al (2009) Am J Physiol Endocrinol Metab 297: E157-E164; Lee et al (2010) Mol Endocrinol 24:1998-2008; Zhou et al. (2010) Cell 142:531-43]. Activins play a major role in bone homeostasis and are implicated as regulators of erythropoiesis [Maguer-Satta et al (2003) Exp Cell Res 282:110-120; Fields et al (2013) Expert Opin Investig Drugs 22:87-101]. Recent studies have pointed to roles of activins in wound healing, angiogenesis, inflammation, immunity, fibrosis, and cancer [Antsiferova et al (2012) J Cell Sci 125:3929-3937]. The activin/inhibin signaling pathway is associated with cancer of the ovaries, testes, and adrenal glands. In addition, activin A is a major inhibitory regulator of hepatocyte proliferation, and dysregulated activin signaling has been implicated in hepatic diseases including inflammation, fibrosis, liver failure, and cancer. [Kreidl et al (2009) World J Hepatol 1:17-27]. Other functions of activins include induction of mesodermal differentiation, modulation of the cell cycle, support of neuronal cell survival, and coordination of endocrine cell activity [DePaolo et al. (1991) Proc Soc Exp Biol Med 198:500-512; Dyson et al (1997) Curr Biol 7:81-84; Woodruff (1998) Biochem Pharmacol 55:953-963].

As described herein, agents that bind to "activin A" are agents that specifically bind to the $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of a heterodimer complex (e.g., a $\beta_A\beta_B$ heterodimer), agents that bind to "activin A" are specific for epitopes present within the $\beta_A$ subunit, but do not bind to epitopes present within the non-$\beta_A$ subunit of the complex (e.g., the $\beta_B$ subunit of the complex). Similarly, agents disclosed herein that antagonize (inhibit) "activin A" are agents that inhibit one or more activities as mediated by a $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of $\beta_A\beta_B$ heterodimers, agents that inhibit "activin A" are agents that specifically inhibit one or more activities of the $\beta_A$ subunit, but do not inhibit the activity of the non-$\beta_A$ subunit of the complex (e.g., the $\beta_B$ subunit of the complex). This principle applies also to agents that bind to and/or inhibit "activin B", "activin C", and "activin E". Agents disclosed herein that antagonize "activin AB" are agents that inhibit one or more activities as mediated by the $\beta_A$ subunit and one or more activities as mediated by the $\beta_B$ subunit.

Growth differentiation factor-11 (GDF11), also known as bone morphogenetic protein-11 (BMP11), is expressed in the tail bud, limb bud, maxillary and mandibular arches, and dorsal root ganglia during mouse development [see, e.g., Nakashima et al. (1999) Mech. Dev. 80: 185-189]. GDF11 plays a unique role in patterning both mesodermal and neural tissues [see, e.g., Gamer et al. (1999) Dev Biol., 208:222-32] and is a negative regulator of chondrogenesis and myogenesis in developing chick limb [see, e.g., Gamer et al. (2001) Dev Biol. 229:407-20]. Expression of GDF11 in brain suggests that GDF11 may also regulate neural activity, and GDF11 inhibits neurogenesis in the olfactory epithelium [see, e.g., Wu et al. (2003) Neuron. 37:197-207]. Recent studies implicate GDF11 as an important regulatory signal in erythropoiesis, particularly during late-stage erythroid differentiation [Suragani et al (2014) Nat Med 20:408-414]. In addition, GDF11 has been investigated as a potential inhibitor of muscle hypertrophy based on structural similarity to myostatin, shared signaling components, and GDF11 expression in skeletal muscle [McPherron et al. (1999) Nat. Genet. 22: 260-264]. Although GDF11, like myostatin, is detectable in the general circulation in a latent complex with its prodomain and inhibits muscle cell differentiation ex vivo [Souza et al (2008) Mol Endocrinol 22:2689-2702], genetic studies have not revealed a role for GDF11 in regulating muscle size, fiber number, or fiber type, even under conditions of myostatin deficiency [McPherron et al (2009) BMC Devel Biol 9:24]. Thus, it remains to be firmly determined whether GDF11 contributes to the regulation of muscle mass.

B. Extracellular Inhibitors of TGFβ Superfamily Ligands

In addition to the ligand-associated prodomains discussed above, several other native proteins inhibit TGFβ superfamily ligands extracellularly and thereby regulate the activity of these ligands in critical ways. In humans, soluble endogenous inhibitors of myostatin, activins, and GDF11 include multiple follistatin isoforms, the product of the follistatin-like gene (FSTL3) known as FLRG, and a pair of closely related proteins named WFIKKN1 and WFIKKN2 based on their shared domain structure which includes a whey acidic protein domain (W), a follistatin-Kazal domain (F), an immunoglobulin domain (I), two tandem domains related to Kunitz-type protease inhibitor modules (KK), and a netrin domain (N). Follistatin, FLRG, WFIKKN1, and WFIKKN2 polypeptides each contain one or more structural motifs generally referred to as "follistatin domains" which are important for selective binding to TGFβ superfamily ligands. Therefore, as disclosed herein, the term "follistatin-related polypeptides" includes, for example, native follistatin, FLRG, WFIKKN1, and WFIKKN2 sequences, as well as variants and truncations thereof.

Best studied among extracellular inhibitors of myostatin, activins, and/or GDF11 is follistatin, a single gene (FST) from which are generated multiple isoforms. Follistatin is an autocrine glycoprotein expressed in nearly all tissues of higher animals. It was initially isolated from follicular fluid and was identified as a protein fraction that inhibited follicle-stimulating hormone (FSH) secretion from the anterior pituitary [Esch et al. (1987) Mol Endocrinol 1:849-855]. The importance of follistatin in TGFβ superfamily signaling is illustrated by the multiple defects and perinatal death observed in follistatin-deficient mice [Matzuk et al (1995) Nature 374:360-363]. Postnatally, follistatin promotes muscle growth by inhibiting myostatin and activins [Lee et al (2010) Mol Endocrinol 24:1998-2008] and potentially GDF11. The biologic activity of follistatin stems from its ability to bind these ligands with high affinity and thereby prevent interaction of the ligand with its cell-surface receptor—ActRIIA or ActRIIB [Nakamura et al (1990) Science 247:836-838; Kogawa et al (1991) Endocrinology 128: 1434-1440; Schneyer et al (1994) Endocrinology 135:667-674; de Winter et al (1996) Mol Cell Endocrinol 116:105-114; Thompson et al (2005) Dev Cell 9:535-543]. In addition, follistatin contains a heparin-binding domain that in some isoforms facilitates follistatin interaction with proteoglycans at the cell surface [Inouye et al (1992) Mol Cell Endocrinol 90:1-6], thereby maintaining higher concentrations of follistatin near the sites of ligand action. Furthermore, binding of follistatin (FST288) to myostatin substantially increases the affinity of follistatin for heparin [Cash et al (2009) EMBO J 28:2662-2676], thereby suggesting that ligand binding promotes cell-surface localization of the follistatin-myostatin complex.

Follistatin contains three repeats of a distinctive structural motif known as a "follistatin domain", which encompasses a conserved linear pattern of ten cysteines and forms a characteristic arrangement of intramolecular disulfide bonds [Esch et al. (1987) Mol Endocrinol 1:849-855]. A follistatin domain is defined herein as an amino acid domain, or a nucleic acid sequence encoding an amino acid domain, characterized by cysteine-rich repeats. A follistatin domain typically encompasses a span of 65-90 amino acids and contains ten conserved cysteine residues and a region similar to Kazal serine protease inhibitor domains. Thus, follistatin domains are sometimes referred to as "follistatin/Kazal domains" or "follistatin/Kazal-like domains". In general, the loop regions between the cysteine residues exhibit sequence variability, but some conservation is present. The loop between the fourth and fifth cysteines is usually short, containing only one or two amino acids. The amino acids in the loop between the seventh and eighth cysteines are generally the most highly conserved, containing a consensus sequence of (G,A)-(S,N)-(S,N,T)-(D,N)-(G,N) followed by a (T,S)-Y motif. The region between the ninth and tenth cysteines generally contains a motif incorporating two hydrophobic residues (specifically V, I, or L) separated by another amino acid.

The term "follistatin polypeptide" is used to refer to polypeptides comprising any naturally occurring polypeptide of the follistatin family as well as any variants thereof (including mutants, fragments, fusions, and peptidomimetic forms) that retain a useful activity, including, for example, ligand binding (e.g., myostatin, GDF11, activin A, activin B). For example, follistatin polypeptides include polypeptides comprising an amino acid sequence derived from the sequence of any known follistatin having a sequence at least about 80% identical to the sequence of a follistatin polypeptide (SEQ ID NOs: 1-17), and preferably at least 85%, 90%, 95%, 97%, 99% or greater identity to any of SEQ ID NOs: 1-17. The term "follistatin fusion polypeptide" may refer to fusion proteins that comprise any of the polypeptides mentioned above along with a heterologous (non-follistatin) portion. An amino acid sequence is understood to be heterologous to follistatin if it is not uniquely found in the long (315 amino acid) form of human follistatin, represented by SEQ ID NO:3. Many examples of heterologous portions are provided herein, and such heterologous portions may be immediately adjacent, by amino acid sequence, to the follistatin polypeptide portion of a fusion protein, or separated by intervening amino acid sequence, such as a linker or other sequence. In addition, methods for making and testing libraries of polypeptides are described herein and such methods also pertain to making and testing variants of follistatin.

Follistatin is a single-chain polypeptide with a range of molecular weights from 31 to 49 kDa based on alternative mRNA splicing and variable glycosylation of the protein. Alternatively spliced mRNAs from the follistatin gene encode isoforms of 288 amino acids (i.e., FST288) and 315 amino acids (i.e., FST315), and the latter can be processed proteolytically to yield yet another isoform, follistatin 303 (FST303). Analysis of the amino acid sequence of native human follistatin polypeptide has revealed that it comprises five domains: a signal sequence (amino acids 1-29 of SEQ ID NO:1), an N-terminal domain ($FST_{ND}$) (amino acids 30-94 of SEQ ID NO:1), follistatin domain-1 ($FST_{FD1}$) (amino acids 95-164 of SEQ ID NO:1), follistatin domain-2 ($FST_{FD2}$) (amino acids (168-239 of SEQ ID NO:1), and follistatin domain-3 ($FST_{FD3}$) (amino acids 245-316 of SEQ ID NO:1). See Shimanski et al (1988) Proc Natl Acad Sci USA 85:4218-4222.

The human follistatin-288 (FST288) precursor has the following amino acid sequence (SEQ ID NO: 1) (NCBI Reference Sequence NP_006341; Uniprot P19883-2), with the signal peptide indicated by dotted underline, the N-terminal domain ($FST_{ND}$) indicated by dashed underline, and the follistatin domains 1-3 ($FST_{FD1}$, $FST_{FD2}$, $FST_{FD3}$) indicated by solid underline.

```
                                              (SEQ ID NO: 1)
  1 MVRARHQPGG LCLLLLLLCQ FMEDRSAQAG NCWLRQAKNG RCQVLYKTEL

51 SKEECCSTGR LSTSWTEEDV NDNTLFKWMI FNGGAPNCIP CKETCENVDC

101 GPGKKCRMNK KNKPRCVCAP DCSNITWKGP VCGLDGKTYR NECALLKARC

151 KEQPELEVQY QGRCKKTCRD VFCPGSSTCV VDQTNNAYCV TCNRICPEPA

201 SSEQYLCGND GVTYSSACHL RKATCLLGRS IGLAYEGKCI KAKSCEDIQC

251 TGGKKCLWDF KVGRGRCSLC DELCPDSKSD EPVCASDNAT YASECAMKEA

301 ACSSGVLLEV KHSGSCN
```

The mature (processed) human follistatin variant FST288 has the following amino acid sequence (SEQ ID NO: 2) with the N-terminal domain indicated by dashed underline and the follistatin domains 1-3 indicated by solid underline. Moreover, it will be appreciated that any of the initial amino acids G or N, prior to the first cysteine may be removed by processing or intentionally eliminated without any consequence, and polypeptides comprising such slightly smaller polypeptides are further included.

```
                                                   (SEQ ID NO: 2)
  1 GNCWLRQAKN GRCQVLYKTE LSKEECCSTG RLSTSWTEED VNDNTLFKWM

51 IFNGGAPNCI PCKETCENVD CGPGKKCRMN KKNKPRCVCA PDCSNITWKG

101 PVCGLDGKTY RNECALLKAR CKEQPELEVQ YQGRCKKTCR DVFCPGSSTC

151 VVDQTNNAYC VTCNRICPEP ASSEQYLCGN DGVTYSSACH LRKATCLLGR

201 SIGLAYEGKC IKAKSCEDIQ CTGGKKCLWD FKVGRGRCSL CDELCPDSKS

251 DEPVCASDNA TYASECAMKE AACSSGVLLE VKHSGSCN
```

The human follistatin-315 (FST315) precursor has the following amino acid sequence (SEQ ID NO: 3) (NCBI Reference Sequence NP_037541.1; Uniprot P19883), with the signal peptide indicated by dotted underline, the N-terminal domain ($FST_{ND}$) indicated by dashed underline, and the follistatin domains 1-3 ($FST_{FD1}$, $FST_{FD2}$, $FST_{FD3}$) indicated by solid underline.

```
                                                   (SEQ ID NO: 3)
  1 MVRARHQPGG LCLLLLLLCQ FMEDRSAQAG NCWLRQAKNG RCQVLYKTEL

51 SKEECCSTGR LSTSWTEEDV NDNTLFKWMI FNGGAPNCIP CKETCENVDC

101 GPGKKCRMNK KNKPRCVCAP DCSNITWKGP VCGLDGKTYR NECALLKARC

151 KEQPELEVQY QGRCKKTCRD VFCPGSSTCV VDQTNNAYCV TCNRICPEPA

201 SSEQYLCGND GVTYSSACHL RKATCLLGRS IGLAYEGKCI KAKSCEDIQC

251 TGGKKCLWDF KVGRGRCSLC DELCPDSKSD EPVCASDNAT YASECAMKEA

301 ACSSGVLLEV KHSGSCNSIS EDTEEEEEDE DQDYSFPISS ILEW
```

Mature (processed) human FST315 has the following amino acid sequence (SEQ ID NO: 4) with the N-terminal domain indicated by dashed underline and the follistatin domains 1-3 indicated by solid underline. Moreover, it will be appreciated that any of the initial amino acids G or N, prior to the first cysteine may be removed by processing or intentionally eliminated without any consequence, and polypeptides comprising such slightly shorter polypeptides are further included.

```
                                                   (SEQ ID NO: 4)
  1 GNCWLRQAKN GRCQVLYKTE LSKEECCSTG RLSTSWTEED VNDNTLFKWM

51 IFNGGAPNCI PCKETCENVD CGPGKKCRMN KKNKPRCVCA PDCSNITWKG

101 PVCGLDGKTY RNECALLKAR CKEQPELEVQ YQGRCKKTCR DVFCPGSSTC

151 VVDQTNNAYC VTCNRICPEP ASSEQYLCGN DGVTYSSACH LRKATCLLGR
```

```
201 SIGLAYEGKC IKAKSCEDIQ CTGGKKCLWD FKVGRGRCSL CDELCPDSKS

251 DEPVCASDNA TYASECAMKE AACSSGVLLE VKHSGSCNSI SEDTEEEEED

301 EDQDYSFPIS SILEW
```

Follistatin-related polypeptides of the disclosure may include any naturally occurring domain of a follistatin protein as well as variants thereof (e.g., mutants, fragments, and peptidomimetic forms) that retain a useful activity. For example, it is well-known that FST315 and FST288 have high affinity for myostatin, activins (activin A and activin B), and GDF11 and that the follistatin domains (e.g., $FST_{ND}$, $FST_{FD1}$, $FST_{FD2}$, and $FST_{FD3}$) are thought to be involved in the binding of such TGFβ ligands. However, there is evidence that each of these four domains has a different affinity for these TGF-β ligands. For example, a recent study has demonstrated that polypeptide constructs comprising only the N-terminal domain and two $FST_{FD1}$ domains in tandem retained high affinity for myostatin, demonstrated little or no affinity for activins, and promoted systemic muscle growth when introduced into a mouse by gene expression [Nakatani et al (2008) FASEB 22:478-487]. Accordingly, the present disclosure encompasses, in part, variant follistatin proteins that demonstrate selective binding and/or inhibition of a given TGFβ ligand relative to the naturally occurring FST protein (e.g., maintaining high-affinity for myostatin while having a significantly reduced affinity for activin).

In certain aspects, the disclosure includes polypeptides comprising the $FST_{ND}$ domain, as set forth below (SEQ ID NO: 5), and, for example, one or more heterologous polypeptides, and moreover, it will be appreciated that any of the initial amino acids G or N, prior to the first cysteine may be deleted, as in the example shown below (SEQ ID NO: 6).

```
                                               (SEQ ID NO: 5)
 1 GNCWLRQAKN GRCQVLYKTE LSKEECCSTG RLSTSWTEED VNDNTLFKWM

51 IFNGGAPNCI PCKET
```

```
                                               (SEQ ID NO: 6)
 1 CWLRQAKNGR CQVLYKTELS KEECCSTGRL STSWTEEDVN DNTLFKWMIF

51 NGGAPNCIPC KET
```

In certain aspects, the disclosure includes polypeptides comprising the $FST_{FD1}$ domain (SEQ ID NO: 7) which contains the minimal core activities of myostatin (and/or GDF11) binding along with heparin binding as set forth below, and, for example, one or more heterologous polypeptides.

```
                                               (SEQ ID NO: 7)
 1 CENVDCGPGK KCRMNKKNKP RCVCAPDCSN ITWKGPVCGL DGKTYRNECA

51 LLKARCKEQP ELEVQYQGRC
```

In certain aspects, the disclosure includes polypeptides comprising the $FST_{FD2}$ domain (SEQ ID NO: 8) and/or the $FST_{FD3}$ domain (SEQ ID NO: 9) as set forth below, and, for example, one or more heterologous polypeptides.

```
                                               (SEQ ID NO: 8)
 1 CRDVFCPGSS TCVVDQTNNA YCVTCNRICP EPASSEQYLC GNDGVTYSSA

51 CHLRKATCLL GRSIGLAYEG KC
```

```
                                               (SEQ ID NO: 9)
 1 CEDIQCTGGK KCLWDFKVGR GRCSLCDELC PDSKSDEPVC ASDNATYASE

51 CAMKEAACSS GVLLEVKHSG SC
```

An $FST_{FD1}$ sequence may be advantageously maintained in structural context by expression as a polypeptide further comprising the $FST_{ND}$ domain. Accordingly, the disclosure includes polypeptides comprising the $FST_{ND}$-$FST_{FD1}$ sequence, as set forth below (SEQ ID NO:10), and, for example, one or more heterologous polypeptides, and moreover, it will be appreciated that any of the initial amino acids G or N, prior to the first cysteine may be removed by processing or intentionally eliminated without any consequence, and polypeptides comprising such slightly shorter polypeptides are further included.

```
                                                   (SEQ ID NO: 10)
  1 CWLRQAKNGR CQVLYKTELS KEECCSTGRL STSWTEEDVN DNTLFKWMIF

51 NGGAPNCIPC KETCENVDCG PGKKCRMNKK NKPRCVCAPD CSNITWKGPV

101 CGLDGKTYRN ECALLKARCK EQPELEVQYQ GRC
```

As demonstrated by Nakatani et al., a $FST_{ND}$-$FST_{FD1}$-$FST_{FD1}$ construct is sufficient to confer systemic muscle growth when genetically expressed in a mouse, and accordingly the disclosure includes polypeptides comprising the amino acid sequence below (SEQ ID NO: 11) and, for example, one or more heterologous polypeptides.

```
                                                   (SEQ ID NO: 11)
  1 CWLRQAKNGR CQVLYKTELS KEECCSTGRL STSWTEEDVN DNTLFKWMIF

51 NGGAPNCIPC KETCENVDCG PGKKCRMNKK NKPRCVCAPD CSNITWKGPV

101 CGLDGKTYRN ECALLKARCK EQPELEVQYQ GRCCENVDCG PGKKCRMNKK

151 NKPRCVCAPD CSNITWKGPV CGLDGKTYRN ECALLKARCK EQPELEVQYQ

201 GRC
```

While the $FST_{FD1}$ sequence confers myostatin and GDF11 binding, it has been demonstrated that activins, particularly activin A but also activin B, are also negative regulators of muscle, and therefore a follistatin polypeptide that inhibits both the myostatin/GDF11 ligand group and the activin A/activin B ligand group may provide a more potent muscle effect. Given that $FST_{FD2}$ confers activin A and B binding, the disclosure provides polypeptides comprising $FST_{FD1}$-$FST_{FD2}$ (SEQ ID NO: 12) and $FST_{FD1}$-$FST_{FD2}$-$FST_{FD3}$ (SEQ ID NO: 13), as well as constructs comprising $FST_{ND}$-$FST_{FD1}$-$FST_{FD2}$ (SEQ ID NO: 14) and, for example, one or more heterologous polypeptides.

```
                                                   (SEQ ID NO: 12)
  1 CENVDCGPGK KCRMNKKNKP RCVCAPDCSN ITWKGPVCGL DGKTYRNECA

51 LLKARCKEQP ELEVQYQGRC CRDVFCPGSS TCVVDQTNNA YCVTCNRICP

101 EPASSEQYLC GNDGVTYSSA CHLRKATCLL GRSIGLAYEG KC
```

```
                                                   (SEQ ID NO: 13)
  1 CENVDCGPGK KCRMNKKNKP RCVCAPDCSN ITWKGPVCGL DGKTYRNECA

51 LLKARCKEQP ELEVQYQGRC CRDVFCPGSS TCVVDQTNNA YCVTCNRICP

101 EPASSEQYLC GNDGVTYSSA CHLRKATCLL GRSIGLAYEG KCCEDIQCTG

151 GKKCLWDFKV GRGRCSLCDE LCPDSKSDEP VCASDNATYA SECAMKEAAC

201 SSGVLLEVKH SGSC
```

```
                                                   (SEQ ID NO: 14)
  1 CWLRQAKNGR CQVLYKTELS KEECCSTGRL STSWTEEDVN DNTLFKWMIF

51 NGGAPNCIPC KETCENVDCG PGKKCRMNKK NKPRCVCAPD CSNITWKGPV
```

```
101 CGLDGKTYRN ECALLKARCK EQPELEVQYQ GRCCRDVFCP GSSTCVVDQT

151 NNAYCVTCNR ICPEPASSEQ YLCGNDGVTY SSACHLRKAT CLLGRSIGLA

201 YEGKC
```

A follistatin polypeptide of 291 amino acids (representing a truncation of the naturally occurring FST315) may have advantageous properties in certain embodiments. Accordingly, unprocessed (SEQ ID NO: 15) and mature FST291 (SEQ ID NO: 16) polypeptides are included in the disclosure and may be combined with heterologous proteins. Moreover, it will be appreciated that any of the initial amino acids G or N, prior to the first cysteine may be removed by processing or intentionally eliminated without any consequence, and polypeptides comprising such slightly shorter polypeptides are further included, such as the example shown below (SEQ ID NO: 17).

Closely related to the native follistatin isoforms encoded by FSTN is a naturally occurring protein encoded by the FSTL3 gene and known alternatively as follistatin-related gene (FLRG), follistatin-like 3 (FSTL3), or follistatin-related protein (FSRP) [Schneyer et al (2001) Mol Cell Endocrinol 180:33-38]. Like follistatin, FLRG binds to myostatin, activins, and GDF11 with high affinity and thereby inhibits their bioactivity in vivo [Sidis et al (2006) Endocrinology 147:3586-3597]. Unlike follistatin, FLRG does not possess a heparin-binding sequence, cannot bind to cell-surface proteoglycans, and therefore is a less potent inhibitor of activin than is FST288 in the immediate vicinity

```
                                                      (SEQ ID NO: 15)
  1 MVRARHQPGG LCLLLLLLCQ FMEDRSAQAG NCWLRQAKNG RCQVLYKTEL

51 SKEECCSTGR LSTSWTEEDV NDNTLFKWMI FNGGAPNCIP CKETCENVDC

101 GPGKKCRMNK KNKPRCVCAP DCSNITWKGP VCGLDGKTYR NECALLKARC

151 KEQPELEVQY QGRCKKTCRD VFCPGSSTCV VDQTNNAYCV TCNRICPEPA

201 SSEQYLCGND GVTYSSACHL RKATCLLGRS IGLAYEGKCI KAKSCEDIQC

251 TGGKKCLWDF KVGRGRCSLC DELCPDSKSD EPVCASDNAT YASECAMKEA

301 ACSSGVLLEV KHSGSCNSIS (SEQ ID NO: 16)
  1 GNCWLRQAKN GRCQVLYKTE LSKEECCSTG RLSTSWTEED VNDNTLFKWM

51 IFNGGAPNCI PCKETCENVD CGPGKKCRMN KKNKPRCVCA PDCSNITWKG

101 PVCGLDGKTY RNECALLKAR CKEQPELEVQ YQGRCKKTCR DVFCPGSSTC

151 VVDQTNNAYC VTCNRICPEP ASSEQYLCGN DGVTYSSACH LRKATCLLGR

201 SIGLAYEGKC IKAKSCEDIQ CTGGKKCLWD FKVGRGRCSL CDELCPDSKS

251 DEPVCASDNA TYASECAMKE AACSSGVLLE VKHSGSCNSI S (SEQ ID NO: 17)
  1 CWLRQAKNGR CQVLYKTELS KEECCSTGRL STSWTEEDVN DNTLFKWMIF

51 NGGAPNCIPC KETCENVDCG PGKKCRMNKK NKPRCVCAPD CSNITWKGPV

101 CGLDGKTYRN ECALLKARCK EQPELEVQYQ GRCKKTCRDV FCPGSSTCVV

151 DQTNNAYCVT CNRICPEPAS SEQYLCGNDG VTYSSACHLR KATCLLGRSI

201 GLAYEGKCIK AKSCEDIQCT GGKKCLWDFK VGRGRCSLCD ELCPDSKSDE

251 PVCASDNATY ASECAMKEAA CSSGVLLEVK HSGSCNSIS
```

Follistatin proteins herein may be referred to as FST. If followed by a number, such as FST288, this indicates that the protein is the 288-amino-acid isoform of follistatin. If presented as FST288-Fc, this indicates that an Fc domain is fused to the C-terminus of FST288, which may or may not include an intervening linker. The Fc in this instance may be any immunoglobulin Fc portion as that term is defined herein. If presented as FST288-G1Fc, this indicates that the Fc portion of human IgG1 is fused at the C-terminal of FST288. Unless indicated to the contrary, a protein described with this nomenclature will represent a human follistatin protein.

of the cell surface. In contrast to follistatin, FLRG also circulates in the blood bound to mature myostatin, and thus resembles myostatin propeptide in this regard [Hill et al (2002) J Biol Chem 277:40735-40741. Unlike follistatin, FLRG deficiency in mice is not lethal, although it does cause a variety of metabolic phenotypes [Mukherjee et al (2007) Proc Natl Acad Sci USA 104:1348-1353].

The overall structure of FLRG closely resembles that of follistatin. Native human FLRG precursor is a single-chain polypeptide which comprises four domains: a signal sequence (amino acids 1-26 of SEQ ID NO: 18), an N-terminal domain (FLRG$_{ND}$) (amino acids 38-96 of SEQ ID NO: 18), and two follistatin domains referred to herein as FLRG$_{FD1}$ (amino acids 99-167 of SEQ ID NO: 18) and FLRG$_{FD2}$ (amino acids 171-243 of SEQ ID NO: 18).

The term "FLRG polypeptide" is used to refer to polypeptides comprising any naturally occurring polypeptide of FLRG as well as any variants thereof (including mutants, fragments, fusions, and peptidomimetic forms) that retain a useful activity. In certain preferred embodiments, FLRG polypeptides of the disclosure bind to and/or inhibit activity of myostatin, GDF11, or activin, particularly activin A (e.g., ligand-mediated activation of ActRIIA and/or ActRIIB Smad2/3 signaling). Variants of FLRG polypeptides that retain ligand binding properties can be identified using routine methods to assay interactions between FLRG and ligands (see, e.g., U.S. Pat. No. 6,537,966). In addition, methods for making and testing libraries of polypeptides are described herein and such methods also pertain to making and testing variants of FLRG.

For example, FLRG polypeptides include polypeptides comprising an amino acid sequence derived from the sequence of any known FLRG having a sequence at least about 80% identical to the sequence of a FLRG polypeptide (for example, SEQ ID NOs: 18-25), and optionally at least 85%, 90%, 95%, 97%, 99% or greater identity to any of SEQ ID NOs: 18-25. The term "FLRG fusion polypeptide" may refer to fusion proteins that comprise any of the polypeptides mentioned above along with a heterologous (non-FLRG) portion. An amino acid sequence is understood to be heterologous to FLRG if it is not uniquely found in human FLRG, represented by SEQ ID NO: 18. Many examples of heterologous portions are provided herein, and such heterologous portions may be immediately adjacent, by amino acid sequence, to the FLRG polypeptide portion of a fusion protein, or separated by intervening amino acid sequence, such as a linker or other sequence.

The human FLRG precursor has the following amino acid sequence (SEQ ID NO: 18) (amino acids 1-263 of NCBI Reference Sequence NP_005851.1), with the signal peptide indicated by dotted underline, the N-terminal domain (FLRG$_{ND}$) indicated by dashed underline, and the two follistatin domains (FST$_{FD1}$, FST$_{FD2}$) indicated by solid underline.

(SEQ ID NO: 18)

```
  1 MRPGAPGPLW PLPWGALAWA VGFVSSMGSG NPAPGGVCWL QQGQEATCSL

51 VLQTDVTRAE CCASGNIDTA WSNLTHPGNK INLLGFLGLV HCLPCKDSCD

101 GVECGPGKAC RMLGGRPRCE CAPDCSGLPA RLQVCGSDGA TYRDECELRA

151 ARCRGHPDLS VMYRGRCRKS CEHVVCPRPQ SCVVDQTGSA HCVVCRAAPC

201 PVPSSPGQEL CGNNNVTYIS SCHMRQATCF LGRSIGVRHA GSCAGTPEEP

251 PGGESAEEEE NFV
```

Mature (processed) human FLRG comprises the following amino acid sequence (SEQ ID NO: 19) (amino acids 38-263 of NCBI Reference Sequence NP_005851.1) with the N-terminal domain indicated by dashed underline and the two follistatin domains indicated by solid underline. Moreover, it will be appreciated that any of the amino acids (positions 27-37 of SEQ ID NO: 18) prior to the first cysteine (position 38 in SEQ ID NO: 18) may be included without substantial consequence, and polypeptides comprising such slightly longer polypeptides are included.

(SEQ ID NO: 19)

```
  1 CWLQQGQEAT CSLVLQTDVT RAECCASGNI DTAWSNLTHP GNKINLLGFL

51 GLVHCLPCKD SCDGVECGPG KACRMLGGRP RCECAPDCSG LPARLQVCGS

101 DGATYRDECE LRAARCRGHP DLSVMYRGRC RKSCEHVVCP RPQSCVVDQT

151 GSAHCVVCRA APCPVPSSPG QELCGNNNVT YISSCHMRQA TCFLGRSIGV

201 RHAGSCAGTP EEPPGGESAE EEENFV
```

In certain aspects, the disclosure includes polypeptides comprising the $FLRG_{ND}$ domain (SEQ ID NO: 20), which interacts differently with myostatin compared with activin A [Cash et al (2012) J Biol Chem 287:1043-1053], as set forth below, and, for example, one or more heterologous polypeptides. Moreover, it will be appreciated that any of the initial amino acids G or N prior to the first cysteine may be deleted, as in the example shown below (SEQ ID NO: 21).

```
                                           (SEQ ID NO: 20)
  1 GVCWLQQGQE ATCSLVLQTD VTRAECCASG NIDTAWSNLT HPGNKINLLG

51 FLGLVHCLPC
```

```
                                           (SEQ ID NO: 21)
  1 CWLQQGQEAT CSLVLQTDVT RAECCASGNI DTAWSNLTHP GNKINLLGFL

51 GLVHCLPC
```

In certain aspects, the disclosure includes polypeptides comprising the $FLRG_{FD1}$ domain as set forth below (SEQ ID NO: 22), and, for example, one or more heterologous polypeptides.

```
                                           (SEQ ID NO: 22)
  1 CDGVECGPGK ACRMLGGRPR CECAPDCSGL PARLQVCGSD GATYRDECEL

51 RAARCRGHPD LSVMYRGRC
```

In certain aspects, the disclosure includes polypeptides comprising the $FST_{FD2}$ domain as set forth below (SEQ ID NO: 23), and, for example, one or more heterologous polypeptides.

```
                                           (SEQ ID NO: 23)
  1 CEHVVCPRPQ SCVVDQTGSA HCVVCRAAPC PVPSSPGQEL CGNNNVTYIS

51 SCHMRQATCF LGRSIGVRHA GSC
```

A $FLRG_{FD}$ sequence may be advantageously maintained in structural context by expression as a polypeptide further comprising the $FLRG_{ND}$ domain. Accordingly, the disclosure includes polypeptides comprising the $FLRG_{ND}$-$FLRG_{FD1}$ sequence (SEQ ID NO: 24) and the $FLRG_{ND}$-$FLRG_{FD1}$-$FLRG_{FD2}$ sequence (SEQ ID NO: 25), as set forth below, and, for example, one or more heterologous polypeptides. Moreover, it will be appreciated that any of the initial amino acids G or N, prior to the first cysteine may be removed by processing or intentionally eliminated without any consequence, and polypeptides comprising such slightly shorter polypeptides are further included.

```
                                           (SEQ ID NO: 24)
  1 GVCWLQQGQE ATCSLVLQTD VTRAECCASG NIDTAWSNLT HPGNKINLLG

51 FLGLVHCLPC KCDGVECGPG KACRMLGGRP RCECAPDCSG LPARLQVCGS

101 DGATYRDECE LRAARCRGHP DLSVMYRGRC
```

```
                                           (SEQ ID NO: 25)
  1 GVCWLQQGQE ATCSLVLQTD VTRAECCASG NIDTAWSNLT HPGNKINLLG

51 FLGLVHCLPC KCDGVECGPG KACRMLGGRP RCECAPDCSG LPARLQVCGS

101 DGATYRDECE LRAARCRGHP DLSVMYRGRC CEHVVCPRPQ SCVVDQTGSA

151 HCVVCRAAPC PVPSSPGQEL CGNNNVTYIS SCHMRQATCF LGRSIGVRHA

201 GSC
```

If presented as FLRG-Fc, this indicates that an Fc domain is fused to the C-terminus of FLRG, which may or may not include an intervening linker. The Fc in this instance may be any immunoglobulin Fc portion as that term is defined herein. If presented as FLRG-G1Fc, this indicates that the Fc portion of IgG1 is fused at the C-terminus of FLRG. Unless indicated to the contrary, a protein described with this nomenclature will represent a human FLRG protein.

In addition to FSTN and FSTL3, two other genes have been identified whose protein products contain a follistatin domain motif and function as extracellular inhibitors of myostatin and GDF11. In humans, these closely related genes are named WFIKKN1 and WFIKKN2 based on their shared domain structure which includes a whey acidic protein domain, a follistatin-Kazal domain, an immunoglobulin domain, two tandem domains related to Kunitz-type protease inhibitor modules, and a netrin domain [Trexler et al (2001) Proc Natl Acad Sci USA 98:3705-3709; Trexler et al (2002) Biol Chem 383:223-228]. WFIKKN2 is also known as WFIKKN-related protein (WFIKKNRP), and murine counterparts of these proteins are named GDF-associated serum protein-2 (Gasp2) and Gasp1, respectively, based on their ligand-binding ability [Hill et al (2003) Mol Endocrinol 17:1144-1154].

Native WFIKKN1 (GASP2) and WFIKKN2 (GASP1) proteins possess overlapping activity profiles that are nonetheless distinct from each other and from follistatin or FLRG. WFIKKNs bind with high affinity to myostatin, GDF11, and in some cases to myostatin propeptide, with binding to mature ligand mediated primarily by the follistatin domain ($WFIKKN1_{FD}$, $WFIKKN2_{FD}$) and propeptide binding mediated primarily by the netrin domain [Hill et al (2003) Mol Endocrinol 17:1144-1154; Kondas et al (2008) J Biol Chem 283:23677-23684]. In contrast to follistatin and FLRG, neither WFIKKN1 nor WFIKKN2 bind activin [Szlama et al (2010) FEBS J 277:5040-5050]. WFIKKN proteins inhibit myostatin and GDF11 signaling by blocking their access to activin type II receptors [Lee et al (2013) Proc Natl Acad Sci USA 110:E3713-E3722]. Due to the presence of several protease inhibitory modules in both WFIKKNs, it is likely that they also regulate the action of multiple types of proteases. The tissue expression patterns of WFIKKN1 differ prenatally and postnatally from that of WFIKKN2, thus supporting the view that the two proteins serve distinct roles [Trexler et al (2002) Biol Chem 383:223-228].

Additional lines of evidence implicate WFIKKNs in the regulation of skeletal muscle mass. Mice with homozygous deletion of WFIKKN1 or WFIKKN2 display phenotypes consistent with overactivity of myostatin and GDF11, including a reduction in muscle weight, a shift in fiber type from fast glycolytic type IIb fibers to fast oxidative type IIa fibers, and impaired muscle regeneration (Lee et al (2013) Proc Natl Acad Sci USA 110:E3713-E3722]. Conversely, broad overexpression of WFIKKN2 in mice leads mainly to a hypermuscular phenotype [Monestier et al (2012) BMC Genomics 13:541-551. Although both WFIKKN proteins bind to myostatin, WFIKKIN1 and WFIKKN2 may interact differently with myostatin propeptide and thus may differentially block the activation of ActRIIA or ActRIIB by semilatent myostatin, which is the native complex between myotatin and a single myostatin propeptide chain [Szlama et al (2013) FEBS J 280:3822-3839]. Taken together, follistatin-related fusion proteins comprising a WFIKKN1 or WFIKKN2 polypeptide as disclosed herein would be predicted to increase skeletal muscle mass in vivo without causing potentially undesirable effects associated with inhibition of endogenous activins.

The term "WFIKKN1 polypeptide" is used to refer to polypeptides comprising any naturally occurring polypeptide of WFIKKN1 as well as any variants thereof (including mutants, fragments, fusions, and peptidomimetic forms) that retain a useful activity. In certain preferred embodiments, WFIKKN1 polypeptides of the disclosure bind to and/or inhibit activity of myostatin, myostatin propeptide, complexes between myostatin and its propeptide, GDF11, and potentially activins (e.g., ligand-mediated activation of ActRIIA and/or ActRIIB Smad2/3 signaling). Variants of WFIKKN1 polypeptides that retain ligand binding properties can be identified using routine methods to assay interactions between WFIKKN1 and ligands [see, e.g., Kondas et al (2008) J Biol Chem 283:23677-23684; Szlama et al (2013) FEBS J 280:3822-3839]. In addition, methods for making and testing libraries of polypeptides are described herein and such methods also pertain to making and testing variants of WFIKKN1.

For example, WFIKKN1 polypeptides include polypeptides comprising an amino acid sequence derived from the sequence of any known WFIKKN1 polypeptide having a sequence at least about 80% identical to the sequence of a WFIKKN1 polypeptide (for example, SEQ ID NOs: 26-28), and optionally at least 85%, 90%, 95%, 97%, 99% or greater identity to any of SEQ ID NOs: 26-28. The term "WFIKKN1 fusion polypeptide" may refer to fusion proteins that comprise any of the polypeptides mentioned above along with a heterologous (non-WFIKKN1) portion. An amino acid sequence is understood to be heterologous to WFIKKN1 if it is not uniquely found in human WFIKKN1, represented by SEQ ID NO: 26. Many examples of heterologous portions are provided herein, and such heterologous portions may be immediately adjacent, by amino acid sequence, to the WFIKKN1 polypeptide portion of a fusion protein, or separated by intervening amino acid sequence, such as a linker or other sequence.

The human WFIKKN1 precursor has the following amino acid sequence (SEQ ID NO: 26) (NCBI Ref Seq NP_444514.1), with the signal peptide indicated by dotted underline and the follistatin domain ($WFIKKN1_{FD}$) indicated by solid underline.

```
                                                          (SEQ ID NO: 26)
  1 MPALRPLLPL LLLLRLTSGA GLLPGLGSHP GVCPNQLSPN LWVDAQSTCE
    ----------- ----------

51 RECSRDQDCA AAEKCCINVC GLHSCVAARF PGSPAAPTTA ASCEGFVCPQ
                                                   ------

101 QGSDCDIWDG QPVCRCRDRC EKEPSFTCAS DGLTYYNRCY MDAEACLRGL
    ---------- ---------- ---------- ---------- ----------

151 HLHIVPCKHV LSWPPSSPGP PETTARPTPG AAPVPPALYS SPSPQAVQVG
    ----------

201 GTASLHCDVS GRPPPAVTWE KQSHQRENLI MRPDQMYGNV VVTSIGQLVL
```

```
251 YNARPEDAGL  YTCTARNAAG  LLRADFPLSV  VQREPARDAA  PSIPAPAECL

301 PDVQACTGPT  SPHLVLWHYD  PQRGGCMTFP  ARGCDGAARG  FETYEACQQA

351 CARGPGDACV  LPAVQGPCRG  WEPRWAYSPL  LQQCHPFVYG  GCEGNGNNFH

401 SRESCEDACP  VPRTPPCRAC  RLRSKLALSL  CRSDFAIVGR  LTEVLEEPEA

451 AGGIARVALE  DVLKDDKMGL  KFLGTKYLEV  TLSGMDWACP  CPNMTAGDGP

501 LVIMGEVRDG  VAVLDAGSYV  RAASEKRVKK  ILELLEKQAC  ELLNRFQD
```

Mature (processed) human WFIKKN1 has the following amino acid sequence (SEQ ID NO: 27) with the follistatin domain indicated by solid underline. Moreover, it will be appreciated that any of the 13 amino acids prior to the first cysteine may be removed by processing or intentionally eliminated without substantial consequence, and polypeptides comprising such slightly smaller polypeptides are further included.

inhibit activity of myostatin, myostatin propeptide, complexes between myostatin and its propeptide, GDF11, and potentially activins (e.g., ligand-mediated activation of ActRIIA and/or ActRIIB Smad2/3 signaling). Variants of WFIKKN2 polypeptides that retain ligand binding properties can be identified using routine methods to assay interactions between WFIKKN2 and ligands [see, e.g., Kondas et al (2008) J Biol Chem 283:23677-23684; Szlama et al

```
                                                (SEQ ID NO: 27)
  1 AGLLPGLGSH  PGVCPNQLSP  NLWVDAQSTC  ERECSRDQDC  AAAEKCCINV

51 CGLHSCVAAR  FPGSPAAPTT  AASCEGFVCP  QQGSDCDIWD  GQPVCRCRDR

101 CEKEPSFTCA  SDGLTYYNRC  YMDAEACLRG  LHLHIVPCKH  VLSWPPSSPG

151 PPETTARPTP  GAAPVPPALY  SSPSPQAVQV  GGTASLHCDV  SGRPPPAVTW

201 EKQSHQRENL  IMRPDQMYGN  VVVTSIGQLV  LYNARPEDAG  LYTCTARNAA

251 GLLRADFPLS  VVQREPARDA  APSIPAPAEC  LPDVQACTGP  TSPHLVLWHY

301 DPQRGGCMTF  PARGCDGAAR  GFETYEACQQ  ACARGPGDAC  VLPAVQGPCR

351 GWEPRWAYSP  LLQQCHPFVY  GGCEGNGNNF  HSRESCEDAC  PVPRTPPCRA

401 CRLRSKLALS  LCRSDFAIVG  RLTEVLEEPE  AAGGIARVAL  EDVLKDDKMG

451 LKFLGTKYLE  VTLSGMDWAC  PCPNMTAGDG  PLVIMGEVRD  GVAVLDAGSY

501 VRAASEKRVK  KILELLEKQA  CELLNRFQD
```

In certain aspects, the disclosure includes polypeptides comprising the WFIKKN1$_{FD}$ domain as set forth below (SEQ ID NO: 28), and, for example, one or more heterologous polypeptides.

(2013) FEBS J 280:3822-3839]. In addition, methods for making and testing libraries of polypeptides are described herein and such methods also pertain to making and testing variants of WFIKKN2.

```
                                                (SEQ ID NO: 28)
  1 CEGFVCPQQG  SDCDIWDGQP  VCRCRDRCEK  EPSFTCASDG  LTYYNRCYMD

51 AEACLRGLHL  HIVPC
```

If presented as WFIKKN1-Fc, this indicates that an Fc portion is fused to the C-terminus of WFIKKN1, which may or may not include an intervening linker. The Fc in this instance may be any immunoglobulin Fc portion as that term is defined herein. If presented as WFIKKN1-G1Fc, this indicates that the Fc portion of IgG1 is fused at the C-terminus of WFIKKN1. Unless indicated to the contrary, a protein described with this nomenclature will represent a human WFIKKN1 protein.

The term "WFIKKN2 polypeptide" includes polypeptides comprising any naturally occurring polypeptide of WFIKKN2 as well as any variants thereof (including mutants, fragments, fusions, and peptidomimetic forms) that retain a useful activity. In certain preferred embodiments, WFIKKN2 polypeptides of the disclosure bind to and/or For example, WFIKKN2 polypeptides include polypeptides comprising an amino acid sequence derived from the sequence of any known WFIKKN2 polypeptide having a sequence at least about 80% identical to the sequence of a WFIKKN2 polypeptide (for example, SEQ ID NOs: 29-33), and optionally at least 85%, 90%, 95%, 97%, 99% or greater identity to any of SEQ ID NOs: 29-33. The term "WFIKKN2 fusion polypeptide" may refer to fusion proteins that comprise any of the polypeptides mentioned above along with a heterologous (non-WFIKKN2) portion. An amino acid sequence is understood to be heterologous to WFIKKN2 if it is not uniquely found in human WFIKKN2, represented by SEQ ID NO: 29. Many examples of heterologous portions are provided herein, and such heterologous portions may be immediately adjacent, by amino acid sequence, to the WFIKKN2 polypeptide portion of a fusion protein, or separated by intervening amino acid sequence, such as a linker or other sequence.

The human WFIKKN2 precursor has the following amino acid sequence (SEQ ID NO: 29) (NCBI Ref Seq NP_783165.1), with the signal peptide indicated by dotted underline and the follistatin domain (WFIKKN2$_{FD}$) indicated by solid underline.

```
                                                          (SEQ ID NO: 29)
  1 MWAPRCRRFW SRWEQVAALL LLLLLLGVPP RSLALPPIRY SHAGICPNDM

51 NPNLWVDAQS TCRRECETDQ ECETYEKCCP NVCGTKSCVA ARYMDVKGKK

101 GPVGMPKEAT CDHFMCLQQG SECDIWDGQP VCKCKDRCEK EPSFTCASDG

151 LTYYNRCYMD AEACSKGITL AVVTCRYHFT WPNTSPPPPE TTMHPTTASP

201 ETPELDMAAP ALLNNPVHQS VTMGETVSFL CDVVGRPRPE ITWEKQLEDR

251 ENVVMRPNHV RGNVVVTNIA QLVIYNAQLQ DAGIYTCTAR NVAGVLRADF

301 PLSVVRGHQA AATSESSPNG TAFPAAECLK PPDSEDCGEE QTRWHFDAQA

351 NNCLTFTFGH CHRNLNHFET YEACMLACMS GPLAACSLPA LQGPCKAYAP

401 RWAYNSQTGQ CQSFVYGGCE GNGNNFESRE ACEESCPFPR GNQRCRACKP

451 RQKLVTSFCR SDFVILGRVS ELTEEPDSGR ALVTVDEVLK DEKMGLKFLG

501 QEPLEVTLLH VDWACPCPNV TVSEMPLIIM GEVDGGMAML RPDSFVGASS

551 ARRVRKLREV MHKKTCDVLK EFLGLH
```

Mature (processed) human WFIKKN2 has the following amino acid sequence (SEQ ID NO: 30) with the follistatin domain indicated by single underline. Moreover, it will be appreciated that any of the 11 amino acids prior to the first cysteine may be removed by processing or intentionally eliminated without substantial consequence, and polypeptides comprising such slightly smaller polypeptides (SEQ ID NO: 31) are also included.

```
                                                          (SEQ ID NO: 31)
  1 CDHFMCLQQG SECDIWDGQP VCKCKDRCEK EPSFTCASDG LTYYNRCYMD

51 AEACSKGITL AVVTC
```

In certain aspects, the disclosure includes polypeptides comprising the WFIKKN2$_{FD}$ domain as set forth below (SEQ ID NO: 30), and further includes, for example, one or more heterologous polypeptides.

```
 51 TKSCVAARYM DVKGKKGPVG MPKEATCDHF MCLQQGSECD IWDGQPVCKC

101 KDRCEKEPSF TCASDGLTYY NRCYMDAEAC SKGITLAVVT CRYHFTWPNT

151 SPPPPETTMH PTTASPETPE LDMAAPALLN NPVHQSVTMG ETVSFLCDVV

201 GRPRPEITWE KQLEDRENVV MRPNHVRGNV VVTNIAQLVI YNAQLQDAGI

251 YTCTARNVAG VLRADFPLSV VRGHQAAATS ESSPNGTAFP AAECLKPPDS

301 EDCGEEQTRW HFDAQANNCL TFTFGHCHRN LNHFETYEAC MLACMSGPLA

351 ACSLPALQGP CKAYAPRWAY NSQTGQCQSF VYGGCEGNGN NFESREACEE

401 SCPFPRGNQR CRACKPRQKL VTSFCRSDFV ILGRVSELTE EPDSGRALVT

451 VDEVLKDEKM GLKFLGQEPL EVTLLHVDWA CPCPNVTVSE MPLIIMGEVD

501 GGMAMLRPDS FVGASSARRV RKLREVMHKK TCDVLKEFLG LH
```

The murine WFIKKN2 (GASP1) precursor has the following amino acid sequence (SEQ ID NO: 32) (NCBI Ref Seq NP_861540.2), with the signal peptide indicated by dotted underline and the follistatin domain (WFIKKN2$_{FD}$) indicated by solid underline.

```
                                                          (SEQ ID NO: 32)
  1 MCAPGYHRFW FHWGLLLLLL LEAPLRGLAL PPIRYSHAGI CPNDMNPNLW

51 VDAQSTCKRE CETDQECETY EKCCPNVCGT KSCVAARYMD VKGKKGPVGM

101 PKEATCDHFM CLQQGSECDI WDGQPVCKCK DRCEKEPSFT CASDGLTYYN

151 RCFMDAEACS KGITLSVVTC RYHFTWPNTS PPPPETTVHP TTASPETLGL

201 DMAAPALLNH PVHQSVTVGE TVSFLCDVVG RPRPELTWEK QLEDRENVVM

251 RPNHVRGNVV VTNIAQLVIY NVQPQDAGIY TCTARNVAGV LRADFPLSVV

301 RGGQARATSE SSLNGTAFPA TECLKPPDSE DCGEEQTRWH FDAQANNCLT

351 FTFGHCHHNL NHFETYEACM LACMSGPLAI CSLPALQGPC KAYVPRWAYN

401 SQTGLCQSFV YGGCEGNGNN FESREACEES CPFPRGNQHC RACKPRQKLV

451 TSFCRSDFVI LGRVSELTEE QDSGRALVTV DEVLKDEKMG LKFLGREPLE

501 VTLLHVDWTC PCPNVTVGET PLIIMGEVDG GMAMLRPDSF VGASSTRRVR

551 KLREVMYKKT CDVLKDFLGL Q
```

Mature (processed) murine WFIKKN2 has the following amino acid sequence (SEQ ID NO: 33) with the follistatin domain indicated by single underline. Moreover, it will be appreciated that any of the 11 amino acids prior to the first cysteine may be removed by processing or intentionally eliminated without substantial consequence, and polypeptides comprising such slightly smaller polypeptides are further included.

acid sequence of at least one follistatin domain (for example, $FST_{FD1}$, $FST_{FD2}$, $FST_{FD3}$, $FLRG_{FD1}$, $FLRG_{FD2}$, $WFIKKN1_{FD}$, or $WFIKKN2_{FD}$). The term "follistatin-related polypeptide" refers to polypeptides comprising any naturally occurring polypeptide product of the follistatin gene, FLRG (FSTL3, FSRP) gene, WFIKKN1 (GASP2) gene, or WFIKKN2 (GASP1) gene as well as any variants thereof (including mutants, fragments, fusions, and peptido-

```
                                                          (SEQ ID NO: 33)
  1 LPPIRYSHAG ICPNDMNPNL WVDAQSTCKR ECETDQECET YEKCCPNVCG

51 TKSCVAARYM DVKGKKGPVG MPKEATCDHF MCLQQGSECD IWDGQPVCKC

101 KDRCEKEPSF TCASDGLTYY NRCFMDAEAC SKGITLSVVT CRYHFTWPNT

151 SPPPPETTVH PTTASPETLG LDMAAPALLN HPVHQSVTVG ETVSFLCDVV

201 GRPRPELTWE KQLEDRENVV MRPNHVRGNV VVTNIAQLVI YNVQPQDAGI

251 YTCTARNVAG VLRADFPLSV VRGGQARATS ESSLNGTAFP ATECLKPPDS

301 EDCGEEQTRW HFDAQANNCL TFTFGHCHHN LNHFETYEAC MLACMSGPLA

351 ICSLPALQGP CKAYVPRWAY NSQTGLCQSF VYGGCEGNGN NFESREACEE

401 SCPFPRGNQH CRACKPRQKL VTSFCRSDFV ILGRVSELTE EQDSGRALVT

451 VDEVLKDEKM GLKFLGREPL EVTLLHVDWT CPCPNVTVGE TPLIIMGEVD

501 GGMAMLRPDS FVGASSTRRV RKLREVMYKK TCDVLKDFLG LQ
```

If presented as WFIKKN2-Fc, this indicates that an Fc portion is fused to the C-terminus of WFIKKN2, which may or may not include an intervening linker. The Fc in this instance may be any immunoglobulin Fc portion as that term is defined herein. If presented as WFIKKN2-G1Fc, this indicates that the Fc portion of IgG1 is fused at the C-terminus of WFIKKN2. Unless indicated to the contrary, a protein described with this nomenclature will represent a human WFIKKN2 protein.

In certain aspects, the disclosure provides follistatin-related polypeptides and follistatin-related fusion proteins that may inhibit the ligands myostatin, activin A, activin B, and/or GDF11. The term "follistatin-related polypeptide" is used herein to refer to a single polypeptide chain comprising an amino acid sequence that is at least 80%, 85%, 90%, 95%, 96%, 97%, 98%, 995 or 100% identical to the amino mimetic forms) that retain a useful activity, including, for example, ligand binding (e.g., myostatin, GDF11, activin A, activin B). For example, follistatin-related polypeptides include polypeptides comprising an amino acid sequence that is at least about 80%, 85%, 90%, 95%, 97%, 99% or greater identity to SEQ ID NOs: 1-33.

The term "follistatin-related fusion polypeptide" refers to single-chain fusion proteins that comprise a follistatin-related polypeptide mentioned above along with a heterologous portion in a single amino acid sequence. An amino acid sequence is understood to be heterologous to follistatin, FLRG, WFIKKN1, or WFIKKN2 if it is not uniquely found in human FST315, (represented by SEQ ID NO: 3), human FLRG (represented by SEQ ID NO: 18), human WFIKKN1 (represented by SEQ ID NO: 25), or human WFIKKN2 (represented by SEQ ID NO: 28). Many examples of heterologous portions are provided herein, and such heterologous portions may be immediately adjacent, by amino acid sequence, to the follistatin-related polypeptide portion of a fusion protein, or separated by intervening amino acid sequence, such as a linker or other sequence, and may be positioned amino-terminal to or carboxy-terminal to a portion that is a follistatin-related polypeptide.

In certain embodiments, the follistatin-related fusion proteins described herein refer to an asymmetric heterodimeric fusion protein comprising a polypeptide chain derived from a naturally occurring follistatin-related polypeptide. Accordingly, in certain embodiments, the methods of the present disclosure are directed to the use of one or more follistatin-related fusion proteins, including fusion proteins comprising a single-arm follistatin-related polypeptide containing at least one follistatin domain, optionally in combination with one or more supportive therapies, to treat a variety of applicable disorders, particularly disorders that may be addressed by inhibition of the ligands to which such follistatin-related fusion protein binds. For example, a follistatin-related fusion protein that binds to and inhibits myostatin, and optionally other ligands such as GDF11, activin A and/or activin B may be used to increase skeletal muscle mass in a subject in need thereof and/or treat or prevent skeletal muscle loss or a skeletal muscle disorder in a subject in need thereof.

As shown herein, follistatin-related polypeptides may be more amenable to expression as active proteins when expressed in a monomeric form, but such proteins tend to be challenging to purify and also tend to have a short serum residence time (half-life), which are both undesirable in the therapeutic setting. The purification problem may be solved by incorporation of an interaction pair with intrinsic characteristics that facilitate purification, such as properties associated with a constant domain portion (e.g., Fc portion) of an IgG that enable purification of attached proteins by methods already known in the art. A common mechanism for improving serum half-life is to express a polypeptide as a homodimeric fusion protein with a constant domain portion of an IgG. However, follistatin-related polypeptides expressed as homodimeric proteins (e.g. in an Fc fusion construct) may not be as active or well-produced as the monomeric form. As demonstrated herein, the problem may be solved by fusing the monomeric form to a half-life extending moiety, and surprisingly, this can be expeditiously achieved by expressing such proteins as an asymmetric heterodimeric fusion protein in which one member of a binding pair is fused to a follistatin-related polypeptide and another member of the binding pair is fused to no other moiety or a heterologous moiety, resulting in a highly active follistatin-related polypeptide coupled with an improvement in serum half-life conferred by the binding pair.

The numbering of amino acids in the follistatin-related polypeptides is based on the sequence of SEQ ID NOs: 1, 3, 15, 18, 26, 29, or 32, regardless of whether the native leader sequence is used.

The terms used in this specification generally have their ordinary meanings in the art, within the context of this disclosure and in the specific context where each term is used. Certain terms are discussed below or elsewhere in the specification, to provide additional guidance to the practitioner in describing the compositions and methods of the disclosure and how to make and use them. The scope or meaning of any use of a term will be apparent from the specific context in which the term is used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

As used herein "does not substantially bind to X" is intended to mean that an agent has a $K_D$ that is greater than about $10^{-7}$, $10^{-6}$, $10^{-5}$, $10^{-4}$ or greater (e.g., no detectable binding by the assay used to determine the $K_D$) for "X".

2. Follistatin-Related Fusion Polypeptides

In certain aspects, the disclosure concerns follistatin-related fusion polypeptides comprising one or more follistatin domains (e.g., FST-Fc polypeptides, FLRG-Fc polypeptides, WFIKKN1-Fc polypeptides, and WFIKKN2-Fc polypeptides). In certain embodiments, the polypeptides disclosed herein may form protein complexes comprising a first polypeptide covalently or non-covalently associated with a second polypeptide, wherein the first polypeptide comprises the amino acid sequence of a follistatin-related polypeptide and the amino acid sequence of a first member of an interaction pair; and the second polypeptide comprises the amino acid sequence of a second member of the interaction pair, and wherein the second polypeptide does not comprise a follistatin-related polypeptide. The interaction pair may be any two polypeptide sequences that interact to form a complex, particularly a heterodimeric complex although operative embodiments may also employ an interaction pair that forms a homodimeric sequence. As described herein, one member of the interaction pair may be fused to a follistatin-related polypeptide, such as a polypeptide comprising an amino acid sequence that is at least 80%, 85%, 90%, 95%, 97%, 98%, 99% or 100% identical to the sequence of any of SEQ ID NOs: 1-33. Preferably, the interaction pair is selected to confer an improved means of protein purification or an improved serum half-life, or to act as an adapter on to which another moiety, such as a polyethylene glycol moiety, is attached to provide an improved serum half-life relative to the monomeric form of the follistatin-related polypeptide.

As described above, follistatin is characterized by four cysteine-rich regions (i.e., $FST_{ND}$, $FST_{FD1}$, $FST_{FD2}$, and $FST_{FD3}$) that are thought to mediate follistatin ligand binding. Similarly, FLRG is characterized by three cysteine-rich regions (i.e., $FLRG_{ND}$, $FLRG_{FD1}$, and $FLRG_{FD2}$) and WFIKKN1 or WFIKKN2 are each characterized by a cysteine-rich region ($WFIKKN1_{FD}$ or WFIKKN2n) that are thought to mediate binding to myostatin, activins, or GDF11. Furthermore, researchers have demonstrated that polypeptide constructs comprising only one of the three follistatin domains in FST (e.g., $FST_{FD1}$) retains strong affinity towards certain follistatin ligands (e.g., myostatin) and are biologically active in vivo. See Nakatani et al. (2008) FASEB J 22:477-487. Therefore, variant follistatin-related polypeptides of the disclosure may comprise one or more active portions of a follistatin protein. For example, constructs of the disclosure may begin at a residue corresponding to amino acids 30-95 of SEQ ID NO: 1 and end at a position corresponding to amino acids 316-344 of SEQ ID NO: 1. Other examples include constructs that begin at a position from 30-95 of SEQ ID NO: 1 and end at a position corresponding to amino acids 164-167 or 238-244.

The follistatin, FLRG, WFIKKN1, and WFIKKN2 polypeptide variants described herein may be combined in various ways with each other or with heterologous amino acid sequences. For example, variant follistatin-related fusion proteins of the disclosure include polypeptides that comprise one or more follistatin domains selected from $FST_{FD1}$ (amino acids 95-164 of SEQ ID NO: 1; i.e., SEQ ID NO: 7), $FST_{FD2}$ (amino acids 168-239 of SEQ ID NO:1; i.e., SEQ ID NO: 8), or $FST_{FD3}$ (amino acids 245-316 of SEQ ID NO:1; SEQ ID NO: 9) as well as proteins that comprise one or more follistatin domains selected from a sequence at least 80%, 85%, 90%, 92%, 95%, 96%, 97%, 98% or 99% identical to $FST_{FD1}$ (SEQ ID NO: 7), $FST_{FD2}$ (SEQ ID NO: 8), or $FST_{FD3}$ (SEQ ID NO: 9). Similarly, variant follistatin-related fusion proteins of the disclosure include polypeptides that comprise one or more follistatin domains selected from $FLRG_{FD1}$ (amino acids 99-167 of SEQ ID NO: 18; i.e., SEQ ID NO: 22), $FLRG_{FD2}$ (amino acids 171-243 of SEQ ID NO: 18; i.e., SEQ ID NO: 23), $WFIKKN1_{FD}$ (amino acids 93-157 of SEQ ID NO: 26; i.e., SEQ ID NO: 28), or $WFIKKN2_{FD}$ (amino acids 111-175 of SEQ ID NO: 29; i.e., SEQ ID NO: 31) as well as proteins that comprise one or more follistatin domains selected from a sequence at least 80%, 85%, 90%, 92%, 95%, 96%, 97%, 98% or 99% identical to $FST_{FD1}$ (SEQ ID NO: 7), $FST_{FD2}$ (SEQ ID NO: 8), $FST_{FD3}$ (SEQ ID NO: 9), $FLRG_{FD1}$ (SEQ ID NO: 22), $FLRG_{FD2}$ (SEQ ID NO: 23), $WFIKKN1_{FD}$ (SEQ ID NO: 28), or $WFIKKN2_{FD}$ (SEQ ID NO: 31).

These follistatin domains may be combined in any order within a variant follistatin-related polypeptide of the disclosure provided that such recombinant proteins maintain the desired activity including, for example, follistatin ligand-binding activity (e.g., myostatin) and biological activity (e.g., inducing muscle mass and/or muscle strength). Examples of such variant follistatin polypeptides include, for example, polypeptides having domain structures such as $FST_{FD1}$-$FST_{FD2}$-$FST_{FD3}$, $FST_{FD1}$-$FST_{FD3}$, $FST_{FD1}$-$FST_{FD1}$-$FST_{FD3}$, $FST_{FD1}$-$FST_{FD2}$, $FST_{FD1}$-$FST_{FD1}$, $FST_{ND}$-$FST_{FD1}$-$FST_{FD2}$-$FST_{FD3}$, $FST_{ND}$-$FST_{FD1}$-$FST_{FD2}$, $FST_{ND}$-$FST_{FD1}$-$FST_{FD1}$, $FST_{ND}$-$FST_{FD1}$-$FST_{FD3}$, $FST_{ND}$-$FST_{FD1}$-$FST_{FD1}$-$FST_{FD3}$, and polypeptides obtained by fusing other heterologous polypeptides to the N-termini or the C-termini of these polypeptides. Examples of variant follistatin-related polypeptides include, for example, polypeptides having domain structures such as $FLRG_{FD1}$-$FLRG_{FD1}$, $FLRG_{FD1}$-$FLRG_{FD2}$, $FLRG_{FD1}$-$FLRG_{FD1}$-$FLRG_{FD2}$, $FLRG_{ND}$-$FLRG_{FD1}$-$FLRG_{FD1}$, $FLRG_{ND}$-$FST_{FD1}$-$FST_{FD2}$, and polypeptides obtained by fusing other heterologous polypeptides to the N-termini or the C-termini of these polypeptides. These domains may be directly fused or linked via a linker polypeptide. Optionally, polypeptide linkers may be any sequence and may comprise 1-100, 1-50, preferably 1-10, and more preferably 1-5 amino acids. In certain aspects, preferred linkers contain no cysteine amino acids or protease cleavage sites.

In some embodiments, follistatin variants of the disclosure have reduced or abolished binding affinity for one or more follistatin ligands. In certain aspects, the disclosure provides follistatin variants that have reduced or abolished binding affinity for activin. In certain aspects, the disclosure provides follistatin variants that have reduced or abolished binding affinity for activin but retain high affinity for myostatin. In certain aspects, the disclosure provides follistatin variants that have reduced or abolished binding affinity for GDF11 but retain high affinity for myostatin.

In certain embodiments, the present invention relates to antagonizing a ligand of follistatin or another follistatin-related polypeptide, such as an activin, GDF8 or GDF11, with a subject follistatin-related fusion polypeptide. Thus, compositions and methods of the present disclosure are useful for treating disorders associated with abnormal or undesirably high activity of one or more such ligands.

The follistatin related polypeptides of the disclosure may comprise a signal sequence. The signal sequence can be a native signal sequence of a follistatin precursor (e.g., amino acids 1-29 of SEQ ID NO:1), FLRG precursor (e.g., amino acids 1-26 of SEQ ID NO: 18), WFIKKN1 precursor (e.g., amino acids 1-19 of SEQ ID NO: 26), WFIKKN2 precursor (e.g., amino acids 1-34 of SEQ ID NO: 29), or a signal sequence from another protein, such as tissue plasminogen activator (TPA) signal sequence or a honey bee melatin (HBM) signal sequence.

Further N-linked glycosylation sites (N-X-S/T) may be added to a follistatin related polypeptide, and may increase the serum half-life of a follistatin-related fusion protein. N—X-S/T sequences may be generally introduced at positions outside the ligand-binding pocket. N—X-S/T sequences may be introduced into the linker between the follistatin sequence and the Fc or other fusion component. Such a site may be introduced with minimal effort by introducing an N in the correct position with respect to a pre-existing S or T, or by introducing an S or T at a position corresponding to a pre-existing N. Any S that is predicted to be glycosylated may be altered to a T without creating an immunogenic site, because of the protection afforded by the glycosylation. Likewise, any T that is predicted to be glycosylated may be altered to an S. Accordingly, a follistatin-related polypeptide variant may include one or more additional, non-endogenous N-linked glycosylation consensus sequences.

In certain embodiments, the present disclosure contemplates making functional variants by modifying the structure of a follistatin-related polypeptide for such purposes as enhancing therapeutic efficacy, or stability (e.g., ex vivo shelf life and resistance to proteolytic degradation in vivo). Modified follistatin-related polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a follistatin-related polypeptide results in a functional homolog can be readily determined by assessing the ability of the variant follistatin-related polypeptide to produce a response in cells in a fashion similar to the wild-type follistatin-related polypeptide, or to bind to one or more ligands, such as myostatin or activin in a manner similar to wild-type follistatin-related polypeptide.

In certain embodiments, the present invention contemplates specific mutations of the follistatin-related polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type follistatin-related polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a follistatin-related polypeptide is by chemical or enzymatic coupling of glycosides to the follistatin-related polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties may be accomplished chemically and/or enzymatically. Chemical deglycosylation may involve, for example, exposure of the follistatin-related polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on follistatin-related polypeptides can be achieved by the use of a variety of endo- and exo-glycosidases as described by Thotakura et al. (1987) Meth. Enzymol. 138:350. The sequence of a follistatin-related polypeptide may be adjusted, as appropriate, depending on the type of expression system used, as mammalian, yeast, insect and plant cells may all introduce differing glycosylation patterns that can be affected by the amino acid sequence of the peptide. In general, follistatin-related fusion proteins for use in humans will be expressed in a mammalian cell line that provides proper glycosylation, such as HEK293, COS, or CHO cell lines, although other mammalian expression cell lines are expected to be useful as well.

This disclosure further contemplates a method of generating variants, particularly sets of combinatorial variants of a follistatin-related polypeptide, including, optionally, truncation variants; pools of combinatorial mutants are especially useful for identifying functional variant sequences. The purpose of screening such combinatorial libraries may be to generate, for example, follistatin-related polypeptide variants that have altered properties, such as altered pharmacokinetics, or altered ligand binding. A variety of screening assays are provided below, and such assays may be used to evaluate variants. For example, a follistatin-related polypeptide variant may be screened for ability to bind to a ligand such as activin A, B, C or E, GDF8 or GDF11, or to prevent binding of a ligand to a ligand receptor such as ActRIIA or ActRIIB The activity of a follistatin-related polypeptide or its variants may also be tested in a cell-based or in vivo assay. For example, the effect of a follistatin-related polypeptide variant on the expression of genes involved in muscle production may be assessed. This may, as needed, be performed in the presence of one or more recombinant ligand proteins (e.g., myostatin or activin A), and cells may be transfected so as to produce a follistatin-related polypeptide and/or variants thereof, and optionally, a ligand. Likewise, a follistatin-related polypeptide may be administered to a mouse or other animal, and one or more muscle properties, such as muscle mass or strength may be assessed. Such assays are well known and routine in the art. A responsive reporter gene may be used in such cell lines to monitor effects on downstream signaling.

Combinatorially-derived variants can be generated which have a selective potency relative to a naturally occurring follistatin-related polypeptide. Such variant proteins, when expressed from recombinant DNA constructs, can be used in gene therapy protocols. Likewise, mutagenesis can give rise to variants which have intracellular half-lives dramatically different than the corresponding a wild-type follistatin-related polypeptide. For example, the altered protein can be rendered either more stable or less stable to proteolytic degradation or other processes which result in destruction of, or otherwise inactivation of a native follistatin-related polypeptide. Such variants, and the genes which encode them, can be utilized to alter follistatin-related polypeptide levels by modulating the half-life of the follistatin-related polypeptides.

In certain embodiments, the follistatin-related polypeptides of the disclosure may further comprise post-translational modifications in addition to any that are naturally present in the follistatin-related polypeptides. Such modifications include, but are not limited to, acetylation, carboxylation, glycosylation, phosphorylation, lipidation, and acylation. As a result, the follistatin-related polypeptides may contain non-amino acid elements, such as polyethylene glycols, lipids, poly- or mono-saccharide, and phosphates. Effects of such non-amino acid elements on the functionality of a follistatin-related polypeptide may be tested as described herein for other follistatin-related polypeptide variants. When a follistatin-related polypeptide is produced in cells by cleaving a nascent form of the follistatin-related polypeptide, post-translational processing may also be important for correct folding and/or function of the protein. Different cells (such as CHO, COS, HeLa, MDCK, 293, WI38, NIH-3T3 or HEK293) have specific cellular machinery and characteristic mechanisms for such post-translational activities and may be chosen to ensure the correct modification and processing of the follistatin-related polypeptides.

In certain aspects, functional variants or modified forms of the follistatin-related polypeptides include fusion proteins having at least a portion of a follistatin-related polypeptide and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt- conjugated resins are used. Many of such matrices are available in "kit" form, such as the Pharmacia GST purification system and the QIAexpress™ system (Qiagen) useful with (HIS$_6$) fusion partners ("HIS$_6$" disclosed as SEQ ID NO: 77). As another example, a fusion domain may be selected so as to facilitate detection of the follistatin-related polypeptides. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for Factor Xa or thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a follistatin-related polypeptide is fused with a domain that stabilizes the follistatin-related polypeptide in vivo (a "stabilizer" domain). By "stabilizing" is meant anything that increases serum half-life, regardless of whether this is because of reduced degradation, reduced clearance by the kidney, or another pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

As specific examples, the present disclosure provides fusion proteins comprising follistatin-related polypeptides fused to a polypeptide comprising a constant domain of an immunoglobulin, such as a CH1, CH2 or CH3 domain of an immunoglobulin or an Fc. Fc domains derived from human IgG1, IgG2, IgG3, and IgG4 are provided below. Other mutations are known that decrease either CDC or ADCC activity, and collectively, any of these variants are included in the disclosure and may be used as advantageous components of a follistatin fusion protein. Optionally, the IgG1 Fc domain of SEQ ID NO: 34 has one or more mutations at residues such as Asp-265, Lys-322, and Asn-434 (numbered in accordance with the corresponding full-length IgG1). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

An example of a native amino acid sequence that may be used for the Fc portion of human IgG1 (G1Fc) is shown below (SEQ ID NO: 34). Dotted underline indicates the hinge region, and solid underline indicates positions with naturally occurring variants. In part, the disclosure provides polypeptides comprising amino acid sequences with 80%, 85%, 90%, 95%, 96%, 97%, 98%, or 99% identity to SEQ ID NO: 34. Naturally occurring variants in G1Fc would include D134 and L136 according to the numbering system used in SEQ ID NO: 34 (see Uniprot P01857).

```
                                                      (SEQ ID NO: 34)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
```

An example of a native amino acid sequence that may be used for the Fc portion of human IgG2 (G2Fc) is shown below (SEQ ID NO: 35). Dotted underline indicates the hinge region, solid underline indicates positions with naturally occurring variants, and double underline indicates positions where there are data base conflicts in the sequence (according to UniProt P01859). In part, the disclosure provides polypeptides comprising amino acid sequences with 80%, 85%, 90%, 95%, 96%, 97%, 98%, or 99% identity to SEQ ID NO: 35.

```
                                                      (SEQ ID NO: 35)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF FLYSKLTVDK SRWQQGNVFS

201 CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 36) contains a short hinge region consisting of a single 15-residue segment, whereas the second G3Fc sequence (SEQ ID NO: 37) contains a full-length hinge region. In each case, dotted underline indicates the hinge region, and solid underline indicates positions with naturally occurring variants according to UniProt P01859. In part, the disclosure provides polypeptides comprising amino acid sequences with 80%, 85%, 90%, 95%, 96%, 97%, 98%, or 99% identity to SEQ ID NOs: 36, 37.

```
                                                      (SEQ ID NO: 36)
  1 EPKSCDTPPP CPRCPAPELL GGPSVFLFPP KPKDTLMISR TPEVTCVVVD

51 VSHEDPEVQF KWYVDGVEVH NAKTKPREEQ YNSTFRVVSV LTVLHQDWLN

101 GKEYKCKVSN KALPAPIEKT ISKTKGQPRE PQVYTLPPSR EEMTKNQVSL

151 TCLVKGFYPS DIAVEWESSG QPENNYNTTP PMLDSDGSFF LYSKLTVDKS

201 RWQQGNIFSC SVMHEALHNR FTQKSLSLSP GK
```

```
                                                      (SEQ ID NO: 37)
  1 ELKTPLGDTT HTCPRCPEPK SCDTPPPCPR CPEPKSCDTP PPCPRCPEPK

51 SCDTPPPCPR CPAPELLGGP SVFLFPPKPK DTLMISRTPE VTCVVVDVSH

101 EDPEVQFKWY VDGVEVHNAK TKPREEQYNS TFRVVSVLTV LHQDWLNGKE

151 YKCKVSNKAL PAPIEKTISK TKGQPREPQV YTLPPSREEM TKNQVSLTCL
```

```
201 VKGFYPSDIA VEWESSGQPE NNYNTTPPML DSDGSFFLYS KLTVDKSRWQ

251 QGNIFSCSVM HEALHNRFTQ KSLSLSPGK
```

Naturally occurring variants in G3Fc (for example, see Uniprot P01859) include E68Q, V69, P76L, E79Q, Y81F, D97N, N100D, T124A, S169N, S169del, F221Y when converted to the numbering system used in SEQ ID NO: 36, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 38). Dotted underline indicates the hinge region. In part, the disclosure provides polypeptides comprising amino acid sequences with 80%, 85%, 90%, 95%, 96%, 97%, 98%, or 99% identity to SEQ ID NO: 38.

protein that incorporates only two different (asymmetric) heavy chains.

Various methods are known in the art that increase desired pairing of Fc-containing fusion polypeptide chains in a single cell line to produce a preferred asymmetric fusion protein at acceptable yields [see, for example, Klein et al (2012) mAbs 4:653-663]. Methods to obtain desired pairing of Fc-containing chains include, but are not limited to, charge-based pairing (electrostatic steering), "knobs-into-holes" steric pairing, and SEEDbody pairing. See, for example, Ridgway et al (1996) Protein Eng 9:617-621; Merchant et al (1998) Nat Biotech 16:677-681; Davis et al (2010) Protein Eng Des Sel 23:195-202. As demonstrated herein, an asymmetric Fc fusion protein comprising a single WFIKKN2 polypeptide arm, in which charge-based pairing promotes the correct matching of asymmetric polypeptide chains, inhibits myostatin activity in a cell-based reporter gene assay with substantially greater potency (lower $IC_{50}$) than a symmetric Fc fusion protein comprising dual WFIKKN2 polypeptide arms.

In certain embodiments, the disclosure provides desired pairing of asymmetric Fc-containing polypeptide chains using Fc sequences engineered to be complementary on the basis of charge pairing (electrostatic steering). One of a pair

```
                                                        (SEQ ID NO: 38)
  1 ESKYGPPCPS CPAPELLGGP SVFLFPPKPK DTLMISRTPE VTCVVVDVSQ

51 EDPEVQFNWY VDGVEVHNAK TKPREEQFNS TYRVVSVLTV LHQDWLNGKE

101 YKCKVSNKGL PSSIEKTISK AKGQPREPQV YTLPPSQEEM TKNQVSLTCL

151 VKGFYPSDIA VEWESNGQPE NNYKTTPPVL DSDGSFFLYS RLTVDKSRWQ

201 EGNVFSCSVM HEALHNHYTQ KSLSLSLGK
```

A variety of engineered mutations in the Fc domain are presented herein with respect to the G1Fc sequence (SEQ ID NO: 34), and analogous mutations in G2Fc, G3Fc, and G4Fc can be derived from their alignment with G1Fc in FIG. 1. Due to unequal hinge lengths, analogous Fc positions based on isotype alignment (FIG. 1) possess different amino acid numbers in SEQ ID NOs: 34, 35, 36, and 38.

A problem that arises in large-scale production of asymmetric immunoglobulin-based proteins from a single cell line is known as the "chain association issue". As confronted prominently in the production of bispecific antibodies, the chain association issue concerns the challenge of efficiently producing a desired multichain protein from among the multiple combinations that inherently result when different heavy chains and/or light chains are produced in a single cell line [see, for example, Klein et al (2012) mAbs 4:653-663]. This problem is most acute when two different heavy chains and two different light chains are produced in the same cell, in which case there are a total of 16 possible chain combinations (although some of these are identical) when only one is typically desired. Nevertheless, the same principle accounts for diminished yield of a desired multichain fusion protein that incorporates only two different (asymmetric) heavy chains.

of Fc sequences with electrostatic complementarity can be arbitrarily fused to the follistatin-related polypeptide (e.g., follistatin polypeptide, FLRG polypeptide, WFIKKN1 polypeptide, or WFIKKN2 polypeptide) of the construct, with or without an optional linker, to generate a follistatin-related fusion polypeptide. This single chain can be coexpressed in a cell of choice along with the Fc sequence complementary to the first Fc to favor generation of the desired multichain construct (a follistatin-related fusion protein). In this example based on electrostatic steering, SEQ ID NO: 39 [human G1Fc(E134K/D177K)] and SEQ ID NO: 40 [human G1Fc(K170D/K187D)] are examples of complementary Fc sequences in which the engineered amino acid substitutions are double underlined, and the follistatin-related polypeptide of the construct can be fused to either SEQ ID NO: 39 or SEQ ID NO: 40, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 1) will generate complementary Fc pairs which may be used instead of the complementary hG1Fc pair below (SEQ ID NOs: 39, 40).

```
                                                  (SEQ ID NO: 39)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSRKEMTKNQ VSLTCLVKGF

151 YPSDIAVEWE SNGQPENNYK TTPPVLKSDG SFFLYSKLTV DKSRWQQGNV

201 FSCSVMHEAL HNHYTQKSLS LSPGK (SEQ ID NO: 40)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYD TTPPVLDSDG SFFLYSDLTV DKSRWQQGNV

201 FSCSVMHEAL HNHYTQKSLS LSPGK
```

In part, the disclosure provides desired pairing of asymmetric Fc-containing polypeptide chains using Fc sequences engineered for steric complementarity. In part, the disclosure provides knobs-into-holes pairing as an example of steric complementarity. One of a pair of Fc sequences with steric complementarity can be arbitrarily fused to the follistatin-related polypeptide (e.g., follistatin polypeptide, FLRG polypeptide, WFIKKN1 polypeptide, or WFIKKN2 polypeptide) of the construct, with or without an optional linker, to generate a follistatin-related fusion polypeptide. This single chain can be coexpressed in a cell of choice along with the Fc sequence complementary to the first Fc to favor generation of the desired multichain construct. In this example based on knobs-into-holes pairing, SEQ ID NO: 41 [human G1Fc(T144Y)] and SEQ ID NO: 42 [human G1Fc (Y185T)] are examples of complementary Fc sequences in which the engineered amino acid substitutions are double underlined, and the follistatin-related polypeptide of the construct can be fused to either SEQ ID NO: 41 or SEQ ID NO: 42, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 1) will generate complementary Fc pairs which may be used instead of the complementary hG1Fc pair below (SEQ ID NOs: 41, 42).

```
                                                  (SEQ ID NO: 41)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLYCLVKGF

151 YPSDIAVEWE SNGQPENNYK TTPPVLDSDG SFFLYSKLTV DKSRWQQGNV

201 FSCSVMHEAL HNHYTQKSLS LSPGK (SEQ ID NO: 42)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLTSKLTV DKSRWQQGNV

201 FSCSVMHEAL HNHYTQKSLS LSPGK
```

An example of Fc complementarity based on knobs-into-holes pairing combined with an engineered disulfide bond is disclosed in SEQ ID NO: 43 [hG1Fc(S132C/T144W)] and SEQ ID NO: 44 [hG1Fc(Y127C/T144S/L146A/Y185V)]. The engineered amino acid substitutions in these sequences are double underlined, and the follistatin-related polypeptide of the construct can be fused to either SEQ ID NO: 43 or SEQ ID NO: 44, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 1) will generate complementary Fc pairs which may be used instead of the complementary hG1Fc pair below (SEQ ID NOs: 43, 44).

```
                                                          (SEQ ID NO: 43)
    1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PCREEMTKNQ VSLWCLVKGF

151 YPSDIAVEWE SNGQPENNYK TTPPVLDSDG SFFLYSKLTV DKSRWQQGNV

201 FSCSVMHEAL HNHYTQKSLS LSPGK (SEQ ID NO: 44)
    1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVCTLP PSREEMTKNQ VSLSCAVKGF

151 YPSDIAVEWE SNGQPENNYK TTPPVLDSDG SFFLVSKLTV DKSRWQQGNV

201 FSCSVMHEAL HNHYTQKSLS LSPGK
```

In part, the disclosure provides desired pairing of asymmetric Fc-containing polypeptide chains using Fc sequences engineered to generate interdigitating β-strand segments of human IgG and IgA CH3 domains. Such methods include the use of strand-exchange engineered domain (SEED) CH3 heterodimers allowing the formation of SEEDbody fusion proteins [see, for example, Davis et al (2010) Protein Eng Design Sel 23:195-202]. One of a pair of Fc sequences with SEEDbody complementarity can be arbitrarily fused to the follistatin-related polypeptide (e.g., follistatin polypeptide, FLRG polypeptide, WFIKKN1 polypeptide, or WFIKKN2 polypeptide) of the construct, with or without an optional linker, to generate a follistatin-related fusion polypeptide. This single chain can be coexpressed in a cell of choice along with the Fc sequence complementary to the first Fc to favor generation of the desired multichain construct. In this example based on SEEDbody (Sb) pairing, SEQ ID NO: 45 [hG1Fc(SbAG)] and SEQ ID NO: 46 [hG1Fc(SbGA)] are examples of complementary IgG Fc sequences in which the engineered amino acid substitutions from IgA Fc are double underlined, and the follistatin-related polypeptide of the construct can be fused to either SEQ ID NO: 45 or SEQ ID NO: 46, but not both. Given the high degree of amino acid sequence identity between native hG1Fc, native hG2Fc, native hG3Fc, and native hG4Fc, it can be appreciated that amino acid substitutions at corresponding positions in hG1Fc, hG2Fc, hG3Fc, or hG4Fc (see FIG. 1) will generate an Fc monomer which may be used in the complementary IgG-IgA pair below (SEQ ID NOs: 45, 46).

```
                                                          (SEQ ID NO: 45)
    1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PFRPEVHLLP PSREEMTKNQ VSLTCLARGF

151 YPKDIAVEWE SNGQPENNYK TTPSRQEPSQ GTTTFAVTSK LTVDKSRWQQ

201 GNVFSCSVMH EALHNHYTQK TISLSPGK (SEQ ID NO: 46)
    1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PPSEELALNE LVTLTCLVKG

151 FYPSDIAVEW ESNGQELPRE KYLTWAPVLD SDGSFFLYSI LRVAAEDWKK

201 GDTFSCSVMH EALHNHYTQK SLDRSPGK
```

It is understood that different elements of the fusion proteins may be arranged in any manner that is consistent with the desired functionality. For example, a follistatin-related polypeptide may be placed C-terminal to a heterologous domain, or, alternatively, a heterologous domain may be placed C-terminal to a follistatin-related polypeptide. The follistatin-related polypeptide domain and the heterologous domain need not be adjacent in a fusion protein, and additional domains or amino acid sequences may be included C- or N-terminal to either domain or between the domains.

As used herein, the term "immunoglobulin Fc domain" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. It is also understood that a follistatin polypeptide may comprise only a domain of an immunoglobulin, such as a CH1 domain, a CH2 domain or a CH3 domain. Many of these domains confer desirable pharmacokinetic properties as well as dimerization or higher order multimerization.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087 and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a CH3 domain of Fc gamma or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613). Additionally, in many instances, the C-terminal lysine, or K, will be removed and thus any of the polypeptides described herein may omit the C-terminal K that is found in an Fc domain, such as those shown in SEQ ID NOs: 34-46.

In certain embodiments, the follistatin-related polypeptides of the present disclosure contain one or more modifications that are capable of stabilizing the follistatin-related polypeptides. For example, such modifications enhance the in vitro half-life of the follistatin-related polypeptides, enhance circulatory half-life of the follistatin-related polypeptides or reducing proteolytic degradation of the follistatin-related polypeptides. Such stabilizing modifications include, but are not limited to, fusion proteins (including, for example, fusion proteins comprising a follistatin-related polypeptide and a stabilizer domain), modifications of a glycosylation site (including, for example, addition of a glycosylation site to a follistatin-related polypeptide), and modifications of carbohydrate moiety (including, for example, removal of carbohydrate moieties from a follistatin-related polypeptide). In the case of fusion proteins, a follistatin-related polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the follistatin-related polypeptides, which are isolated from, or otherwise substantially free of, other proteins. In certain embodiments, the present invention facilitates purification of therapeutically active follistatin-related polypeptides by attachment of an interaction pair (for example, an Fc domain) possessing properties advantageous for purification.

In certain embodiments, follistatin-related polypeptides (unmodified or modified) of the disclosure can be produced by a variety of art-known techniques. For example, such follistatin-related polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the follistatin-related polypeptides, fragments or variants thereof may be recombinantly produced using various expression systems (e.g., E. coli, Chinese Hamster Ovary cells, COS cells, baculovirus) as is well known in the art (also see below). In a further embodiment, the modified or unmodified follistatin-related polypeptides may be produced by digestion of naturally occurring or recombinantly produced full-length follistatin-related polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such follistatin-related polypeptides may be produced from naturally occurring or recombinantly produced full-length follistatin-related polypeptides such as standard techniques known in the art, such as by chemical cleavage (e.g., cyanogen bromide, hydroxylamine).

Any of the follistatin-related polypeptides disclosed herein may be combined with one or more additional follistatin-related polypeptides of the disclosure to achieve a desired effect such as treating a follistatin-related disorder (e.g., increase muscle mass and/or strength in a subject in need thereof, treat or prevent muscle loss in a subject in need thereof, treat or prevent one or more complications of muscle loss in a subject in need thereof; increase hemoglobin concentration or red blood cell count in a subject in need thereof, treat or prevent inadequate hemoglobin concentration or red blood cell count in a subject in need thereof, treat or prevent one or more complications of inadequate hemoglobin concentration or red blood cell count in a subject in need thereof; increase bone mass and/or strength in a subject in need thereof, treat or prevent bone loss or fragility in a subject in need thereof, treat or prevent one or more complications of bone loss or fragility in a subject in need thereof; or treat cancer in a subject in need thereof). For example, a follistatin polypeptide disclosed herein can be used in combination with i) one or more additional FLRG polypeptides disclosed herein, ii) one or more WFIKKN1 polypeptides disclosed herein, and/or iii) one or more WFIKKN2 polypeptides disclosed herein.

3. Nucleic Acids Encoding Follistatin-Related Polypeptides

In certain aspects, the invention provides isolated and/or recombinant nucleic acids encoding any of the follistatin-related polypeptides disclosed herein. The subject nucleic acids may be single stranded or double stranded. Such nucleic acids may be DNA or RNA molecules. These nucleic acids are may be used, for example, in methods for making follistatin-related polypeptides.

For example, the following sequence encodes a naturally occurring human follistatin precursor polypeptide (SEQ ID NO: 47) (nucleotides 359-1390 of NCBI Reference Sequence: NM_013409.2):

(SEQ ID NO: 47)
Atggtccgcgcgaggcaccagccgggtgggctttgcctcctgctgctgct gctctgccagttcatggaggaccgcagtgcccaggctgggaactgctggc tccgtcaagcgaagaacggccgctgccaggtcctgtacaagaccgaactg agcaaggaggagtgctgcagcaccggccggctgagcacctcgtggaccga ggaggacgtgaatgacaacacactcttcaagtggatgattttcaacgggg gcgcccccaactgcatcccctgtaaagaaacgtgtgagaacgtggactgt ggacctgggaaaaaatgccgaatgaacaagaagaacaaacccgctgcgt ctgcgccccggattgttccaacatcacctggaagggtccagtctgcgggc tggatgggaaaacctaccgcaatgaatgtgcactcctaaaggcaagatgt aaagagcagccagaactggaagtccagtaccaaggcagatgtaaaaagac ttgtcgggatgttttctgtccaggcagctccacatgtgtggtggaccaga ccaataatgcctactgtgtgacctgtaatcggatttgcccagagcctgct tcctctgagcaatatctctgtgggaatgatggagtcacctactccagtgc ctgccacctgagaaaggctacctgcctgctgggcagatctattggattag cctatgagggaaagtgtatcaaagcaaagtcctgtgaagatatccagtgc actggtgggaaaaaatgtttatgggatttcaaggttgggagaggccggtg ttccctctgtgatgagctgtgccctgacagtaagtcggatgagcctgtct gtgccagtgacaatgccacttatgccagcgagtgtgccatgaaggaagct gcctgctcctcaggtgtgctactggaagtaaagcactccggatcttgcaa ctccatttcggaagacaccgaggaagaggaggaagatgaagaccaggact acagctttcctatatcttctattctagagtgg The following sequence encodes the mature FST315 polypeptide (SEQ ID NO: 48).

(SEQ ID NO: 48)
Gggaactgctggctccgtcaagcgaagaacggccgctgccaggtcctgta caagaccgaactgagcaaggaggagtgctgcagcaccggccggctgagca cctcgtggaccgaggaggacgtgaatgacaacacactcttcaagtggatg attttcaacggggggcgcccccaactgcatcccctgtaaagaaacgtgtga gaacgtggactgtggacctgggaaaaaatgccgaatgaacaagaagaaca aacccgctgcgtctgcgccccggattgttccaacatcacctggaagggt ccagtctgcgggctggatgggaaaacctaccgcaatgaatgtgcactcct aaaggcaagatgtaaagagcagccagaactggaagtccagtaccaaggca gatgtaaaaagacttgtcgggatgttttctgtccaggcagctccacatgt gtggtggaccagaccaataatgcctactgtgtgacctgtaatcggatttg cccagagcctgcttcctctgagcaatatctctgtgggaatgatggagtca cctactccagtgcctgccacctgagaaaggctacctgcctgctgggcaga tctattggattagcctatgagggaaagtgtatcaaagcaaagtcctgtga agatatccagtgcactggtgggaaaaaatgtttatgggatttcaaggttg ggagaggccggtgttccctctgtgatgagctgtgccctgacagtaagtcg gatgagcctgtctgtgccagtgacaatgccacttatgccagcgagtgtgc catgaaggaagctgcctgctcctcaggtgtgctactggaagtaaaagcact ccggatcttgcaactccatttcggaagacaccgaggaagaggaggaagat gaagaccaggactacagctttcctatatcttctattctagagtgg The following sequence encodes the FST288 polypeptide (SEQ ID NO: 49).

(SEQ ID NO: 49)
gggaactgctggctccgtcaagcgaagaacggccgctgccaggtcctgta caagaccgaactgagcaaggaggagtgctgcagcaccggccggctgagca cctcgtggaccgaggaggacgtgaatgacaacacactcttcaagtggatg attttcaacggggggcgcccccaactgcatcccctgtaaagaaacgtgtga gaacgtggactgtggacctgggaaaaaatgccgaatgaacaagaagaaca aacccgctgcgtctgcgccccggattgttccaacatcacctggaagggt ccagtctgcgggctggatgggaaaacctaccgcaatgaatgtgcactcct aaaggcaagatgtaaagagcagccagaactggaagtccagtaccaaggca gatgtaaaaagacttgtcgggatgttttctgtccaggcagctccacatgt gtggtggaccagaccaataatgcctactgtgtgacctgtaatcggatttg cccagagcctgcttcctctgagcaatatctctgtgggaatgatggagtca cctactccagtgcctgccacctgagaaaggctacctgcctgctgggcaga tctattggattagcctatgagggaaagtgtatcaaagcaaagtcctgtga agatatccagtgcactggtgggaaaaaatgtttatgggatttcaaggttg ggagaggccggtgttccctctgtgatgagctgtgccctgacagtaagtcg gatgagcctgtctgtgccagtgacaatgccacttatgccagcgagtgtgc catgaaggaagctgcctgctcctcaggtgtgctactggaagtaaaagcact ccggatcttgcaac The following sequence encodes the mature FST291 polypeptide (SEQ ID NO: 50).

(SEQ ID NO: 50)
Gggaactgctggctccgtcaagcgaagaacggccgctgccaggtcctgta caagaccgaactgagcaaggaggagtgctgcagcaccggccggctgagca cctcgtggaccgaggaggacgtgaatgacaacacactcttcaagtggatg -continued attttcaacgggggcgcccccaactgcatccctgtaaagaaacgtgtga gaacgtggactgtggacctgggaaaaaatgccgaatgaacaagaagaaca aaccccgctgcgtctgcgccccggattgttccaacatcacctggaagggt ccagtctgcgggctggatgggaaaacctaccgcaatgaatgtgcactcct aaaggcaagatgtaaagagcagccagaactggaagtccagtaccaaggca gatgtaaaaagacttgtcgggatgttttctgtccaggcagctccacatgt gtggtggaccagaccaataatgcctactgtgtgacctgtaatcggatttg cccagagcctgcttcctctgagcaatatctctgtgggaatgatggagtca cctactccagtgcctgccacctgagaaaggctacctgcctgctgggcaga -continued tctattggattagcctatgagggaaagtgtatcaaagcaaagtcctgtga agatatccagtgcactggtgggaaaaaatgtttatgggatttcaaggttg ggagaggccggtgttccctctgtgatgagctgtgccctgacagtaagtcg gatgagcctgtctgtgccagtgacaatgccacttatgccagcgagtgtgc catgaaggaagctgcctgctcctcaggtgtgctactggaagtaaagcact ccggatcttgcaactccatttcgtgg For example, the following sequence (SEQ ID NO: 51) encodes a naturally occurring human FLRG precursor polypeptide (nucleotides 36-824 of NCBI Reference Sequence NM_005860.2). Nucleotides encoding the signal sequence are underlined.

(SEQ ID NO: 51)
1   atgcgtcccg gggcgccagg gccactctgg cctctgccct gggggggccct 51  ggcttgggcc gtgggcttcg tgagctccat gggctcgggg aaccccgcgc 101 ccggtggtgt ttgctggctc cagcagggcc aggaggccac ctgcagcctg 151 gtgctccaga ctgatgtcac ccgggccgag tgctgtgcct ccggcaacat 201 tgacaccgcc tggtccaacc tcacccaccc ggggaacaag atcaacctcc 251 tcggcttctt gggccttgtc cactgccttc cctgcaaaga ttcgtgcgac 301 ggcgtggagt gcggcccggg caaggcgtgc cgcatgctgg ggggccgccc 351 gcgctgcgag tgcgcgcccg actgctcggg gctcccggcg cggctgcagg 401 tctgcggctc agacggcgcc acctaccgcg acgagtgcga gctgcgcgcc 451 gcgcgctgcc gcggccaccc ggacctgagc gtcatgtacc ggggccgctg 501 ccgcaagtcc tgtgagcacg tggtgtgccc gcggccacag tcgtgcgtcg 551 tggaccagac gggcagcgcc cactgcgtgg tgtgtcgagc ggcgccctgc 601 cctgtgccct ccagccccgg ccaggagctt tgcggcaaca caacgtcac 651 ctacatctcc tcgtgccaca tgcgccaggc cacctgcttc ctgggccgct 701 ccatcggcgt gcgccacgcg ggcagctgcg caggcacccc tgaggagccg 751 ccaggtggtg agtctgcaga agaggaagag aacttcgtg The following sequence (SEQ ID NO: 52) encodes a mature human FLRG polypeptide (nucleotides 114-824 of NCBI Reference Sequence NM_005860.2).

(SEQ ID NO: 52)
1   atgggctcgg ggaacccccgc gcccggtggt gtttgctggc tccagcaggg 51  ccaggaggcc acctgcagcc tggtgctcca gactgatgtc acccgggccg 101 agtgctgtgc ctccggcaac attgacaccg cctggtccaa cctcacccac 151 ccggggaaca agatcaacct cctcggcttc ttgggccttg tccactgcct 201 tccctgcaaa gattcgtgcg acggcgtgga gtgcggcccg gcaaggcgt 251 gccgcatgct gggggccgc ccgcgctgcg agtgcgcgcc cgactgctcg 301 gggctcccgg cgcggctgca ggtctgcggc tcagacggcg ccacctaccg 351 cgacgagtgc gagctgcgcg ccgcgcgctg ccgcggccac ccggacctga 401 gcgtcatgta ccggggccgc tgccgcaagt cctgtgagca cgtggtgtgc 451 ccgcggccac agtcgtgcgt cgtggaccag acgggcagcg cccactgcgt -continued

```
501 ggtgtgtcga gcggcgccct gccctgtgcc ctccagcccc ggccaggagc 551 tttgcggcaa caacaacgtc acctacatct cctcgtgcca catgcgccag 601 gccacctgct tcctgggccg ctccatcggc gtgcgccacg cgggcagctg 651 cgcaggcacc cctgaggagc cgccaggtgg tgagtctgca gaagaggaag 701 agaacttcgt g
```

For example, the following sequence (SEQ ID NO: 53) encodes a naturally occurring human WFIKKN1 precursor polypeptide (nucleotides 243-1886 of NCBI Reference Sequence NM_053284.2). Nucleotides encoding the signal sequence are underlined.

(SEQ ID NO: 53)
```
   1 atgcccgccc tacgtccact cctgccgctc ctgctcctcc tccggctgac 51 ctcgggggct ggcttgctgc cagggctggg gagccacccg ggcgtgtgcc 101 ccaaccagct cagccccaac ctgtgggtgg acgcccagag cacctgtgag 151 cgcgagtgta gcaggaccca ggactgtgcg gctgctgaga agtgctgcat 201 caacgtgtgt ggactgcaca gctgcgtggc agcacgcttc cccggcagcc 251 cagctgcgcc gacgacagcg gcctcctgcg agggcttggt gtgcccacag 301 cagggctcgg actgcgacat ctgggacggg cagcccgtgt gccgctgccg 351 cgaccgctgt gagaaggagc ccagcttcac ctgcgcctcg gacggcctca 401 cctactacaa ccgctgctat atggacgccg aggcctgcct gcggggcctg 451 cacctccaca tcgtgccctg caagcacgtg ctcagctggc cgcccagcag 501 cccggggccg ccggagacca ctgcccgccc cacacctggg gccgcgcccg 551 tgcctcctgc cctgtacagc agcccctccc cacaggcggt gcaggttggg 601 ggtacggcca gcctccactg cgacgtcagc ggccgcccgc cgcctgctgt 651 gacctgggag aagcagagtc accagcgaga gaacctgatc atgcgccctg 701 atcagatgta tggcaacgtg gtggtcacca gcatcgggca gctggtgctc 751 tacaacgcgc ggcccgaaga cgccggcctg tacacctgca ccgcgcgcaa 801 cgctgctggg ctgctgcggg ctgacttccc actctctgtg gtccagcgag 851 agccggccag ggacgcagcc cccagcatcc agccccggc cgagtgcctg 901 ccggatgtgc aggcctgcac gggcccccact tccccacacc ttgtcctctg 951 gcactacgac ccgcagcggg gcggctgcat gaccttcccg gcccgtggct 1001 gtgatggggc ggcccgcggc tttgagacct acgaggcatg ccagcaggcc 1051 tgtgcccgcg gccccggcga cgcctgcgtg ctgcctgccg tgcagggccc 1101 ctgccggggc tggagccgc gctgggccta cagcccgctg ctgcagcagt 1151 gccatcccctt cgtgtacggt ggctgcgagg gcaacggcaa caacttccac 1201 agccgcgaga gctgcgagga tgcctgcccc gtgccgcgca caccgccctg 1251 ccgcgcctgc cgcctccgga gcaagctggc gctgagcctg tgccgcagcg 1301 acttcgccat cgtggggcgg ctcacggagg tgctggagga gcccgaggcc 1351 gccggcggca tcgcccgcgt ggcgctcgag gacgtgctca aggatgacaa 1401 gatgggcctc aagttcttgg gcaccaagta cctggaggtg acgctgagtg 1451 gcatggactg ggcctgcccc tgccccaaca tgacggcggc gacgggccg
```

-continued
```
1501 ctggtcatca tgggtgaggt gcgcgatggc gtggccgtgc tggacgccgg 1551 cagctacgtc cgcgccgcca gcgagaagcg cgtcaagaag atcttggagc 1601 tgctggagaa gcaggcctgc gagctgctca accgcttcca ggac
```

The following sequence (SEQ ID NO: 54) encodes a mature human WFIKKN1 polypeptide (nucleotides 300-1886 of NCBI Ref Seq NM_053284.2).

```
                                                    (SEQ ID NO: 54)
   1 gctggcttgc tgccagggct ggggagccac ccgggcgtgt gccccaacca 51 gctcagcccc aacctgtggg tggacgccca gagcacctgt gagcgcgagt 101 gtagcaggga ccaggactgt gcggctgctg agaagtgctg catcaacgtg 151 tgtggactgc acagctgcgt ggcagcacgc ttccccggca gcccagctgc 201 gccgacgaca gcggcctcct gcgagggctt tgtgtgccca gcagggct 251 cggactgcga catctgggac gggcagcccg tgtgccgctg ccgcgaccgc 301 tgtgagaagg agcccagctt cacctgcgcc tcggacggcc tcacctacta 351 caaccgctgc tatatggacg ccgaggcctg cctgcggggc ctgcacctcc 401 acatcgtgcc ctgcaagcac gtgctcagct ggccgcccag cagcccgggg 451 ccgccggaga ccactgcccg ccccacacct ggggccgcgc ccgtgcctcc 501 tgccctgtac agcagcccct cccacaggc ggtgcaggtt gggggtacgg 551 ccagcctcca ctgcgacgtc agcggccgcc cgccgcctgc tgtgacctgg 601 gagaagcaga gtcaccagcg agagaacctg atcatgcgcc tgatcagat 651 gtatggcaac gtggtggtca ccagcatcgg gcagctggtg ctctacaacg 701 cgcggcccga agacgccggc ctgtacacct gcaccgcgcg caacgctgct 751 gggctgctgc gggctgactt cccactctct gtggtccagc gagagccggc 801 cagggacgca gcccccagca tcccagcccc ggccgagtgc ctgccggatg 851 tgcaggcctg cacgggcccc acttccccac accttgtcct ctggcactac 901 gacccgcagc ggggcggctg catgaccttc ccggcccgtg ctgtgatggg 951 ggcggcccgc ggctttgaga cctacgaggc atgccagcag gcctgtgccc 1001 gcggcccccgg cgacgcctgc gtgctgcctg ccgtgcaggg ccctgccgg 1051 ggctgggagc cgcgctgggc ctacagcccg ctgctgcagc agtgccatcc 1101 cttcgtgtac ggtggctgcg agggcaacgg caacaacttc cacagccgcg 1151 agagctgcga ggatgcctgc cccgtgccgc gcacaccgcc ctgccgcgcc 1201 tgccgcctcc ggagcaagct ggcgctgagc ctgtgccgca gcgacttcgc 1251 catcgtgggg cggctcacgg aggtgctgga ggagcccgag gccgccggcg 1301 gcatcgcccg cgtggcgctc gaggacgtgc tcaaggatga caagatgggc 1351 ctcaagttct tgggcaccaa gtacctggag gtgacgctga gtggcatgga 1401 ctgggcctgc ccctgcccca acatgacggc gggcgacggg ccgctggtca 1451 tcatgggtga ggtgcgcgat ggcgtggccg tgctggacgc cggcagctac 1501 gtccgcgccg ccagcgagaa gcgcgtcaag aagatcttgg agctgctgga 1551 gaagcaggcc tgcgagctgc tcaaccgctt ccaggac
```

For example, the following sequence (SEQ ID NO: 55) encodes a naturally occurring human WFIKKN2 precursor polypeptide (nucleotides 695-2422 of NCBI Reference Sequence NM_175575.5). Nucleotides encoding the signal sequence are underlined.

```
                                                  (SEQ ID NO: 55)
   1 atgtgggccc caaggtgtcg ccggttctgg tctcgctggg agcaggtggc 51 agcgctgctg ctgctgctgc tactgctcgg ggtgccccg cgaagcctgg 101 cgctgccgcc catccgctat tcccacgccg gcatctgccc caacgacatg 151 aatcccaacc tctgggtgga cgcacagagc acctgcaggc gggagtgtga 201 gacggaccag gagtgtgaga cctatgagaa gtgctgcccc aacgtatgtg 251 ggaccaagag ctgcgtggcg gcccgctaca tggacgtgaa agggaagaag 301 ggcccagtgg gcatgcccaa ggaggccaca tgtgaccact tcatgtgtct 351 gcagcagggc tctgagtgtg acatctggga tggccagccc gtgtgtaagt 401 gcaaagaccg ctgtgagaag gagcccagct ttacctgcgc ctcggacggc 451 ctcacctact ataaccgctg ctacatggat gccgaggcct gctccaaagg 501 catcacactg gccgttgtaa cctgccgcta tcacttcacc tggcccaaca 551 ccagccccc accacctgag accaccatgc accccaccac agcctcccca 601 gagacccctg agctggacat ggcggcccct gcgctgctca acaaccctgt 651 gcaccagtcg gtcaccatgg gtgagacagt gagcttcctc tgtgatgtgg 701 tgggccggcc ccggcctgag atcacctggg agaagcagtt ggaggatcgg 751 gagaatgtgg tcatgcggcc caaccatgtg cgtggcaacg tggtggtcac 801 caacattgcc cagctggtca tctataacgc ccagctgcag gatgctggga 851 tctacacctg cacggcccgg aacgtggctg gggtcctgag ggctgatttc 901 ccgctgtcgg tggtcagggg tcatcaggct gcagccacct cagagagcag 951 ccccaatggc acggctttcc cggcggccga gtgcctgaag ccccagaca 1001 gtgaggactg tggcgaagag cagacccgct ggcacttcga tgcccaggcc 1051 aacaactgcc tgaccttcac cttcggccac tgccaccgta acctcaacca 1101 ctttgagacc tatgaggcct gcatgctggc ctgcatgagc gggccgctgg 1151 ccgcgtgcag cctgcccgcc ctgcagggc cctgcaaagc ctacgcgcct 1201 cgctgggctt acaacagcca gacgggccag tgccagtcct ttgtctatgg 1251 tggctgcgag ggcaatggca acaactttga gagccgtgag gcctgtgagg 1301 agtcgtgccc cttccccagg gggaaccagc gctgtcgggc ctgcaagcct 1351 cggcagaagc tcgttaccag cttctgtcgc agcgactttg tcatcctggg 1401 ccgagtctct gagctgaccg aggagcctga ctcgggccgc gccctggtga 1451 ctgtggatga ggtcctaaag gatgagaaaa tgggcctcaa gttcctgggc 1501 caggagccat tggaggtcac tctgcttcac gtggactggg catgcccctg 1551 ccccaacgtg accgtgagcg agatgccgct catcatcatg ggggaggtgg 1601 acggcggcat ggccatgctg cgccccgata gctttgtggg cgcatcgagt 1651 gccgccgggg tcaggaagct tcgtgaggtc atgcacaaga agacctgtga 1701 cgtcctcaag gagtttcttg gcttgcac
```

The following sequence (SEQ ID NO: 56) encodes a mature human WFIKKN2 polypeptide (nucleotides 797-2422 of NCBI Ref Seq NM_175575.5).

```
                                            (SEQ ID NO: 56)
   1 ctgccgccca tccgctattc ccacgccggc atctgcccca acgacatgaa 51 tcccaacctc tgggtggacg cacagagcac ctgcaggcgg gagtgtgaga 101 cggaccagga gtgtgagacc tatgagaagt gctgcccaa cgtatgtggg 151 accaagagct gcgtggcggc ccgctacatg gacgtgaaag ggaagaaggg 201 cccagtgggc atgcccaagg aggccacatg tgaccacttc atgtgtctgc 251 agcagggctc tgagtgtgac atctgggatg ccagcccgt gtgtaagtgc 301 aaagaccgct gtgagaagga gcccagcttt acctgcgcct cggacggcct 351 cacctactat aaccgctgct acatggatgc cgaggcctgc tccaaaggca 401 tcacactggc cgttgtaacc tgccgctatc acttcacctg gcccaacacc 451 agccccccac cacctgagac caccatgcac cccaccacag cctccccaga 501 gaccctgag ctggacatgg cggcccctgc gctgctcaac aaccctgtgc 551 accagtcggt caccatgggt gagacagtga gcttcctctg tgatgtggtg 601 ggccggcccc ggcctgagat cacctgggag aagcagttgg aggatcggga 651 gaatgtggtc atgcggccca accatgtgcg tggcaacgtg gtggtcacca 701 acattgccca gctggtcatc tataacgccc agctgcagga tgctgggatc 751 tacacctgca cggcccggaa cgtggctggg gtcctgaggg ctgatttccc 801 gctgtcggtg gtcaggggtc atcaggctgc agccacctca gagagcagcc 851 ccaatggcac ggctttcccg gcggccgagt gcctgaagcc cccagacagt 901 gaggactgtg gcgaagagca gacccgctgg cacttcgatg cccaggccaa 951 caactgcctg accttcacct tcggccactg ccaccgtaac ctcaaccact 1001 ttgagaccta tgaggcctgc atgctggcct gcatgagcgg gccgctggcc 1051 gcgtgcagcc tgcccgccct gcaggggccc tgcaaagcct acgcgcctcg 1101 ctgggcttac aacagccaga cgggccagtg ccagtccttt gtctatggtg 1151 gctgcgaggg caatggcaac aactttgaga gccgtgaggc ctgtgaggag 1201 tcgtgcccct ccccaggggg gaaccagcgc tgtcgggcct gcaagcctcg 1251 gcagaagctc gttaccagct tctgtcgcag cgactttgtc atcctgggcc 1301 gagtctctga gctgaccgag gagcctgact cgggccgcgc cctggtgact 1351 gtggatgagg tcctaaagga tgagaaaatg ggcctcaagt cctgggcca 1401 ggagccattg gaggtcactc tgcttcacgt ggactgggca tgccctgcc 1451 ccaacgtgac cgtgagcgag atgccgctca tcatcatggg ggaggtggac 1501 ggcggcatgc ccatgctgcg ccccgatagc tttgtgggcg catcgagtgc 1551 ccgccgggtc aggaagcttc gtgaggtcat gcacaagaag acctgtgacg 1601 tcctcaagga gtttcttggc ttgcac
```

In certain aspects, the subject nucleic acids encoding follistatin-related polypeptides are further understood to include nucleic acids that are variants of SEQ ID NOs: 47-56. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs: 47-56.

In certain embodiments, the disclosure provides isolated or recombinant nucleic acid sequences that are at least 80%, 85%, 90%, 95%, 96% 97%, 98%, 99%, or 100% identical to SEQ ID NOs: 47-56. One of ordinary skill in the art will appreciate that nucleic acid sequences complementary to SEQ ID NOs: 47-56, and variants of SEQ ID NO: 47-56 are also within the scope of this disclosure. In further embodiments, the nucleic acid sequences of the disclosure can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NOs: 47-56, complement sequence of SEQ ID NOs: 47-56, or fragments thereof.

One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids that differ from the nucleic acids as set forth in SEQ ID NOs: 47-56 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations that do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the subject nucleic acid is provided in an expression vector comprising a nucleotide sequence encoding a follistatin-related polypeptide and operably linked to at least one regulatory sequence. Regulatory sequences are art-recognized and are selected to direct expression of the follistatin-related polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a follistatin-related polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant follistatin-related polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In certain embodiments, a vector will be designed for production of the subject follistatin-related polypeptides in CHO cells, such as a Pcmv-Script vector (Stratagene, La Jolla, Calif), pcDNA4 vectors (Invitrogen, Carlsbad, Calif.) and pCI-neo vectors (Promega, Madison, Wis.). As will be apparent, the subject gene constructs can be used to cause expression of the subject follistatin-related polypeptides in cells propagated in culture, e.g., to produce proteins, including fusion proteins or variant proteins, for purification.

This disclosure also pertains to a host cell transfected with a recombinant gene including a coding sequence (e.g., SEQ ID NOs: 19-22) for one or more of the subject follistatin-related polypeptides. The host cell may be any prokaryotic or eukaryotic cell. For example, a follistatin-related polypeptide of the disclosure may be expressed in bacterial cells such as *E. coli,* insect cells (e.g., using a baculovirus expression system), yeast, or mammalian cells. Other suitable host cells are known to those skilled in the art.

Accordingly, the present disclosure further pertains to methods of producing the subject follistatin-related polypeptides. For example, a host cell transfected with an expression vector encoding a follistatin-related polypeptide can be cultured under appropriate conditions to allow expression of the follistatin-related polypeptide to occur. The follistatin-related polypeptide may be secreted and isolated from a mixture of cells and medium containing the follistatin-related polypeptide. Alternatively, the follistatin-related polypeptide may be retained cytoplasmically or in a membrane fraction and the cells harvested, lysed and the protein isolated. A cell culture includes host cells, media and other byproducts. Suitable media for cell culture are well known in the art. The subject follistatin-related polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the follistatin polypeptides. In a preferred embodiment, the follistatin-related polypeptide is a fusion protein containing a domain that facilitates its purification.

In another embodiment, a fusion gene coding for a purification leader sequence, such as a poly-(His)/enterokinase cleavage site sequence at the N-terminus of the desired portion of the recombinant follistatin-related polypeptide, can allow purification of the expressed fusion protein by affinity chromatography using a $Ni^{2+}$ metal resin. The purification leader sequence can then be subsequently removed by treatment with enterokinase to provide the purified follistatin-related polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed to generate a chimeric gene sequence (see, for example, *Current Protocols in Molecular Biology*, eds. Ausubel et al., John Wiley & Sons: 1992).

4. Exemplary Therapeutic Uses

In certain embodiments, compositions of the present disclosure, including for example various protein complexes comprising follistatin-related fusion polypeptides disclosed herein, can be used for treating or preventing a disease or condition that is described in this section, including diseases or disorders that are associated with abnormal activity of a follistatin-related polypeptide and/or a follistatin ligand (e.g., myostatin, activins, GDF11). These diseases, disorders or conditions are generally referred to herein as "follistatin-associated conditions." In certain embodiments, the present disclosure provides methods of treating or preventing an individual in need thereof through administering to the individual a therapeutically effective amount of a follistatin-related fusion polypeptide as described above. These methods are particularly aimed at therapeutic and prophylactic treatments of animals, and more particularly, humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes amelioration or elimination of the condition once it has been established. In either case, prevention or treatment may be discerned in the diagnosis provided by a physician or other health care provider and the intended result of administration of the therapeutic agent.

In general, treatment or prevention of a disease or condition as described in the present disclosure is achieved by administering a follistatin-related polypeptide, or compositions, complexes or combinations comprising such polypeptide, of the present disclosure in an "effective amount". An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

Follistatin-ligand complexes play essential roles in tissue growth as well as early developmental processes such as the correct formation of various structures or in one or more post-developmental capacities including sexual development, pituitary hormone production, and creation of muscle. Thus, follistatin-associated conditions include abnormal tissue growth and developmental defects.

Exemplary conditions for treatment include neuromuscular disorders (e.g., muscular dystrophy and muscle atrophy), congestive obstructive pulmonary disease (and muscle wasting associated with COPD), muscle wasting syndrome, sarcopenia, and cachexia, adipose tissue disorders (e.g., obesity), type 2 diabetes (NIDDM, adult-onset diabetes), and bone degenerative disease (e.g., osteoporosis). Other exemplary conditions include musculodegenerative and neuromuscular disorders, tissue repair (e.g., wound healing), and neurodegenerative diseases (e.g., amyotrophic lateral sclerosis).

In certain embodiments, compositions (e.g., follistatin-related fusion proteins) of the invention are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject follistatin-related polypeptides include: Duchenne muscular dystrophy (DMD), Becker muscular dystrophy (BMD), Emery-Dreifuss muscular dystrophy (EDMD), limb-girdle muscular dystrophy (LGMD), facioscapulohumeral muscular dystrophy (FSH or FSHD) (also known as Landouzy-Dejerine), myotonic mystrophy (MMD) (also known as Steinert's Disease), oculopharyngeal muscular dystrophy (OPMD), distal muscular dystrophy (DD), congenital muscular dystrophy (CMD).

Duchenne muscular dystrophy (DMD) was first described by the French neurologist Guillaume Benjamin Amand Duchenne in the 1860s. Becker muscular dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either insufficient in quantity or poor in quality. Having some dystrophin protects the muscles of those with BMD from degenerating as badly or as quickly as those of people with DMD.

For example, recent researches demonstrate that blocking or eliminating function of myostatin (a follistatin ligand) in vivo can effectively treat at least certain symptoms in DMD and BMD patients. Thus, the subject follistatin-related fusion polypeptides may act as myostatin inhibitors (antagonists), and constitute an alternative means of blocking the functions of myostatin in vivo in DMD and BMD patients.

Similarly, the subject follistatin-related fusion polypeptides provide an effective means to increase muscle mass in other disease conditions that are in need of muscle growth. For example, amyotrophic lateral sclerosis (ALS, also called Lou Gehrig's disease or motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles. Most people who get ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset.

Increased muscle mass induced by follistatin-related fusion polypeptides might also benefit those suffering from muscle wasting diseases. Myostatin expression correlates inversely with fat-free mass in humans and that increased expression of the MSTN gene is associated with weight loss in men with AIDS wasting syndrome. By inhibiting the function of myostatin in AIDS patients, at least certain symptoms of AIDS may be alleviated, if not completely eliminated, thus significantly improving quality of life in AIDS patients.

Cancer anorexia-cachexia syndrome is among the most debilitating and life-threatening aspects of cancer. This syndrome is a common feature of many types of cancer— present in approximately 80% of cancer patients at death— and is responsible not only for a poor quality of life and poor response to chemotherapy but also a shorter survival time than is found in patients with comparable tumors but without weight loss. Cachexia is typically suspected in patients with cancer if an involuntary weight loss of greater than five percent of premorbid weight occurs within a six-month period. Associated with anorexia, wasting of fat and muscle tissue, and psychological distress, cachexia arises from a complex interaction between the cancer and the host. Cancer cachexia affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Currently, there is no treatment to control or reverse the cachexic process. Since systemic overexpression of GDF8 in adult mice was found to induce profound muscle and fat loss analogous to that seen in human cachexia syndromes (Zimmers et al., supra), the subject follistatin-related polypeptides may be beneficially used to prevent, treat, or alleviate the symptoms of the cachexia syndrome, where muscle growth is desired.

In other embodiments, follistatin-related fusion polypeptides, or combinations of such polypeptides, can be used for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present disclosure relates to regulating body weight by administering to an animal (e.g., a human) in need thereof a follistatin-related fusion polypeptides, or combinations of such polypeptides of the disclosure.

In some embodiments, follistatin-related fusion polypeptides, or combinations of such polypeptides, of the present disclosure can be used for reducing body weight and/or reducing weight gain in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass. In addition, disorders of high cholesterol (e.g., hypercholesterolemia or dislipidemia) may be treated with an follistatin-related fusion polypeptides, or combinations of such polypeptides, of the disclosure.

In some embodiments, follistatin-related fusion polypeptides, or combinations of such polypeptides, of the present disclosure can be used for treating a metabolic disorder such as type II diabetes, metabolic syndrome, hyperadinectonemia, hyperglycemia or hyperinsulinemia.

Fibrosis generally refers to an excessive deposition of both collagen fibers and extracellular matrix combined with a relative decrease of cell number in an organ or tissue. While this process is an important feature of natural wound healing following injury, fibrosis can lead to pathological damage in various tissue and organs including, for example, the lungs, kidneys, liver, bone, muscle, and skin. The role the TGF-beta superfamily in fibrosis has been extensively study. TGF-beta superfamily ligands have been implicated in fibrosis including, for example, activins (e.g., activin A and activin B) and GDF8 [Hedger et al (2013) Cytokine and Growth Factor Reviews 24:285-295; Hardy et al. (2015) 93: 567-574; and Cantini et al. (2008) J Sex Med 5:1607-1622]. Therefore, in some embodiments, follistatin-related fusion polypeptides, or combinations of such polypeptides, of the present disclosure can be used to treat fibrosis, particularly fibrosis-associated disorders and conditions. For example, follistatin-related fusion polypeptides, or combinations of such polypeptides, may be used to treat or prevent one or more of: pulmonary fibrosis, hypersensitivity pneumonitis, idiopathic fibrosis, tuberculosis, pneumonia, cystic fibrosis, asthma, chronic obstructive pulmonary disease (COPD), emphysema, renal (kidney) fibrosis, renal (kidney) failure, chronic renal (kidney) disease, bone fibrosis, myelofibrosis, rheumatoid arthritis, systemic lupus erythematosus, scleroderma, sarcoidosis, granulomatosis with polyangiitis, Peyronie's disease, liver fibrosis, Wilson's disease, glycogen storage diseases (particularly types III, IV, IX, and X), iron-overload, Gaucher disease, Zellweger syndrome, non-alcoholic and alcoholic steatohepatitis, biliary cirrhosis, sclerosing cholangitis, Budd-Chiari syndrome, surgery-associated fibrosis, Crohn's disease, Duputren's contracture, mediastinal fibrosis, nephrogeneic fibrosis, retroperitoneal fibrosis, atrial fibrosis, endomyocardial fibrosis, pancreatic fibrosis.

In some embodiments, follistatin-related fusion polypeptides, or combinations of such polypeptides, of the present disclosure may be used to treat or prevent chronic kidney disease, optionally in combination with one or more supportive therapies for treating chronic kidney disease. In some embodiments, follistatin-related fusion polypeptides, or combinations of such polypeptides, of the present disclosure may be used to treat or prevent one or more complications (symptoms or manifestations) of chronic kidney disease, optionally in combination with one or more supportive therapies for treating chronic kidney disease. In some embodiments, follistatin-related fusion polypeptides, or combinations of such polypeptides, of the present disclosure may be used to treat or prevent end-stage kidney failure, optionally in combination with one or more supportive therapies for treating end-stage kidney disease. Chronic kidney disease (CKD), also known as chronic renal disease, is a progressive loss in renal function over a period of months or years. The symptoms of worsening kidney function may include feeling generally unwell and experiencing a reduced appetite. Often, chronic kidney disease is diagnosed as a result of screening of people known to be at risk of kidney problems, such as those with high blood pressure or diabetes and those with a blood relative with CKD. This disease may also be identified when it leads to one of its recognized complications, such as cardiovascular disease, anemia, or pericarditis. Recent professional guidelines classify the severity of CKD in five stages, with stage 1 being the mildest and usually causing few symptoms and stage 5 being a severe illness with poor life expectancy if untreated. Stage 5 CKD is often called end-stage kidney disease, end-stage renal disease, or end-stage kidney failure, and is largely synonymous with the now outdated terms chronic renal failure or chronic kidney failure; and usually means the patient requires renal replacement therapy, which may involve a form of dialysis, but ideally constitutes a kidney transplant. CKD is initially without specific symptoms and is generally only detected as an increase in serum creatinine or protein in the urine. As the kidney function decreases and various symptoms may manifest as described below. Blood pressure may be increased due to fluid overload and production of vasoactive hormones created by the kidney via the renin-angiotensin system, increasing one's risk of developing hypertension and/or suffering from congestive heart failure. Urea may accumulate, leading to azotemia and ultimately uremia (symptoms ranging from lethargy to pericarditis and encephalopathy). Due to its high systemic circulation, urea is excreted in eccrine sweat at high concentrations and crystallizes on skin as the sweat evaporates ("uremic frost"). Potassium may accumulate in the blood (hyperkalemia with a range of symptoms including malaise and potentially fatal cardiac arrhythmias). Hyperkalemia usually does not develop until the glomerular filtration rate falls to less than 20-25 ml/min/1.73 m2, at which point the kidneys have decreased ability to excrete potassium. Hyperkalemia in CKD can be exacerbated by acidemia (which leads to extracellular shift of potassium) and from lack of insulin. Erythropoietin synthesis may be decreased causing anemia. Fluid volume overload symptoms may occur, ranging from mild edema to life-threatening pulmonary edema. Hyperphosphatemia, due to reduced phosphate excretion, may occur generally following the decrease in glomerular filtration. Hyperphosphatemia is associated with increased cardiovascular risk, being a direct stimulus to vascular calcification. Hypocalcemia may manifest, which is generally caused by stimulation of fibroblast growth factor-23. Osteocytes are responsible for the increased production of FGF23, which is a potent inhibitor of the enzyme 1-alpha-hydroxylase (responsible for the conversion of 25-hydroxycholecalciferol into 1,25 dihydroxyvitamin D3). Later, this progresses to secondary hyperparathyroidism, renal osteodystrophy, and vascular calcification that further impairs cardiac function. Metabolic acidosis (due to accumulation of sulfates, phosphates, uric acid etc.) may occur and cause altered enzyme activity by excess acid acting on enzymes; and also increased excitability of cardiac and neuronal membranes by the promotion of hyperkalemia due to excess acid (acidemia). Acidosis is also due to decreased capacity to generate enough ammonia from the cells of the proximal tubule. Iron deficiency anemia, which increases in prevalence as kidney function decreases, is especially prevalent in those requiring haemodialysis. It is multifactoral in cause, but includes increased inflammation, reduction in erythropoietin, and hyperuricemia leading to bone marrow suppression. People with CKD suffer from accelerated atherosclerosis and are more likely to develop cardiovascular disease than the general population. Patients afflicted with CKD and cardiovascular disease tend to have significantly worse prognoses than those suffering only from the latter.

As used herein, "in combination with", "combinations of", or "conjoint administration" refers to any form of administration such that additional therapies (e.g., second, third, fourth, etc.) are still effective in the body (e.g., multiple compounds are simultaneously effective in the patient, which may include synergistic effects of those compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more follistatin-related fusion polypeptides, or combinations of such polypeptides of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired.

5. Pharmaceutical Compositions

In certain embodiments, compounds (e.g., follistatin-related polypeptides) of the present invention are formulated with a pharmaceutically acceptable carrier. For example, a follistatin-related polypeptide can be administered alone or as a component of a pharmaceutical formulation (i.e., a therapeutic composition). The subject compounds may be formulated for administration in any convenient way for use in human or veterinary medicine.

In certain embodiments, the therapeutic method of the invention includes administering the composition topically, systemically, locally, or locally as an implant or device. When administered, the therapeutic composition for use in this invention is, of course, in a pyrogen-free, physiologically acceptable form. Further, the composition may desirably be encapsulated or injected in a viscous form for delivery to a target tissue site (e.g., bone, cartilage, muscle, fat or neurons), for example, a site having tissue damage. Topical administration may be suitable for wound healing and tissue repair. Therapeutically useful agents other than the follistatin-related polypeptides, which may also optionally be included in the composition as described above, may alternatively or additionally, be administered simultaneously or sequentially with the subject compounds (e.g., follistatin-related polypeptides) in the methods of the invention.

In certain embodiments, compositions of the present invention may include a matrix capable of delivering one or more therapeutic compounds (e.g., follistatin-related polypeptides) to a target tissue site, providing a structure for the developing tissue and optimally capable of being resorbed into the body. For example, the matrix may provide slow release of the follistatin-related polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above-mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required. The ointments, pastes, creams and gels may contain, in addition to a subject compound of the invention (e.g., a follistatin-related polypeptide), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise one or more follistatin-related polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption, such as aluminum monostearate and gelatin.

It is understood that the dosage regimen will be determined by the attending physician, considering various factors that modify the action of the subject compounds of the invention (e.g., follistatin-related polypeptides). The various factors will depend upon the disease to be treated.

In certain embodiments, the present invention also provides gene therapy for the in vivo production of follistatin-related polypeptides or other compounds disclosed herein. Such therapy would achieve its therapeutic effect by introduction of the follistatin-related polynucleotide sequences into cells or tissues having the disorders as listed above. Delivery of follistatin-related polynucleotide sequences can be achieved using a recombinant expression vector such as a chimeric virus or a colloidal dispersion system. Preferred for therapeutic delivery of follistatin-related polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the follistatin-related polynucleotide. In one preferred embodiment, the vector is targeted to bone, cartilage, muscle or neuron cells/tissues.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for follistatin-related polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and di stearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1. Generation of a Single-Arm WFIKKN2 Polypeptide Fusion Protein

Applicants generated a soluble asymmetric Fc fusion protein in which native full-length human WFIKKN2 polypeptide was attached through a linker to one of two human G1Fc chains.

A methodology for promoting formation of WFIKKN2-Fc heteromeric complexes, as opposed to WFIKKN2-Fc homodimeric complexes, is to introduce alterations in the amino acid sequence of the Fc domains to guide the formation of asymmetric heteromeric complexes. Many different approaches to making asymmetric interaction pairs using Fc domains are described in this disclosure.

In one approach, illustrated in the polypeptide sequences of SEQ ID NOs: 57 and 58, one Fc domain is altered to introduce cationic amino acids at the interaction face, while the other Fc domain is altered to introduce anionic amino acids at the interaction face. In this example, correct pairing of the two polypeptide chains is promoted through a charge-based mechanism by substituting lysine residues at two positions (underlined) in WFIKKN2-G1Fc(E134K/D177K) (SEQ ID NO: 57) and aspartate residues at two positions (underlined) in G1Fc(K170D/K187D) (SEQ ID NO: 58). An optional N-terminal extension of 13 amino acids (underlined) is included on the short chain (SEQ ID NO: 58) to facilitate disulfide bond formation by the cysteine at position 4.

```
                                                       (SEQ ID NO: 57)
  1 LPPIRYSHAG ICPNDMNPNL WVDAQSTCRR ECETDQECET YEKCCPNVCG

51 TKSCVAARYM DVKGKKGPVG MPKEATCDHF MCLQQGSECD IWDGQPVCKC

101 KDRCEKEPSF TCASDGLTYY NRCYMDAEAC SKGITLAVVT CRYHFTWPNT

151 SPPPPETTMH PTTASPETPE LDMAAPALLN NPVHQSVTMG ETVSFLCDVV

201 GRPRPEITWE KQLEDRENVV MRPNHVRGNV VVTNIAQLVI YNAQLQDAGI

251 YTCTARNVAG VLRADFPLSV VRGHQAAATS ESSPNGTAFP AAECLKPPDS

301 EDCGEEQTRW HFDAQANNCL TFTFGHCHRN LNHFETYEAC MLACMSGPLA

351 ACSLPALQGP CKAYAPRWAY NSQTGQCQSF VYGGCEGNGN NFESREACEE

401 SCPFPRGNQR CRACKPRQKL VTSFCRSDFV ILGRVSELTE EPDSGRALVT

451 VDEVLKDEKM GLKFLGQEPL EVTLLHVDWA CPCPNVTVSE MPLIIMGEVD

501 GGMAMLRPDS FVGASSARRV RKLREVMHKK TCDVLKEFLG LHTGGGGSGG

551 GGSGGGGSGG GGSTHTCPPC PAPELLGGPS VFLFPPKPKD TLMISRTPEV

601 TCVVVDVSHE DPEVKFNWYV DGVEVHNAKT KPREEQYNST YRVVSVLTVL

651 HQDWLNGKEY KCKVSNKALP APIEKTISKA KGQPREPQVY TLPPSRKEMT

701 KNQVSLTCLV KGFYPSDIAV EWESNGQPEN NYKTTPPVLK SDGSFFLYSK

751 LTVDKSRWQQ GNVFSCSVMH EALHNHYTQK SLSLSPGK (SEQ ID NO: 58)
-13 SNTKVDKRVT GGG

1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF
```

```
151 YPSDIAVEWE SNGQPENNYD TTPPVLDSDG SFFLYSDLTV DKSRWQQGNV

201 FSCSVMHEAL HNHYTQKSLS LSPGK
```

Corresponding nucleic acid sequences for the mature (processed) forms of these variants are SEQ ID NOs: 59, 60.

```
                                                    (SEQ ID NO: 59)
   1 CTGCCGCCCA TCCGCTATTC CCACGCCGGC ATCTGCCCCA ACGACATGAA

51 TCCCAACCTC TGGGTGGACG CACAGAGCAC CTGCAGGCGG GAGTGTGAGA

101 CGGACCAGGA GTGTGAGACC TATGAGAAGT GCTGCCCCAA CGTATGTGGG

151 ACCAAGAGCT GCGTGGCGGC CCGCTACATG GACGTGAAAG GGAAGAAGGG

201 CCCAGTGGGC ATGCCCAAGG AGGCCACATG TGACCACTTC ATGTGTCTGC

251 AGCAGGGCTC TGAGTGTGAC ATCTGGGATG CCAGCCCGT GTGTAAGTGC

301 AAAGACCGCT GTGAGAAGGA GCCCAGCTTT ACCTGCGCCT CGGACGGCCT

351 CACCTACTAT AACCGCTGCT ACATGGATGC CGAGGCCTGC TCCAAAGGCA

401 TCACACTGGC CGTTGTAACC TGCCGCTATC ACTTCACCTG GCCCAACACC

451 AGCCCCCCAC CACCTGAGAC CACCATGCAC CCCACCACAG CCTCCCCAGA

501 GACCCCTGAG CTGGACATGG CGGCCCCTGC GCTGCTCAAC AACCCTGTGC

551 ACCAGTCGGT CACCATGGGT GAGACAGTGA GCTTCCTCTG TGATGTGGTG

601 GGCCGGCCCC GGCCTGAGAT CACCTGGGAG AAGCAGTTGG AGGATCGGGA

651 GAATGTGGTC ATGCGGCCCA ACCATGTGCG TGGCAACGTG GTGGTCACCA

701 ACATTGCCCA GCTGGTCATC TATAACGCCC AGCTGCAGGA TGCTGGGATC

751 TACACCTGCA CGGCCCGGAA CGTGGCTGGG GTCCTGAGGG CTGATTTCCC

801 GCTGTCGGTG GTCAGGGGTC ATCAGGCTGC AGCCACCTCA GAGAGCAGCC

851 CCAATGGCAC GGCTTTCCCG GCGGCCGAGT GCCTGAAGCC CCCCGACAGT

901 GAGGACTGTG GCGAAGAGCA GACCCGCTGG CACTTCGATG CCCAGGCCAA

951 CAACTGCCTG ACCTTCACCT TCGGCCACTG CCACCGTAAC CTCAACCACT

1001 TTGAGACCTA TGAGGCCTGC ATGCTGGCCT GCATGAGCGG GCCGCTGGCC

1051 GCGTGCAGCC TGCCCGCCCT GCAGGGGCCC TGCAAAGCCT ACGCGCCTCG

1101 CTGGGCTTAC AACAGCCAGA CGGGCCAGTG CCAGTCCTTT GTCTATGGTG

1151 GCTGCGAGGG CAATGGCAAC AACTTTGAGA GCCGTGAGGC CTGTGAGGAG

1201 TCGTGCCCCT TCCCCAGGGG GAACCAGCGC TGTCGGGCCT GCAAGCCTCG

1251 GCAGAAGCTC GTTACCAGCT TCTGTCGCAG CGACTTTGTC ATCCTGGGCC

1301 GAGTCTCTGA GCTGACCGAG GAGCCTGACT CGGGCCGCGC CCTGGTGACT

1351 GTGGATGAGG TCCTAAAGGA TGAGAAAATG GGCCTCAAGT TCCTGGGCCA

1401 GGAGCCATTG GAGGTCACTC TGCTTCACGT GGACTGGGCA TGCCCCTGCC

1451 CCAACGTGAC CGTGAGCGAG ATGCCGCTCA TCATCATGGG GGAGGTGGAC

1501 GGCGGCATGG CCATGCTGCG CCCCGATAGC TTTGTGGGCG CATCGAGTGC

1551 CCGCCGGGTC AGGAAGCTTC GTGAGGTCAT GCACAAGAAG ACCTGTGACG

1601 TCCTCAAGGA GTTTCTTGGC TTGCACACCG GTGGTGGAGG TTCTGGAGGT

1651 GGAGGAAGTG GTGGAGGTGG TTCTGGAGGT GGTGGAAGTA CTCACACATG

1701 CCCACCGTGC CCAGCACCTG AACTCCTGGG GGGACCGTCA GTCTTCCTCT
```

```
1751 TCCCCCCAAA ACCCAAGGAC ACCCTCATGA TCTCCCGGAC CCCTGAGGTC

1801 ACATGCGTGG TGGTGGACGT GAGCCACGAA GACCCTGAGG TCAAGTTCAA

1851 CTGGTACGTG GACGGCGTGG AGGTGCATAA TGCCAAGACA AAGCCGCGGG

1901 AGGAGCAGTA CAACAGCACG TACCGTGTGG TCAGCGTCCT CACCGTCCTG

1951 CACCAGGACT GGCTGAATGG CAAGGAGTAC AAGTGCAAGG TCTCCAACAA

2001 AGCCCTCCCA GCCCCCATCG AGAAAACCAT CTCCAAAGCC AAAGGGCAGC

2051 CCCGAGAACC ACAGGTGTAC ACCCTGCCCC CATCCCGGAA GGAGATGACC

2101 AAGAACCAGG TCAGCCTGAC CTGCCTGGTC AAAGGCTTCT ATCCCAGCGA

2151 CATCGCCGTG GAGTGGGAGA GCAATGGGCA GCCGGAGAAC AACTACAAGA

2201 CCACGCCTCC CGTGCTGAAG TCCGACGGCT CCTTCTTCCT CTATAGCAAG

2251 CTCACCGTGG ACAAGAGCAG GTGGCAGCAG GGGAACGTCT TCTCATGCTC

2301 CGTGATGCAT GAGGCTCTGC ACAACCACTA CACGCAGAAG AGCCTCTCCC

2351 TGTCTCCGGG TAAA
```

(SEQ ID NO: 60)
```
  1 AGCAACACCA AGGTGGACAA GAGAGTTACC GGTGGTGGAA CTCACACATG

51 CCCACCGTGC CCAGCACCTG AACTCCTGGG GGGACCGTCA GTCTTCCTCT

101 TCCCCCCAAA ACCCAAGGAC ACCCTCATGA TCTCCCGGAC CCCTGAGGTC

151 ACATGCGTGG TGGTGGACGT GAGCCACGAA GACCCTGAGG TCAAGTTCAA

201 CTGGTACGTG GACGGCGTGG AGGTGCATAA TGCCAAGACA AAGCCGCGGG

251 AGGAGCAGTA CAACAGCACG TACCGTGTGG TCAGCGTCCT CACCGTCCTG

301 CACCAGGACT GGCTGAATGG CAAGGAGTAC AAGTGCAAGG TCTCCAACAA

351 AGCCCTCCCA GCCCCCATCG AGAAAACCAT CTCCAAAGCC AAAGGGCAGC

401 CCCGAGAACC ACAGGTGTAC ACCCTGCCCC CATCCCGGGA GGAGATGACC

451 AAGAACCAGG TCAGCCTGAC CTGCCTGGTC AAAGGCTTCT ATCCCAGCGA

501 CATCGCCGTG GAGTGGGAGA GCAATGGGCA GCCGGAGAAC AACTACGACA

551 CCACGCCTCC CGTGCTGGAC TCCGACGGCT CCTTCTTCCT CTATAGCGAC

601 CTCACCGTGG ACAAGAGCAG GTGGCAGCAG GGGAACGTCT TCTCATGCTC

651 CGTGATGCAT GAGGCTCTGC ACAACCACTA CACGCAGAAG AGCCTCTCCC

701 TGTCTCCGGG TAAA
```

The proteins of SEQ ID NO: 57 and SEQ ID NO: 58 may be co-expressed and purified from a CHO cell line, to give rise to a heteromeric complex comprising WFIKKN2-Fc.

In another approach to promote the formation of heteromultimer complexes using asymmetric Fc fusion proteins the Fc domains are altered to introduce complementary hydrophobic interactions and an additional intermolecular disulfide bond as illustrated in the polypeptide sequences of SEQ ID NOs: 71 and 72.

(SEQ ID NO: 71)
```
  1 LPPIRYSHAG ICPNDMNPNL WVDAQSTCRR ECETDQECET YEKCCPNVCG

51 TKSCVAARYM DVKGKKGPVG MPKEATCDHF MCLQQGSECD IWDGQPVCKC

101 KDRCEKEPSF TCASDGLTYY NRCYMDAEAC SKGITLAVVT CRYHFTWPNT

151 SPPPPETTMH PTTASPETPE LDMAAPALLN NPVHQSVTMG ETVSFLCDVV

201 GRPRPEITWE KQLEDRENVV MRPNHVRGNV VVTNIAQLVI YNAQLQDAGI

251 YTCTARNVAG VLRADFPLSV VRGHQAAATS ESSPNGTAFP AAECLKPPDS

301 EDCGEEQTRW HFDAQANNCL TFTFGHCHRN LNHFETYEAC MLACMSGPLA
```

```
351 ACSLPALQGP CKAYAPRWAY NSQTGQCQSF VYGGCEGNGN NFESREACEE

401 SCPFPRGNQR CRACKPRQKL VTSFCRSDFV ILGRVSELTE EPDSGRALVT

451 VDEVLKDEKM GLKFLGQEPL EVTLLHVDWA CPCPNVTVSE MPLIIMGEVD

501 GGMAMLRPDS FVGASSARRV RKLREVMHKK TCDVLKEFLG LHTGGGTHTC

601 PPCPAPELLG GPSVFLFPPK PKDTLMISRT PEVTCVVVDV SHEDPEVKFNW

701 YVDGVEVHNA KTKPREEQYN STYRVVSVLT VLHQDWLNGK EYKCKVSNKAL

801 PAPIEKTISK AKGQPREPQV YTLPPCREEM TKNQVSLWCL VKGFYPSDIAV

901 EWESNGQPEN NYKTTPPVLD SDGSFFLYSK LTVDKSRWQQ GNVFSCSVMHE

1001 ALHNHYTQKS LSLSPGK
```

To promote formation of the heterodimer rather than either of the possible homodimeric complexes, two amino acid substitutions (replacing a serine with a cysteine and a threonine with a trytophan) can be introduced into the Fc domain of the fusion protein as indicated by doubleunderline above. The amino acid sequence of SEQ ID NO: 71 may optionally be provided with lysine (K) removed from the C-terminus.

The complementary form of Fc fusion polypeptide (SEQ ID NO: 72) is as follows and may optionally be provided with lysine (K) removed from the C-terminus.

```
                                          (SEQ ID NO: 72)
 -13 SNTKVDKRVT GGG

1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVCTLP PSREEMTKNQ VSLSCAVKGF

151 YPSDIAVEWE SNGQPENNYK TTPPVLDSDG SFFLVSKLTV DKSRWQQGNV

201 FSCSVMHEAL HNHYTQKSLS LSPGK
```

To guide heterodimer formation with the polypeptide of SEQ ID NOs: 71 above, four amino acid substitutions can be introduced into the Fc polypeptide as indicated by doubleunderline above. The amino acid sequence of SEQ ID NO: 72 may optionally be provided with lysine (K) removed from the C-terminus.

The proteins of SEQ ID NO: 71 and SEQ ID NO: 72 may be co-expressed and purified from a CHO cell line, to give rise to a heteromeric complex comprising WFIKKN2-Fc.

The present disclosure provides for expression of follistatin-related polypeptides in cells with, for example, one of the following leader sequences:

```
Native human follistatin leader:
                           (SEQ ID NO: 61)
MVRARHQPGGLCLLLLLLCQFMEDRSAQA Native human FLRG leader:
                           (SEQ ID NO: 62)
MRPGAPGPLWPLPWGALAWAVGFVSS Native human WFIKKN1 leader:
                           (SEQ ID NO: 63)
MPALRPLLPLLLLLRLTSG Native human WFIKKN2 leader:
                           (SEQ ID NO: 64)
MWAPRCRRFWSRWEQVAALLLLLLLLGVPPRSLA Tissue plasminogen activator (TPA):
                           (SEQ ID NO: 65)
MDAMKRGLCCVLLLCGAVFVSP Honey bee melittin (HBML):
                           (SEQ ID NO: 66)
MKFLVNVALVFMVVYISYIYA
```

Selected follistatin-related polypeptide variants incorporate the TPA leader and are fused to a G1Fc domain (SEQ ID NO: 39, 40, 41, 42, 43, 44, 45, or 46) with or without an optional linker to form a long chain. A short chain comprising a complementary G1Fc domain (SEQ ID NO: 39, 40, 41, 42, 43, 44, 45, or 46) that promotes pairing with the long chain also incorporates the TPA leader. Constructs were coexpressed in COS or CHO cells and purified from conditioned media by filtration and protein A chromatography. Purity of samples for reporter gene assays was evaluated by SDS-PAGE and Western blot analysis.

Two variants incorporating native full-length human WFIKKN2 polypeptide were generated for direct comparison with the single-arm WFIKKN2-hG1Fc fusion protein produced by coexpression. The first variant was a dual-arm WFIKKN2-hG1Fc fusion protein and the second variant was a single-chain WFIKKN2 polypeptide attached at its C-terminus to a His6 tag (SEQ ID NO: 77).

Applicants transiently transfected COS cells with constructs encoding single-arm WFIKKN2-hG1Fc and dual-arm WFIKKN2-hG1Fc. CHO cells were used to stably express WFIKKN2-His6 ("His6" disclosed as SEQ ID NO: 77). A UCOE™-based construct encoding WFIKKN2-His6 ("His6" disclosed as SEQ ID NO: 77) was stably transfected into a CHO cell line, clones were selected with methotrexate, and any clones that formed colonies were then pooled. No gene amplification was performed since it is difficult to amplify UCOE™ pools while maintaining stability of expression. Instead of dilution cloning, high-expressing pools were identified and used for generating WFIKKN2-His6 ("His6" disclosed as SEQ ID NO: 77).

Purification of Fc-containing constructs was achieved with a variety of techniques, including, for example, filtration of conditioned media, followed by protein A chromatography, elution with glycine buffer (pH 3.0), sample neutralization, and size-exclusion chromatography. Purity of Fc-containing constructs was evaluated by analytical size-exclusion chromatography and SDS-PAGE.

Purification of WFIKKN2-His6 ("His6" disclosed as SEQ ID NO: 77) was achieved using a variety of techniques, including, for example, diafiltration of conditioned media, followed by nickel-nitrilotriacetic acid (Qiagen) agarose affinity chromatography, elution with imidazole buffer, and dialysis against PBS. Purity of samples was evaluated for all constructs by analytical size-exclusion chromatography and SDS-PAGE. Analysis of mature protein confirmed the expected N-terminal sequence for WFIKKN2-His6 ("His6" disclosed as SEQ ID NO: 77).

Example 2. Potency of a Single-Arm WFIKKN2 Polypeptide Fusion Protein

A reporter gene assay in A204 rhabdomyosarcoma cells was used to evaluate the ability of full-length human WFIKKN2 polypeptide variants to inhibit myostatin signaling. This assay is based on a human rhabdomyosarcoma cell line transfected with a pGL3(CAGA)12 reporter plasmid [Dennler et al (1998) EMBO 17:3091-3100] as well as a control Renilla reporter plasmid (pRL-CMV) to normalize for transfection efficiency. The CAGA12 motif is present in TGFβ-responsive genes such as plasminogen activator inhibitor type 1, so this vector is of general use for factors signaling through Smad2 and Smad3.

On the first day of the assay, A204 cells (ATCC® HTB-82) were distributed in 48-well plates at $10^5$ cells per well and incubated overnight in McCoy's 5A growth medium (Life Technologies) supplemented with 10% FBS. All incubations were at 37° C. with 5% CO2 unless otherwise noted. On the second day, a solution containing 10 μg pGL3 (CAGA)12, 0.1 μg pRL-CMV, 30 μl X-tremeGENE 9 (Roche Diagnostics), and 970 μl OptiMEM (Life Technologies) was incubated for 30 minutes at room temperature prior to adding to assay buffer (McCoy's 5A medium+0.1% bovine serum albumin) and applying to the plated cells (500 μl/well) for an overnight incubation. On the third day, medium was removed, and cells were incubated for 6 h with a mixture of ligands and inhibitors prepared as described below.

To evaluate the ability of WFIKKN2 constructs to inhibit myostatin signaling, a serial dilution of each test article (two replicates each) was made in a 48-well plate in assay buffer to a final volume of 200 μl. An equal volume of myostatin (R&D Systems, final concentration of 32 ng/ml) in assay buffer was then added. The test solutions were incubated for 30 minutes prior to adding 250 μl of this mixture to each well of the 48-well plate of transfected A204 cells. After incubation with test solutions for 6 h, cells were rinsed with phosphate-buffered saline, then lysed with passive lysis buffer (Promega E1941) and stored overnight at −70° C. On the fourth and final day, the plates were warmed to room temperature with gentle shaking. Cell lysates were transferred to a 96-well chemiluminescence plate and analyzed in a luminometer with reagents from a Dual-Luciferase Reporter Assay system (Promega E1980). The luciferase activity of the experimental reporter was normalized to the luciferase activity obtained with the Renilla control reporter.

WFIKKN2 polypeptide constructs differed markedly in their ability to inhibit signaling by myostatin. As shown in the table below, single-chain WFIKKN2-His6 ("His6" disclosed as SEQ ID NO: 77) and single-arm WFIKKN2-G1Fc potently inhibited myostatin signaling, with $IC_{50}$ values in the low nanomolar range. In contrast, dual-arm WFIKKN2-G1Fc did not show any reduction in myostatin signaling over the range of concentrations tested, which suggests that the $IC_{50}$ value for this construct would be at least 100 nM. Thus, the potency of myostatin inhibition with single-arm WFIKKN2-G1Fc was substantially higher than that of a G1Fc fusion protein comprising dual WFIKKN2 arms.

| Construct | $IC_{50}$ (nM) | Half-life in Mouse (h) |
| --- | --- | --- |
| Single-chain WFIKKN2-His6 ("His6" disclosed as SEQ ID NO: 77) | 1.4 | ~2.5 |
| Single-arm WFIKKN2-G1Fc | 2.9 | ~110 |
| Dual-arm WFIKKN2-G1Fc | >100 | ND |

ND, not determined

Elimination pharmacokinetics of single-chain WFIKKN2-His6 ("His6" disclosed as SEQ ID NO: 77) and single-arm WFIKKN2-G1Fc were studied in separate experiments conducted in mice. Concentrations of single-chain WFIKKN2-His6 ("His6" disclosed as SEQ ID NO: 77) in mouse serum samples after subcutaneous administration of a single dose were measured by ELISA with a commercial anti-His6 ("His6" disclosed as SEQ ID NO: 77) antibody (abcam® ab18184). Concentrations of single-arm WFIKKN2-G1Fc after subcutaneous administration of a single dose were measured by ELISA with a commercial anti-human IgG1 antibody (Binding Site Immunologicals AP006). As indicated in the table above, the half-life of single-chain WFIKKN2-His6 ("His6" disclosed as SEQ ID NO: 77) protein in mice was approximately 2.5 hours (data not shown), whereas the half-life of single-arm WFIKKN2-G1Fc fusion protein in mice (n=3) was more than 100 hours (data not shown), which would predict that this molecule will have a pharmacologically useful serum half-life in humans of 10-20 days. Thus, by utilizing a heterodimeric or asymmetric approach to generating a single-arm WFIKKN2 construct, applicants were able to combine the desirable ligand binding activity of the single chain (native) protein with the desirable serum half-life of a traditional homodimeric Fc fusion protein.

Together, these results indicate that single-arm WFIKKN2-G1Fc could be a useful therapeutic agent. Beyond this example, applicants predict that other asymmetric fusion proteins comprising single-arm follistatin-related polypeptides will also display more potent inhibition of ligand signaling than their dual-arm counterparts while conferring ease of purification and a serum half-life that is typical for a homodimeric Fc fusion protein construct.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those

We claim:

1. A method for treating a muscle-related disorder in a subject in need thereof, comprising administering to the subject a protein complex comprising a first polypeptide covalently or non-covalently associated with a second polypeptide, wherein:
   a. the first polypeptide comprises the amino acid sequence of a follistatin-related polypeptide and the amino acid sequence of a first member of an interaction pair; wherein the follistatin-related polypeptide comprises:
      i) a whey acidic protein domain from a WFIKKN2 polypeptide having an amino acid sequence that is at least 90% identical to SEQ ID NO: 30,
      ii) a follistatin-Kazal domain from a WFIKKN2 polypeptide having an amino acid sequence that is at least 90% identical to SEQ ID NO: 30, and
      iii) an immunoglobulin domain from a WFIKKN2 polypeptide having an amino acid sequence that is at least 90% identical to SEQ ID NO: 30;
   and wherein the follistatin-related polypeptide is capable of binding growth differentiation factor 8 (GDF8); and
   b. the second polypeptide comprises the amino acid sequence of a second member of the interaction pair, and wherein the second polypeptide does not comprise a follistatin-related polypeptide;
   wherein the first member of the interaction pair comprises a constant domain of an immunoglobulin and wherein the second member of the interaction pair comprises a constant domain of an immunoglobulin.

2. The method of claim 1, wherein the amino acid sequence of the follistatin-related polypeptide comprises an amino acid sequence that is at least 95% identical to the amino acid sequence of SEQ ID NO: 31.

3. The method of claim 1, wherein the first polypeptide comprises a linker polypeptide positioned between the amino acid sequence of the follistatin-related polypeptide and the amino acid sequence of the first member of the interaction pair.

4. The method of claim 1, wherein the first member of the interaction pair associates covalently or non-covalently with the second member of the interaction pair to form a dimeric protein complex.

5. The method of claim 1, wherein the interaction pair is an asymmetric interaction pair.

6. The method of claim 5, wherein the first member of the asymmetric interaction pair comprises a first modified constant domain of an IgG and wherein the second member of the asymmetric interaction pair comprises a second modified constant domain of an IgG, and wherein the first and second members of the asymmetric interaction pair associate to form a heterodimeric complex.

7. The method of claim 5, wherein the first member of the asymmetric interaction pair comprises a first modified Fc portion of IgG and wherein the second member of the asymmetric interaction pair comprises a second modified Fc portion of an IgG, and wherein the first and second members of the asymmetric interaction pair associate to form a heterodimeric complex.

8. The method of claim 7, wherein the first Fc portion of an IgG comprises an amino acid sequence that is at least 90% identical to an amino acid sequence selected from the group: SEQ ID NOs 34-46, and wherein the second Fc portion of an IgG comprises an amino acid sequence that is different from the amino acid sequence of the first Fc portion of an IgG and that is at least 90% identical to an amino acid sequence selected from the group SEQ ID NOs 34-46.

9. The method of claim 1, wherein the interaction pair is an unguided interaction pair.

10. The method of claim 9, wherein the first member of the unguided interaction pair associates covalently or non-covalently with the second member of the interaction pair to form a dimeric complex.

11. The method of claim 9, wherein the first member of the unguided interaction pair has the same amino acid sequence as the second member of the unguided interaction pair.

12. The method of claim 1, wherein the second polypeptide comprises the amino acid sequence of a second member of the interaction pair, and wherein the second polypeptide does not comprise any other amino acid sequence that confers a substantial biological activity.

13. The method of claim 1, wherein the second polypeptide consists of the amino acid sequence of a second member of the interaction pair, provided that the second polypeptide may comprise an additional 1-50, 1-40, 1-30, 1-20 or 1-10 amino acids fused to the C-terminus, the N-terminus or both the C- and N-termini of the amino acid sequence of the second member of the interaction pair.

14. The method of claim 13, wherein the additional amino acids confer no substantial biological activity.

15. The method of claim 1, wherein the protein complex binds to one or more ligands selected from: GDF8, GDF11 (growth differentiation factor 11), activin A, activin B, activin C or activin E with a KD (dissociation constant) of greater than or equal to $10^{-9}$, $10^{-10}$, $10^{-11}$, $10^{-12}$.

16. The method of claim 1, wherein the protein complex inhibits in a cell-based assay signaling by one or more ligands selected from: GDF8, GDF11 (growth differentiation factor 11), activin A, activin B, activin C or activin E.

17. The method of claim 1, wherein the protein complex exhibits a serum half-life in a mouse of at least 6, 12, 24, 36, 48 or 72 hours.

18. The method of claim 1, wherein the protein complex exhibits a serum half-life in a human of at least 6, 8, 10, or 12 days.

19. The method of claim 1, wherein the protein complex is a heterodimer.

20. The method of claim 1, wherein the amino acid sequence of the follistatin-related polypeptide comprises an amino acid sequence that is identical to the amino acid sequence of SEQ ID NO: 31.

21. The method of claim 1, wherein each member of the asymmetric interaction pair comprises a different amino acid sequence selected from the group consisting of amino acid sequences that are each at least 95% identical to any of SEQ ID NOs: 34-46.

22. The method of claim 1, wherein:
  a. the first polypeptide comprises an amino acid sequence that is at least 90% identical to the amino acid sequence of SEQ ID NO: 57; and
  b. the second polypeptide comprises an amino acid sequence that is at least 90% identical to the amino acid sequence of SEQ ID NO: 58.

23. The method of claim 1, wherein:
  a. the first polypeptide comprises an amino acid sequence that is at least 90% identical to the amino acid sequence of SEQ ID NO: 71; and
  b. the second polypeptide comprises an amino acid sequence that is at least 90% identical to the amino acid sequence of SEQ ID NO: 72.

24. The method of claim 1, wherein the follistatin-related polypeptide comprises:
  i) a whey acidic protein domain from a WFIKKN2 polypeptide having an amino acid sequence that is at least 95% identical to SEQ ID NO: 30,
  ii) a follistatin-Kazal domain from a WFIKKN2 polypeptide having an amino acid sequence that is at least 95% identical to SEQ ID NO: 30, and
  iii) an immunoglobulin domain from a WFIKKN2 polypeptide having an amino acid sequence that is at least 95% identical to SEQ ID NO: 30.

25. The method of claim 1, wherein the follistatin-related polypeptide comprises:
  i) a whey acidic protein domain from a WFIKKN2 polypeptide having the amino acid sequence of SEQ ID NO: 30,
  ii) a follistatin-Kazal domain from a WFIKKN2 polypeptide having the amino acid sequence of SEQ ID NO: 30, and
  iii) an immunoglobulin domain from a WFIKKN2 polypeptide having the amino acid sequence of SEQ ID NO: 30.

26. The method of claim 1, wherein the subject has a muscular dystrophy.

27. The method of claim 26, wherein the muscular dystrophy is selected from the group consisting of: Duchenne muscular dystrophy (DMD), Becker muscular dystrophy (BMD), Emery-Dreifuss muscular dystrophy (EDMD), limb-girdle muscular dystrophy (LGMD), facioscapulohumeral muscular dystrophy (FSHD), myotonic mystrophy (MMD), oculopharyngeal muscular dystrophy (OPMD), distal muscular dystrophy (DD), and congenital muscular dystrophy (CMD).

28. The method of claim 1, wherein the subject has amyotrophic lateral sclerosis.

* * * * *

SEQUENCE LISTING

<160> NUMBER OF SEQ ID NOS: 77

<210> SEQ ID NO 1
<211> LENGTH: 317
<212> TYPE: PRT
<213> ORGANISM: Homo sapiens

<400> SEQUENCE: 1

Met Val Arg Ala Arg His Gln Pro Gly Gly Leu Cys Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
            130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
            195                 200                 205

Asn Asp Gly Val Thr Tyr Ser Ser Ala Cys His Leu Arg Lys Ala Thr
            210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
            245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
            290                 295                 300

Gly Val Leu Leu Glu Val Lys His Ser Gly Ser Cys Asn
305                 310                 315

<210> SEQ ID NO 2

```
<211> LENGTH: 288
<212> TYPE: PRT
<213> ORGANISM: Homo sapiens

<400> SEQUENCE: 2

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

<210> SEQ ID NO 3
<211> LENGTH: 344
<212> TYPE: PRT
<213> ORGANISM: Homo sapiens

<400> SEQUENCE: 3

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60
```

Trp Thr Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
            195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
                260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
            290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp
            340

<210> SEQ ID NO 4
<211> LENGTH: 315
<212> TYPE: PRT
<213> ORGANISM: Homo sapiens

<400> SEQUENCE: 4

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
                20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
            50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile

```
                    85                  90                  95
Thr Trp Lys Gly Pro Val Cys Gly Leu Asp Gly Lys Thr Tyr Arg Asn
                100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
        130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
        210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Glu Glu Glu Asp Glu Asp Gln Asp
        290                 295                 300

Tyr Ser Phe Pro Ile Ser Ser Ile Leu Glu Trp
305                 310                 315

<210> SEQ ID NO 5
<211> LENGTH: 65
<212> TYPE: PRT
<213> ORGANISM: Homo sapiens

<400> SEQUENCE: 5

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr
65

<210> SEQ ID NO 6
<211> LENGTH: 63
<212> TYPE: PRT
<213> ORGANISM: Homo sapiens

<400> SEQUENCE: 6

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
```

20                  25                  30
Ser Trp Thr Glu Glu Asp Val Asn Asp Asn Thr Leu Phe Lys Trp Met
            35                  40                  45
Ile Phe Asn Gly Gly Ala Pro Asn Cys Ile Pro Cys Lys Glu Thr
        50                  55                  60

<210> SEQ ID NO 7
<211> LENGTH: 70
<212> TYPE: PRT
<213> ORGANISM: Homo sapiens

<400> SEQUENCE: 7

Cys Glu Asn Val Asp Cys Gly Pro Gly Lys Lys Cys Arg Met Asn Lys
1               5                   10                  15

Lys Asn Lys Pro Arg Cys Val Cys Ala Pro Asp Cys Ser Asn Ile Thr
                20                  25                  30

Trp Lys Gly Pro Val Cys Gly Leu Asp Gly Lys Thr Tyr Arg Asn Glu
            35                  40                  45

Cys Ala Leu Leu Lys Ala Arg Cys Lys Glu Gln Pro Glu Leu Glu Val
        50                  55                  60

Gln Tyr Gln Gly Arg Cys
65                  70

<210> SEQ ID NO 8
<211> LENGTH: 72
<212> TYPE: PRT
<213> ORGANISM: Homo sapiens

<400> SEQUENCE: 8

Cys Arg Asp Val Phe Cys Pro Gly Ser Ser Thr Cys Val Val Asp Gln
1               5                   10                  15

Thr Asn Asn Ala Tyr Cys Val Thr Cys Asn Arg Ile Cys Pro Glu Pro
                20                  25                  30

Ala Ser Ser Glu Gln Tyr Leu Cys Gly Asn Asp Gly Val Thr Tyr Ser
            35                  40                  45

Ser Ala Cys His Leu Arg Lys Ala Thr Cys Leu Leu Gly Arg Ser Ile
        50                  55                  60

Gly Leu Ala Tyr Glu Gly Lys Cys
65                  70

<210> SEQ ID NO 9
<211> LENGTH: 72
<212> TYPE: PRT
<213> ORGANISM: Homo sapiens

<400> SEQUENCE: 9

Cys Glu Asp Ile Gln Cys Thr Gly Gly Lys Lys Cys Leu Trp Asp Phe
1               5                   10                  15

Lys Val Gly Arg Gly Arg Cys Ser Leu Cys Asp Glu Leu Cys Pro Asp
                20                  25                  30

Ser Lys Ser Asp Glu Pro Val Cys Ala Ser Asp Asn Ala Thr Tyr Ala
            35                  40                  45

Ser Glu Cys Ala Met Lys Glu Ala Ala Cys Ser Ser Gly Val Leu Leu
        50                  55                  60

Glu Val Lys His Ser Gly Ser Cys
65                  70

<210> SEQ ID NO 10

<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys
        130

<210> SEQ ID NO 11
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Cys Glu Asn Val Asp Cys Gly Pro Gly Lys Lys
        130                 135                 140

Cys Arg Met Asn Lys Lys Asn Lys Pro Arg Cys Val Cys Ala Pro Asp
145                 150                 155                 160

Cys Ser Asn Ile Thr Trp Lys Gly Pro Val Cys Gly Leu Asp Gly Lys
            165                 170                 175

```
Thr Tyr Arg Asn Glu Cys Ala Leu Leu Lys Ala Arg Cys Lys Glu Gln
            180                 185                 190

Pro Glu Leu Glu Val Gln Tyr Gln Gly Arg Cys
        195                 200

<210> SEQ ID NO 12
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Cys Glu Asn Val Asp Cys Gly Pro Gly Lys Lys Cys Arg Met Asn Lys
1               5                   10                  15

Lys Asn Lys Pro Arg Cys Val Cys Ala Pro Asp Cys Ser Asn Ile Thr
            20                  25                  30

Trp Lys Gly Pro Val Cys Gly Leu Asp Gly Lys Thr Tyr Arg Asn Glu
        35                  40                  45

Cys Ala Leu Leu Lys Ala Arg Cys Lys Glu Gln Pro Glu Leu Glu Val
    50                  55                  60

Gln Tyr Gln Gly Arg Cys Cys Arg Asp Val Phe Cys Pro Gly Ser Ser
65                  70                  75                  80

Thr Cys Val Val Asp Gln Thr Asn Asn Ala Tyr Cys Val Thr Cys Asn
                85                  90                  95

Arg Ile Cys Pro Glu Pro Ala Ser Ser Glu Gln Tyr Leu Cys Gly Asn
            100                 105                 110

Asp Gly Val Thr Tyr Ser Ser Ala Cys His Leu Arg Lys Ala Thr Cys
        115                 120                 125

Leu Leu Gly Arg Ser Ile Gly Leu Ala Tyr Glu Gly Lys Cys
    130                 135                 140

<210> SEQ ID NO 13
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Cys Glu Asn Val Asp Cys Gly Pro Gly Lys Lys Cys Arg Met Asn Lys
1               5                   10                  15

Lys Asn Lys Pro Arg Cys Val Cys Ala Pro Asp Cys Ser Asn Ile Thr
            20                  25                  30

Trp Lys Gly Pro Val Cys Gly Leu Asp Gly Lys Thr Tyr Arg Asn Glu
        35                  40                  45

Cys Ala Leu Leu Lys Ala Arg Cys Lys Glu Gln Pro Glu Leu Glu Val
    50                  55                  60

Gln Tyr Gln Gly Arg Cys Cys Arg Asp Val Phe Cys Pro Gly Ser Ser
65                  70                  75                  80

Thr Cys Val Val Asp Gln Thr Asn Asn Ala Tyr Cys Val Thr Cys Asn
                85                  90                  95

Arg Ile Cys Pro Glu Pro Ala Ser Ser Glu Gln Tyr Leu Cys Gly Asn
            100                 105                 110

Asp Gly Val Thr Tyr Ser Ser Ala Cys His Leu Arg Lys Ala Thr Cys
        115                 120                 125
```

```
Leu Leu Gly Arg Ser Ile Gly Leu Ala Tyr Glu Gly Lys Cys Cys Glu
    130                 135                 140

Asp Ile Gln Cys Thr Gly Lys Lys Cys Leu Trp Asp Phe Lys Val
145                 150                 155                 160

Gly Arg Gly Arg Cys Ser Leu Cys Asp Glu Leu Cys Pro Asp Ser Lys
                165                 170                 175

Ser Asp Glu Pro Val Cys Ala Ser Asp Asn Ala Thr Tyr Ala Ser Glu
            180                 185                 190

Cys Ala Met Lys Glu Ala Ala Cys Ser Ser Gly Val Leu Leu Glu Val
        195                 200                 205

Lys His Ser Gly Ser Cys
    210

<210> SEQ ID NO 14
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
            20                  25                  30

Ser Trp Thr Glu Glu Asp Val Asn Asp Asn Thr Leu Phe Lys Trp Met
        35                  40                  45

Ile Phe Asn Gly Gly Ala Pro Asn Cys Ile Pro Cys Lys Glu Thr Cys
    50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
            100                 105                 110

Ala Leu Leu Lys Ala Arg Cys Lys Glu Gln Pro Glu Leu Glu Val Gln
        115                 120                 125

Tyr Gln Gly Arg Cys Cys Arg Asp Val Phe Cys Pro Gly Ser Ser Thr
    130                 135                 140

Cys Val Val Asp Gln Thr Asn Asn Ala Tyr Cys Val Thr Cys Asn Arg
145                 150                 155                 160

Ile Cys Pro Glu Pro Ala Ser Ser Glu Gln Tyr Leu Cys Gly Asn Asp
                165                 170                 175

Gly Val Thr Tyr Ser Ser Ala Cys His Leu Arg Lys Ala Thr Cys Leu
            180                 185                 190

Leu Gly Arg Ser Ile Gly Leu Ala Tyr Glu Gly Lys Cys
        195                 200                 205

<210> SEQ ID NO 15
<211> LENGTH: 320
<212> TYPE: PRT
<213> ORGANISM: Homo sapiens

<400> SEQUENCE: 15

Met Val Arg Ala Arg His Gln Pro Gly Gly Leu Cys Leu Leu Leu Leu
1               5                   10                  15
```

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

<210> SEQ ID NO 16
<211> LENGTH: 291
<212> TYPE: PRT
<213> ORGANISM: Homo sapiens

<400> SEQUENCE: 16

Gly Asn Cys Trp Leu Arg Gln Ala Lys Asn Gly Arg Cys Gln Val Leu
1               5                   10                  15

Tyr Lys Thr Glu Leu Ser Lys Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn

```
                65                  70                  75                  80
Lys Lys Asn Lys Pro Arg Cys Val Cys Ala Pro Asp Cys Ser Asn Ile
                    85                  90                  95

Thr Trp Lys Gly Pro Val Cys Gly Leu Asp Gly Lys Thr Tyr Arg Asn
                100                 105                 110

Glu Cys Ala Leu Leu Lys Ala Arg Cys Lys Glu Gln Pro Glu Leu Glu
                115                 120                 125

Val Gln Tyr Gln Gly Arg Cys Lys Lys Thr Cys Arg Asp Val Phe Cys
            130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
                180                 185                 190

Lys Ala Thr Cys Leu Leu Gly Arg Ser Ile Gly Leu Ala Tyr Glu Gly
                195                 200                 205

Lys Cys Ile Lys Ala Lys Ser Cys Glu Asp Ile Gln Cys Thr Gly Gly
            210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
                260                 265                 270

Cys Ser Ser Gly Val Leu Leu Glu Val Lys His Ser Gly Ser Cys Asn
                275                 280                 285

Ser Ile Ser
        290

<210> SEQ ID NO 17
<211> LENGTH: 289
<212> TYPE: PRT
<213> ORGANISM: Homo sapiens

<400> SEQUENCE: 17

Cys Trp Leu Arg Gln Ala Lys Asn Gly Arg Cys Gln Val Leu Tyr Lys
1               5                   10                  15

Thr Glu Leu Ser Lys Glu Glu Cys Cys Ser Thr Gly Arg Leu Ser Thr
                20                  25                  30

Ser Trp Thr Glu Glu Asp Val Asn Asp Asn Thr Leu Phe Lys Trp Met
            35                  40                  45

Ile Phe Asn Gly Gly Ala Pro Asn Cys Ile Pro Cys Lys Glu Thr Cys
        50                  55                  60

Glu Asn Val Asp Cys Gly Pro Gly Lys Lys Cys Arg Met Asn Lys Lys
65                  70                  75                  80

Asn Lys Pro Arg Cys Val Cys Ala Pro Asp Cys Ser Asn Ile Thr Trp
                85                  90                  95

Lys Gly Pro Val Cys Gly Leu Asp Gly Lys Thr Tyr Arg Asn Glu Cys
                100                 105                 110

Ala Leu Leu Lys Ala Arg Cys Lys Glu Gln Pro Glu Leu Glu Val Gln
            115                 120                 125

Tyr Gln Gly Arg Cys Lys Lys Thr Cys Arg Asp Val Phe Cys Pro Gly
        130                 135                 140
```

Ser Ser Thr Cys Val Val Asp Gln Thr Asn Asn Ala Tyr Cys Val Thr
145                 150                 155                 160

Cys Asn Arg Ile Cys Pro Glu Pro Ala Ser Ser Glu Gln Tyr Leu Cys
            165                 170                 175

Gly Asn Asp Gly Val Thr Tyr Ser Ser Ala Cys His Leu Arg Lys Ala
            180                 185                 190

Thr Cys Leu Leu Gly Arg Ser Ile Gly Leu Ala Tyr Glu Gly Lys Cys
        195                 200                 205

Ile Lys Ala Lys Ser Cys Glu Asp Ile Gln Cys Thr Gly Gly Lys Lys
        210                 215                 220

Cys Leu Trp Asp Phe Lys Val Gly Arg Gly Arg Cys Ser Leu Cys Asp
225                 230                 235                 240

Glu Leu Cys Pro Asp Ser Lys Ser Asp Glu Pro Val Cys Ala Ser Asp
            245                 250                 255

Asn Ala Thr Tyr Ala Ser Glu Cys Ala Met Lys Glu Ala Ala Cys Ser
            260                 265                 270

Ser Gly Val Leu Leu Glu Val Lys His Ser Gly Ser Cys Asn Ser Ile
        275                 280                 285

Ser

<210> SEQ ID NO 18
<211> LENGTH: 263
<212> TYPE: PRT
<213> ORGANISM: Homo sapiens

<400> SEQUENCE: 18

Met Arg Pro Gly Ala Pro Gly Pro Leu Trp Pro Leu Pro Trp Gly Ala
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
            165                 170                 175

Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
        195                 200                 205

Glu Leu Cys Gly Asn Asn Asn Val Thr Tyr Ile Ser Ser Cys His Met
210                 215                 220

```
Arg Gln Ala Thr Cys Phe Leu Gly Arg Ser Ile Gly Val Arg His Ala
225                 230                 235                 240

Gly Ser Cys Ala Gly Thr Pro Glu Glu Pro Pro Gly Gly Glu Ser Ala
            245                 250                 255

Glu Glu Glu Glu Asn Phe Val
            260
```

<210> SEQ ID NO 19
<211> LENGTH: 226
<212> TYPE: PRT
<213> ORGANISM: Homo sapiens

<400> SEQUENCE: 19

```
Cys Trp Leu Gln Gln Gly Gln Glu Ala Thr Cys Ser Leu Val Leu Gln
1               5                   10                  15

Thr Asp Val Thr Arg Ala Glu Cys Cys Ala Ser Gly Asn Ile Asp Thr
            20                  25                  30

Ala Trp Ser Asn Leu Thr His Pro Gly Asn Lys Ile Asn Leu Leu Gly
        35                  40                  45

Phe Leu Gly Leu Val His Cys Leu Pro Cys Lys Asp Ser Cys Asp Gly
50                  55                  60

Val Glu Cys Gly Pro Gly Lys Ala Cys Arg Met Leu Gly Gly Arg Pro
65                  70                  75                  80

Arg Cys Glu Cys Ala Pro Asp Cys Ser Gly Leu Pro Ala Arg Leu Gln
                85                  90                  95

Val Cys Gly Ser Asp Gly Ala Thr Tyr Arg Asp Glu Cys Glu Leu Arg
            100                 105                 110

Ala Ala Arg Cys Arg Gly His Pro Asp Leu Ser Val Met Tyr Arg Gly
        115                 120                 125

Arg Cys Arg Lys Ser Cys Glu His Val Val Cys Pro Arg Pro Gln Ser
130                 135                 140

Cys Val Val Asp Gln Thr Gly Ser Ala His Cys Val Val Cys Arg Ala
145                 150                 155                 160

Ala Pro Cys Pro Val Pro Ser Ser Pro Gly Gln Glu Leu Cys Gly Asn
                165                 170                 175

Asn Asn Val Thr Tyr Ile Ser Ser Cys His Met Arg Gln Ala Thr Cys
            180                 185                 190

Phe Leu Gly Arg Ser Ile Gly Val Arg His Ala Gly Ser Cys Ala Gly
        195                 200                 205

Thr Pro Glu Glu Pro Pro Gly Gly Glu Ser Ala Glu Glu Glu Glu Asn
210                 215                 220

Phe Val
225
```

<210> SEQ ID NO 20
<211> LENGTH: 60
<212> TYPE: PRT
<213> ORGANISM: Homo sapiens

<400> SEQUENCE: 20

```
Gly Val Cys Trp Leu Gln Gln Gly Gln Glu Ala Thr Cys Ser Leu Val
1               5                   10                  15

Leu Gln Thr Asp Val Thr Arg Ala Glu Cys Cys Ala Ser Gly Asn Ile
            20                  25                  30

Asp Thr Ala Trp Ser Asn Leu Thr His Pro Gly Asn Lys Ile Asn Leu
        35                  40                  45
```

Leu Gly Phe Leu Gly Leu Val His Cys Leu Pro Cys
    50                  55                  60

<210> SEQ ID NO 21
<211> LENGTH: 58
<212> TYPE: PRT
<213> ORGANISM: Homo sapiens

<400> SEQUENCE: 21

Cys Trp Leu Gln Gln Gly Gln Glu Ala Thr Cys Ser Leu Val Leu Gln
1               5                   10                  15

Thr Asp Val Thr Arg Ala Glu Cys Cys Ala Ser Gly Asn Ile Asp Thr
            20                  25                  30

Ala Trp Ser Asn Leu Thr His Pro Gly Asn Lys Ile Asn Leu Leu Gly
        35                  40                  45

Phe Leu Gly Leu Val His Cys Leu Pro Cys
    50                  55

<210> SEQ ID NO 22
<211> LENGTH: 69
<212> TYPE: PRT
<213> ORGANISM: Homo sapiens

<400> SEQUENCE: 22

Cys Asp Gly Val Glu Cys Gly Pro Gly Lys Ala Cys Arg Met Leu Gly
1               5                   10                  15

Gly Arg Pro Arg Cys Glu Cys Ala Pro Asp Cys Ser Gly Leu Pro Ala
            20                  25                  30

Arg Leu Gln Val Cys Gly Ser Asp Gly Ala Thr Tyr Arg Asp Glu Cys
        35                  40                  45

Glu Leu Arg Ala Ala Arg Cys Arg Gly His Pro Asp Leu Ser Val Met
    50                  55                  60

Tyr Arg Gly Arg Cys
65

<210> SEQ ID NO 23
<211> LENGTH: 73
<212> TYPE: PRT
<213> ORGANISM: Homo sapiens

<400> SEQUENCE: 23

Cys Glu His Val Val Cys Pro Arg Pro Gln Ser Cys Val Val Asp Gln
1               5                   10                  15

Thr Gly Ser Ala His Cys Val Cys Arg Ala Ala Pro Cys Pro Val
            20                  25                  30

Pro Ser Ser Pro Gly Gln Glu Leu Cys Gly Asn Asn Asn Val Thr Tyr
        35                  40                  45

Ile Ser Ser Cys His Met Arg Gln Ala Thr Cys Phe Leu Gly Arg Ser
    50                  55                  60

Ile Gly Val Arg His Ala Gly Ser Cys
65                  70

<210> SEQ ID NO 24
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Gly Val Cys Trp Leu Gln Gln Gly Gln Glu Ala Thr Cys Ser Leu Val
1               5                   10                  15

Leu Gln Thr Asp Val Thr Arg Ala Glu Cys Cys Ala Ser Gly Asn Ile
            20                  25                  30

Asp Thr Ala Trp Ser Asn Leu Thr His Pro Gly Asn Lys Ile Asn Leu
            35                  40                  45

Leu Gly Phe Leu Gly Leu Val His Cys Leu Pro Cys Lys Cys Asp Gly
            50                  55                  60

Val Glu Cys Gly Pro Gly Lys Ala Cys Arg Met Leu Gly Gly Arg Pro
65                  70                  75                  80

Arg Cys Glu Cys Ala Pro Asp Cys Ser Gly Leu Pro Ala Arg Leu Gln
            85                  90                  95

Val Cys Gly Ser Asp Gly Ala Thr Tyr Arg Asp Glu Cys Glu Leu Arg
            100                 105                 110

Ala Ala Arg Cys Arg Gly His Pro Asp Leu Ser Val Met Tyr Arg Gly
            115                 120                 125

Arg Cys
    130

<210> SEQ ID NO 25
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Val Cys Trp Leu Gln Gln Gly Gln Glu Ala Thr Cys Ser Leu Val
1               5                   10                  15

Leu Gln Thr Asp Val Thr Arg Ala Glu Cys Cys Ala Ser Gly Asn Ile
            20                  25                  30

Asp Thr Ala Trp Ser Asn Leu Thr His Pro Gly Asn Lys Ile Asn Leu
            35                  40                  45

Leu Gly Phe Leu Gly Leu Val His Cys Leu Pro Cys Lys Cys Asp Gly
            50                  55                  60

Val Glu Cys Gly Pro Gly Lys Ala Cys Arg Met Leu Gly Gly Arg Pro
65                  70                  75                  80

Arg Cys Glu Cys Ala Pro Asp Cys Ser Gly Leu Pro Ala Arg Leu Gln
            85                  90                  95

Val Cys Gly Ser Asp Gly Ala Thr Tyr Arg Asp Glu Cys Glu Leu Arg
            100                 105                 110

Ala Ala Arg Cys Arg Gly His Pro Asp Leu Ser Val Met Tyr Arg Gly
            115                 120                 125

Arg Cys Cys Glu His Val Val Cys Pro Arg Pro Gln Ser Cys Val Val
    130                 135                 140

Asp Gln Thr Gly Ser Ala His Cys Val Val Cys Arg Ala Ala Pro Cys
145                 150                 155                 160

Pro Val Pro Ser Ser Pro Gly Gln Glu Leu Cys Gly Asn Asn Asn Val
                165                 170                 175

Thr Tyr Ile Ser Ser Cys His Met Arg Gln Ala Thr Cys Phe Leu Gly
            180                 185                 190

Arg Ser Ile Gly Val Arg His Ala Gly Ser Cys
            195                 200
```

<210> SEQ ID NO 26
<211> LENGTH: 548
<212> TYPE: PRT
<213> ORGANISM: Homo sapiens

<400> SEQUENCE: 26

```
Met Pro Ala Leu Arg Pro Leu Leu Pro Leu Leu Leu Leu Leu Arg Leu
1               5                   10                  15

Thr Ser Gly Ala Gly Leu Leu Pro Gly Leu Gly Ser His Pro Gly Val
            20                  25                  30

Cys Pro Asn Gln Leu Ser Pro Asn Leu Trp Val Asp Ala Gln Ser Thr
        35                  40                  45

Cys Glu Arg Glu Cys Ser Arg Asp Gln Asp Cys Ala Ala Ala Glu Lys
    50                  55                  60

Cys Cys Ile Asn Val Cys Gly Leu His Ser Cys Val Ala Ala Arg Phe
65                  70                  75                  80

Pro Gly Ser Pro Ala Ala Pro Thr Thr Ala Ala Ser Cys Glu Gly Phe
                85                  90                  95

Val Cys Pro Gln Gln Gly Ser Asp Cys Asp Ile Trp Asp Gly Gln Pro
            100                 105                 110

Val Cys Arg Cys Arg Asp Arg Cys Glu Lys Glu Pro Ser Phe Thr Cys
        115                 120                 125

Ala Ser Asp Gly Leu Thr Tyr Tyr Asn Arg Cys Tyr Met Asp Ala Glu
    130                 135                 140

Ala Cys Leu Arg Gly Leu His Leu His Ile Val Pro Cys Lys His Val
145                 150                 155                 160

Leu Ser Trp Pro Pro Ser Ser Pro Gly Pro Pro Glu Thr Thr Ala Arg
                165                 170                 175

Pro Thr Pro Gly Ala Ala Pro Val Pro Pro Ala Leu Tyr Ser Ser Pro
            180                 185                 190

Ser Pro Gln Ala Val Gln Val Gly Gly Thr Ala Ser Leu His Cys Asp
        195                 200                 205

Val Ser Gly Arg Pro Pro Pro Ala Val Thr Trp Glu Lys Gln Ser His
    210                 215                 220

Gln Arg Glu Asn Leu Ile Met Arg Pro Asp Gln Met Tyr Gly Asn Val
225                 230                 235                 240

Val Val Thr Ser Ile Gly Gln Leu Val Leu Tyr Asn Ala Arg Pro Glu
                245                 250                 255

Asp Ala Gly Leu Tyr Thr Cys Thr Ala Arg Asn Ala Ala Gly Leu Leu
            260                 265                 270

Arg Ala Asp Phe Pro Leu Ser Val Val Gln Arg Glu Pro Ala Arg Asp
        275                 280                 285

Ala Ala Pro Ser Ile Pro Ala Pro Ala Glu Cys Leu Pro Asp Val Gln
    290                 295                 300

Ala Cys Thr Gly Pro Thr Ser Pro His Leu Val Leu Trp His Tyr Asp
305                 310                 315                 320

Pro Gln Arg Gly Gly Cys Met Thr Phe Pro Ala Arg Gly Cys Asp Gly
                325                 330                 335

Ala Ala Arg Gly Phe Glu Thr Tyr Glu Ala Cys Gln Gln Ala Cys Ala
            340                 345                 350

Arg Gly Pro Gly Asp Ala Cys Val Leu Pro Ala Val Gln Gly Pro Cys
        355                 360                 365

Arg Gly Trp Glu Pro Arg Trp Ala Tyr Ser Pro Leu Leu Gln Gln Cys
    370                 375                 380
```

```
His Pro Phe Val Tyr Gly Gly Cys Glu Gly Asn Gly Asn Asn Phe His
385                 390                 395                 400

Ser Arg Glu Ser Cys Glu Asp Ala Cys Pro Val Pro Arg Thr Pro Pro
            405                 410                 415

Cys Arg Ala Cys Arg Leu Arg Ser Lys Leu Ala Leu Ser Leu Cys Arg
            420                 425                 430

Ser Asp Phe Ala Ile Val Gly Arg Leu Thr Glu Val Leu Glu Glu Pro
        435                 440                 445

Glu Ala Ala Gly Gly Ile Ala Arg Val Ala Leu Glu Asp Val Leu Lys
    450                 455                 460

Asp Asp Lys Met Gly Leu Lys Phe Leu Gly Thr Lys Tyr Leu Glu Val
465                 470                 475                 480

Thr Leu Ser Gly Met Asp Trp Ala Cys Pro Cys Pro Asn Met Thr Ala
                485                 490                 495

Gly Asp Gly Pro Leu Val Ile Met Gly Glu Val Arg Asp Gly Val Ala
            500                 505                 510

Val Leu Asp Ala Gly Ser Tyr Val Arg Ala Ala Ser Glu Lys Arg Val
        515                 520                 525

Lys Lys Ile Leu Glu Leu Leu Glu Lys Gln Ala Cys Glu Leu Leu Asn
    530                 535                 540

Arg Phe Gln Asp
545

<210> SEQ ID NO 27
<211> LENGTH: 529
<212> TYPE: PRT
<213> ORGANISM: Homo sapiens

<400> SEQUENCE: 27

Ala Gly Leu Leu Pro Gly Leu Gly Ser His Pro Gly Val Cys Pro Asn
1               5                   10                  15

Gln Leu Ser Pro Asn Leu Trp Val Asp Ala Gln Ser Thr Cys Glu Arg
            20                  25                  30

Glu Cys Ser Arg Asp Gln Asp Cys Ala Ala Glu Lys Cys Cys Ile
        35                  40                  45

Asn Val Cys Gly Leu His Ser Cys Val Ala Ala Arg Phe Pro Gly Ser
    50                  55                  60

Pro Ala Ala Pro Thr Thr Ala Ser Cys Glu Gly Phe Val Cys Pro
65                  70                  75                  80

Gln Gln Gly Ser Asp Cys Asp Ile Trp Asp Gly Gln Pro Val Cys Arg
                85                  90                  95

Cys Arg Asp Arg Cys Glu Lys Glu Pro Ser Phe Thr Cys Ala Ser Asp
            100                 105                 110

Gly Leu Thr Tyr Tyr Asn Arg Cys Tyr Met Asp Ala Glu Ala Cys Leu
        115                 120                 125

Arg Gly Leu His Leu His Ile Val Pro Cys Lys His Val Leu Ser Trp
    130                 135                 140

Pro Pro Ser Ser Pro Gly Pro Glu Thr Thr Ala Arg Pro Thr Pro
145                 150                 155                 160

Gly Ala Ala Pro Val Pro Pro Leu Tyr Ser Ser Pro Ser Pro Gln
                165                 170                 175

Ala Val Gln Val Gly Gly Thr Ala Ser Leu His Cys Asp Val Ser Gly
            180                 185                 190

Arg Pro Pro Pro Ala Val Thr Trp Glu Lys Gln Ser His Gln Arg Glu
        195                 200                 205
```

```
Asn Leu Ile Met Arg Pro Asp Gln Met Tyr Gly Asn Val Val Thr
            210                 215                 220

Ser Ile Gly Gln Leu Val Leu Tyr Asn Ala Arg Pro Glu Asp Ala Gly
225                 230                 235                 240

Leu Tyr Thr Cys Thr Ala Arg Asn Ala Ala Gly Leu Leu Arg Ala Asp
            245                 250                 255

Phe Pro Leu Ser Val Val Gln Arg Glu Pro Ala Arg Asp Ala Ala Pro
            260                 265                 270

Ser Ile Pro Ala Pro Ala Glu Cys Leu Pro Asp Val Gln Ala Cys Thr
            275                 280                 285

Gly Pro Thr Ser Pro His Leu Val Leu Trp His Tyr Asp Pro Gln Arg
            290                 295                 300

Gly Gly Cys Met Thr Phe Pro Ala Arg Gly Cys Asp Gly Ala Ala Arg
305                 310                 315                 320

Gly Phe Glu Thr Tyr Glu Ala Cys Gln Gln Ala Cys Ala Arg Gly Pro
            325                 330                 335

Gly Asp Ala Cys Val Leu Pro Ala Val Gln Gly Pro Cys Arg Gly Trp
            340                 345                 350

Glu Pro Arg Trp Ala Tyr Ser Pro Leu Leu Gln Gln Cys His Pro Phe
            355                 360                 365

Val Tyr Gly Gly Cys Glu Gly Asn Gly Asn Asn Phe His Ser Arg Glu
370                 375                 380

Ser Cys Glu Asp Ala Cys Pro Val Pro Arg Thr Pro Pro Cys Arg Ala
385                 390                 395                 400

Cys Arg Leu Arg Ser Lys Leu Ala Leu Ser Leu Cys Arg Ser Asp Phe
            405                 410                 415

Ala Ile Val Gly Arg Leu Thr Glu Val Leu Glu Glu Pro Glu Ala Ala
            420                 425                 430

Gly Gly Ile Ala Arg Val Ala Leu Glu Asp Val Leu Lys Asp Asp Lys
            435                 440                 445

Met Gly Leu Lys Phe Leu Gly Thr Lys Tyr Leu Glu Val Thr Leu Ser
450                 455                 460

Gly Met Asp Trp Ala Cys Pro Cys Pro Asn Met Thr Ala Gly Asp Gly
465                 470                 475                 480

Pro Leu Val Ile Met Gly Glu Val Arg Asp Gly Val Ala Val Leu Asp
            485                 490                 495

Ala Gly Ser Tyr Val Arg Ala Ala Ser Glu Lys Arg Val Lys Lys Ile
            500                 505                 510

Leu Glu Leu Leu Glu Lys Gln Ala Cys Glu Leu Leu Asn Arg Phe Gln
            515                 520                 525

Asp
```

<210> SEQ ID NO 28
<211> LENGTH: 65
<212> TYPE: PRT
<213> ORGANISM: Homo sapiens

<400> SEQUENCE: 28

```
Cys Glu Gly Phe Val Cys Pro Gln Gln Gly Ser Asp Cys Asp Ile Trp
1               5                   10                  15

Asp Gly Gln Pro Val Cys Arg Cys Arg Asp Arg Cys Glu Lys Glu Pro
            20                  25                  30

Ser Phe Thr Cys Ala Ser Asp Gly Leu Thr Tyr Tyr Asn Arg Cys Tyr
            35                  40                  45
```

Met Asp Ala Glu Ala Cys Leu Arg Gly Leu His Leu His Ile Val Pro
 50                  55                  60

Cys
 65

<210> SEQ ID NO 29
<211> LENGTH: 576
<212> TYPE: PRT
<213> ORGANISM: Homo sapiens

<400> SEQUENCE: 29

Met Trp Ala Pro Arg Cys Arg Arg Phe Trp Ser Arg Trp Glu Gln Val
  1               5                  10                  15

Ala Ala Leu Leu Leu Leu Leu Leu Leu Gly Val Pro Pro Arg Ser
                 20                  25                  30

Leu Ala Leu Pro Pro Ile Arg Tyr Ser His Ala Gly Ile Cys Pro Asn
             35                  40                  45

Asp Met Asn Pro Asn Leu Trp Val Asp Ala Gln Ser Thr Cys Arg Arg
 50                  55                  60

Glu Cys Glu Thr Asp Gln Glu Cys Glu Thr Tyr Glu Lys Cys Cys Pro
 65                  70                  75                  80

Asn Val Cys Gly Thr Lys Ser Cys Val Ala Ala Arg Tyr Met Asp Val
                 85                  90                  95

Lys Gly Lys Lys Gly Pro Val Gly Met Pro Lys Glu Ala Thr Cys Asp
            100                 105                 110

His Phe Met Cys Leu Gln Gln Gly Ser Glu Cys Asp Ile Trp Asp Gly
            115                 120                 125

Gln Pro Val Cys Lys Cys Lys Asp Arg Cys Glu Lys Glu Pro Ser Phe
        130                 135                 140

Thr Cys Ala Ser Asp Gly Leu Thr Tyr Tyr Asn Arg Cys Tyr Met Asp
145                 150                 155                 160

Ala Glu Ala Cys Ser Lys Gly Ile Thr Leu Ala Val Val Thr Cys Arg
                165                 170                 175

Tyr His Phe Thr Trp Pro Asn Thr Ser Pro Pro Pro Glu Thr Thr
            180                 185                 190

Met His Pro Thr Thr Ala Ser Pro Glu Thr Pro Glu Leu Asp Met Ala
            195                 200                 205

Ala Pro Ala Leu Leu Asn Asn Pro Val His Gln Ser Val Thr Met Gly
        210                 215                 220

Glu Thr Val Ser Phe Leu Cys Asp Val Val Gly Arg Pro Arg Pro Glu
225                 230                 235                 240

Ile Thr Trp Glu Lys Gln Leu Glu Asp Arg Glu Asn Val Val Met Arg
                245                 250                 255

Pro Asn His Val Arg Gly Asn Val Val Thr Asn Ile Ala Gln Leu
            260                 265                 270

Val Ile Tyr Asn Ala Gln Leu Gln Asp Ala Gly Ile Tyr Thr Cys Thr
            275                 280                 285

Ala Arg Asn Val Ala Gly Val Leu Arg Ala Asp Phe Pro Leu Ser Val
        290                 295                 300

Val Arg Gly His Gln Ala Ala Thr Ser Glu Ser Pro Asn Gly
305                 310                 315                 320

Thr Ala Phe Pro Ala Ala Glu Cys Leu Lys Pro Pro Asp Ser Glu Asp
                325                 330                 335

Cys Gly Glu Glu Gln Thr Arg Trp His Phe Asp Ala Gln Ala Asn Asn

```
                    340               345               350
Cys Leu Thr Phe Thr Phe Gly His Cys His Arg Asn Leu Asn His Phe
        355                 360                 365

Glu Thr Tyr Glu Ala Cys Met Leu Ala Cys Met Ser Gly Pro Leu Ala
    370                 375                 380

Ala Cys Ser Leu Pro Ala Leu Gln Gly Pro Cys Lys Ala Tyr Ala Pro
385                 390                 395                 400

Arg Trp Ala Tyr Asn Ser Gln Thr Gly Gln Cys Gln Ser Phe Val Tyr
                405                 410                 415

Gly Gly Cys Glu Gly Asn Gly Asn Asn Phe Glu Ser Arg Glu Ala Cys
            420                 425                 430

Glu Glu Ser Cys Pro Phe Pro Arg Gly Asn Gln Arg Cys Arg Ala Cys
                435                 440                 445

Lys Pro Arg Gln Lys Leu Val Thr Ser Phe Cys Arg Ser Asp Phe Val
        450                 455                 460

Ile Leu Gly Arg Val Ser Glu Leu Thr Glu Glu Pro Asp Ser Gly Arg
465                 470                 475                 480

Ala Leu Val Thr Val Asp Glu Val Leu Lys Asp Glu Lys Met Gly Leu
                485                 490                 495

Lys Phe Leu Gly Gln Glu Pro Leu Glu Val Thr Leu His Val Asp
                500                 505                 510

Trp Ala Cys Pro Cys Pro Asn Val Thr Val Ser Glu Met Pro Leu Ile
                515                 520                 525

Ile Met Gly Glu Val Asp Gly Gly Met Ala Met Leu Arg Pro Asp Ser
530                 535                 540

Phe Val Gly Ala Ser Ser Ala Arg Arg Val Arg Lys Leu Arg Glu Val
545                 550                 555                 560

Met His Lys Lys Thr Cys Asp Val Leu Lys Glu Phe Leu Gly Leu His
                565                 570                 575

<210> SEQ ID NO 30
<211> LENGTH: 542
<212> TYPE: PRT
<213> ORGANISM: Homo sapiens

<400> SEQUENCE: 30

Leu Pro Pro Ile Arg Tyr Ser His Ala Gly Ile Cys Pro Asn Asp Met
1                   5                   10                  15

Asn Pro Asn Leu Trp Val Asp Ala Gln Ser Thr Cys Arg Arg Glu Cys
                20                  25                  30

Glu Thr Asp Gln Glu Cys Glu Thr Tyr Glu Lys Cys Cys Pro Asn Val
            35                  40                  45

Cys Gly Thr Lys Ser Cys Val Ala Ala Arg Tyr Met Asp Val Lys Gly
        50                  55                  60

Lys Lys Gly Pro Val Gly Met Pro Lys Glu Ala Thr Cys Asp His Phe
65                  70                  75                  80

Met Cys Leu Gln Gln Gly Ser Glu Cys Asp Ile Trp Asp Gly Gln Pro
                85                  90                  95

Val Cys Lys Cys Lys Asp Arg Cys Glu Lys Glu Pro Ser Phe Thr Cys
                100                 105                 110

Ala Ser Asp Gly Leu Thr Tyr Tyr Asn Arg Cys Tyr Met Asp Ala Glu
            115                 120                 125

Ala Cys Ser Lys Gly Ile Thr Leu Ala Val Val Thr Cys Arg Tyr His
        130                 135                 140
```

Phe Thr Trp Pro Asn Thr Ser Pro Pro Pro Glu Thr Met His
145                 150                 155                 160

Pro Thr Thr Ala Ser Pro Glu Thr Pro Glu Leu Asp Met Ala Ala Pro
                165                 170                 175

Ala Leu Leu Asn Asn Pro Val His Gln Ser Val Thr Met Gly Glu Thr
            180                 185                 190

Val Ser Phe Leu Cys Asp Val Gly Arg Pro Arg Pro Glu Ile Thr
        195                 200                 205

Trp Glu Lys Gln Leu Glu Asp Arg Glu Asn Val Val Met Arg Pro Asn
    210                 215                 220

His Val Arg Gly Asn Val Val Thr Asn Ile Ala Gln Leu Val Ile
225                 230                 235                 240

Tyr Asn Ala Gln Leu Gln Asp Ala Gly Ile Tyr Thr Cys Thr Ala Arg
                245                 250                 255

Asn Val Ala Gly Val Leu Arg Ala Asp Phe Pro Leu Ser Val Val Arg
            260                 265                 270

Gly His Gln Ala Ala Thr Ser Glu Ser Pro Asn Gly Thr Ala
        275                 280                 285

Phe Pro Ala Ala Glu Cys Leu Lys Pro Pro Asp Ser Glu Asp Cys Gly
290                 295                 300

Glu Glu Gln Thr Arg Trp His Phe Asp Ala Gln Ala Asn Asn Cys Leu
305                 310                 315                 320

Thr Phe Thr Phe Gly His Cys His Arg Asn Leu Asn His Phe Glu Thr
                325                 330                 335

Tyr Glu Ala Cys Met Leu Ala Cys Met Ser Gly Pro Leu Ala Ala Cys
            340                 345                 350

Ser Leu Pro Ala Leu Gln Gly Pro Cys Lys Ala Tyr Ala Pro Arg Trp
        355                 360                 365

Ala Tyr Asn Ser Gln Thr Gly Gln Cys Gln Ser Phe Val Tyr Gly Gly
    370                 375                 380

Cys Glu Gly Asn Gly Asn Asn Phe Glu Ser Arg Glu Ala Cys Glu Glu
385                 390                 395                 400

Ser Cys Pro Phe Pro Arg Gly Asn Gln Arg Cys Arg Ala Cys Lys Pro
                405                 410                 415

Arg Gln Lys Leu Val Thr Ser Phe Cys Arg Ser Asp Phe Val Ile Leu
            420                 425                 430

Gly Arg Val Ser Glu Leu Thr Glu Glu Pro Asp Ser Gly Arg Ala Leu
        435                 440                 445

Val Thr Val Asp Glu Val Leu Lys Asp Glu Lys Met Gly Leu Lys Phe
    450                 455                 460

Leu Gly Gln Glu Pro Leu Glu Val Thr Leu Leu His Val Asp Trp Ala
465                 470                 475                 480

Cys Pro Cys Pro Asn Val Thr Val Ser Glu Met Pro Leu Ile Ile Met
                485                 490                 495

Gly Glu Val Asp Gly Gly Met Ala Met Leu Arg Pro Ser Phe Val
            500                 505                 510

Gly Ala Ser Ser Ala Arg Arg Val Arg Lys Leu Arg Glu Val Met His
        515                 520                 525

Lys Lys Thr Cys Asp Val Leu Lys Glu Phe Leu Gly Leu His
    530                 535                 540

<210> SEQ ID NO 31
<211> LENGTH: 65
<212> TYPE: PRT

<213> ORGANISM: Homo sapiens

<400> SEQUENCE: 31

Cys Asp His Phe Met Cys Leu Gln Gln Gly Ser Glu Cys Asp Ile Trp
1               5                   10                  15

Asp Gly Gln Pro Val Cys Lys Cys Lys Asp Arg Cys Glu Lys Glu Pro
                20                  25                  30

Ser Phe Thr Cys Ala Ser Asp Gly Leu Thr Tyr Tyr Asn Arg Cys Tyr
            35                  40                  45

Met Asp Ala Glu Ala Cys Ser Lys Gly Ile Thr Leu Ala Val Val Thr
    50                  55                  60

Cys
65

<210> SEQ ID NO 32
<211> LENGTH: 571
<212> TYPE: PRT
<213> ORGANISM: Mus musculus

<400> SEQUENCE: 32

Met Cys Ala Pro Gly Tyr His Arg Phe Trp Phe His Trp Gly Leu Leu
1               5                   10                  15

Leu Leu Leu Leu Leu Glu Ala Pro Leu Arg Gly Leu Ala Leu Pro Pro
                20                  25                  30

Ile Arg Tyr Ser His Ala Gly Ile Cys Pro Asn Asp Met Asn Pro Asn
            35                  40                  45

Leu Trp Val Asp Ala Gln Ser Thr Cys Lys Arg Glu Cys Glu Thr Asp
    50                  55                  60

Gln Glu Cys Glu Thr Tyr Glu Lys Cys Cys Pro Asn Val Cys Gly Thr
65                  70                  75                  80

Lys Ser Cys Val Ala Ala Arg Tyr Met Asp Val Lys Gly Lys Lys Gly
                85                  90                  95

Pro Val Gly Met Pro Lys Glu Ala Thr Cys Asp His Phe Met Cys Leu
                100                 105                 110

Gln Gln Gly Ser Glu Cys Asp Ile Trp Asp Gly Gln Pro Val Cys Lys
            115                 120                 125

Cys Lys Asp Arg Cys Glu Lys Glu Pro Ser Phe Thr Cys Ala Ser Asp
    130                 135                 140

Gly Leu Thr Tyr Tyr Asn Arg Cys Phe Met Asp Ala Glu Ala Cys Ser
145                 150                 155                 160

Lys Gly Ile Thr Leu Ser Val Val Thr Cys Arg Tyr His Phe Thr Trp
                165                 170                 175

Pro Asn Thr Ser Pro Pro Pro Glu Thr Thr Val His Pro Thr Thr
                180                 185                 190

Ala Ser Pro Glu Thr Leu Gly Leu Asp Met Ala Ala Pro Ala Leu Leu
            195                 200                 205

Asn His Pro Val His Gln Ser Val Thr Val Gly Glu Thr Val Ser Phe
    210                 215                 220

Leu Cys Asp Val Val Gly Arg Pro Arg Pro Glu Leu Thr Trp Glu Lys
225                 230                 235                 240

Gln Leu Glu Asp Arg Glu Asn Val Val Met Arg Pro Asn His Val Arg
                245                 250                 255

Gly Asn Val Val Val Thr Asn Ile Ala Gln Leu Val Ile Tyr Asn Val
            260                 265                 270

Gln Pro Gln Asp Ala Gly Ile Tyr Thr Cys Thr Ala Arg Asn Val Ala

```
            275                 280                 285
Gly Val Leu Arg Ala Asp Phe Pro Leu Ser Val Val Arg Gly Gly Gln
290                 295                 300

Ala Arg Ala Thr Ser Glu Ser Ser Leu Asn Gly Thr Ala Phe Pro Ala
305                 310                 315                 320

Thr Glu Cys Leu Lys Pro Pro Asp Ser Glu Asp Cys Gly Glu Glu Gln
                    325                 330                 335

Thr Arg Trp His Phe Asp Ala Gln Ala Asn Asn Cys Leu Thr Phe Thr
                340                 345                 350

Phe Gly His Cys His His Asn Leu Asn His Phe Glu Thr Tyr Glu Ala
            355                 360                 365

Cys Met Leu Ala Cys Met Ser Gly Pro Leu Ala Ile Cys Ser Leu Pro
370                 375                 380

Ala Leu Gln Gly Pro Cys Lys Ala Tyr Val Pro Arg Trp Ala Tyr Asn
385                 390                 395                 400

Ser Gln Thr Gly Leu Cys Gln Ser Phe Val Tyr Gly Gly Cys Glu Gly
                    405                 410                 415

Asn Gly Asn Asn Phe Glu Ser Arg Glu Ala Cys Glu Glu Ser Cys Pro
                420                 425                 430

Phe Pro Arg Gly Asn Gln His Cys Arg Ala Cys Lys Pro Arg Gln Lys
            435                 440                 445

Leu Val Thr Ser Phe Cys Arg Ser Asp Phe Val Ile Leu Gly Arg Val
450                 455                 460

Ser Glu Leu Thr Glu Glu Gln Asp Ser Gly Arg Ala Leu Val Thr Val
465                 470                 475                 480

Asp Glu Val Leu Lys Asp Glu Lys Met Gly Leu Lys Phe Leu Gly Arg
                    485                 490                 495

Glu Pro Leu Glu Val Thr Leu Leu His Val Asp Trp Thr Cys Pro Cys
                500                 505                 510

Pro Asn Val Thr Val Gly Glu Thr Pro Leu Ile Ile Met Gly Glu Val
            515                 520                 525

Asp Gly Gly Met Ala Met Leu Arg Pro Asp Ser Phe Val Gly Ala Ser
530                 535                 540

Ser Thr Arg Arg Val Arg Lys Leu Arg Glu Val Met Tyr Lys Lys Thr
545                 550                 555                 560

Cys Asp Val Leu Lys Asp Phe Leu Gly Leu Gln
                    565                 570

<210> SEQ ID NO 33
<211> LENGTH: 542
<212> TYPE: PRT
<213> ORGANISM: Mus musculus

<400> SEQUENCE: 33

Leu Pro Pro Ile Arg Tyr Ser His Ala Gly Ile Cys Pro Asn Asp Met
1               5                   10                  15

Asn Pro Asn Leu Trp Val Asp Ala Gln Ser Thr Cys Lys Arg Glu Cys
                20                  25                  30

Glu Thr Asp Gln Glu Cys Glu Thr Tyr Glu Lys Cys Cys Pro Asn Val
            35                  40                  45

Cys Gly Thr Lys Ser Cys Val Ala Ala Arg Tyr Met Asp Val Lys Gly
        50                  55                  60

Lys Lys Gly Pro Val Gly Met Pro Lys Glu Ala Thr Cys Asp His Phe
65                  70                  75                  80
```

```
Met Cys Leu Gln Gln Gly Ser Glu Cys Asp Ile Trp Asp Gly Gln Pro
             85                  90                  95
Val Cys Lys Cys Lys Asp Arg Cys Glu Lys Glu Pro Ser Phe Thr Cys
            100                 105                 110
Ala Ser Asp Gly Leu Thr Tyr Tyr Asn Arg Cys Phe Met Asp Ala Glu
            115                 120                 125
Ala Cys Ser Lys Gly Ile Thr Leu Ser Val Val Thr Cys Arg Tyr His
            130                 135                 140
Phe Thr Trp Pro Asn Thr Ser Pro Pro Pro Glu Thr Thr Val His
145                 150                 155                 160
Pro Thr Thr Ala Ser Pro Glu Thr Leu Gly Leu Asp Met Ala Ala Pro
                165                 170                 175
Ala Leu Leu Asn His Pro Val His Gln Ser Val Thr Val Gly Glu Thr
            180                 185                 190
Val Ser Phe Leu Cys Asp Val Val Gly Arg Pro Arg Pro Glu Leu Thr
            195                 200                 205
Trp Glu Lys Gln Leu Glu Asp Arg Glu Asn Val Val Met Arg Pro Asn
            210                 215                 220
His Val Arg Gly Asn Val Val Thr Asn Ile Ala Gln Leu Val Ile
225                 230                 235                 240
Tyr Asn Val Gln Pro Gln Asp Ala Gly Ile Tyr Thr Cys Thr Ala Arg
                245                 250                 255
Asn Val Ala Gly Val Leu Arg Ala Asp Phe Pro Leu Ser Val Val Arg
                260                 265                 270
Gly Gly Gln Ala Arg Ala Thr Ser Glu Ser Ser Leu Asn Gly Thr Ala
            275                 280                 285
Phe Pro Ala Thr Glu Cys Leu Lys Pro Pro Asp Ser Glu Asp Cys Gly
            290                 295                 300
Glu Glu Gln Thr Arg Trp His Phe Asp Ala Gln Ala Asn Asn Cys Leu
305                 310                 315                 320
Thr Phe Thr Phe Gly His Cys His His Asn Leu Asn His Phe Glu Thr
                325                 330                 335
Tyr Glu Ala Cys Met Leu Ala Cys Met Ser Gly Pro Leu Ala Ile Cys
            340                 345                 350
Ser Leu Pro Ala Leu Gln Gly Pro Cys Lys Ala Tyr Val Pro Arg Trp
            355                 360                 365
Ala Tyr Asn Ser Gln Thr Gly Leu Cys Gln Ser Phe Val Tyr Gly Gly
            370                 375                 380
Cys Glu Gly Asn Gly Asn Asn Phe Glu Ser Arg Glu Ala Cys Glu Glu
385                 390                 395                 400
Ser Cys Pro Phe Pro Arg Gly Asn Gln His Cys Arg Ala Cys Lys Pro
                405                 410                 415
Arg Gln Lys Leu Val Thr Ser Phe Cys Arg Ser Asp Phe Val Ile Leu
            420                 425                 430
Gly Arg Val Ser Glu Leu Thr Glu Glu Gln Asp Ser Gly Arg Ala Leu
            435                 440                 445
Val Thr Val Asp Glu Val Leu Lys Asp Glu Lys Met Gly Leu Lys Phe
            450                 455                 460
Leu Gly Arg Glu Pro Leu Glu Val Thr Leu His Val Asp Trp Thr
465                 470                 475                 480
Cys Pro Cys Pro Asn Val Thr Val Gly Glu Thr Pro Leu Ile Ile Met
                485                 490                 495
Gly Glu Val Asp Gly Gly Met Ala Met Leu Arg Pro Asp Ser Phe Val
```

```
                500                 505                 510
Gly Ala Ser Ser Thr Arg Arg Val Arg Lys Leu Arg Glu Val Met Tyr
            515                 520                 525
Lys Lys Thr Cys Asp Val Leu Lys Asp Phe Leu Gly Leu Gln
530                 535                 540

<210> SEQ ID NO 34
<211> LENGTH: 225
<212> TYPE: PRT
<213> ORGANISM: Homo sapiens

<400> SEQUENCE: 34

Thr His Thr Cys Pro Pro Cys Pro Ala Pro Glu Leu Leu Gly Gly Pro
1               5                   10                  15
Ser Val Phe Leu Phe Pro Pro Lys Pro Lys Asp Thr Leu Met Ile Ser
            20                  25                  30
Arg Thr Pro Glu Val Thr Cys Val Val Val Asp Val Ser His Glu Asp
        35                  40                  45
Pro Glu Val Lys Phe Asn Trp Tyr Val Asp Gly Val Glu Val His Asn
    50                  55                  60
Ala Lys Thr Lys Pro Arg Glu Glu Gln Tyr Asn Ser Thr Tyr Arg Val
65                  70                  75                  80
Val Ser Val Leu Thr Val Leu His Gln Asp Trp Leu Asn Gly Lys Glu
                85                  90                  95
Tyr Lys Cys Lys Val Ser Asn Lys Ala Leu Pro Ala Pro Ile Glu Lys
            100                 105                 110
Thr Ile Ser Lys Ala Lys Gly Gln Pro Arg Glu Pro Gln Val Tyr Thr
        115                 120                 125
Leu Pro Pro Ser Arg Glu Glu Met Thr Lys Asn Gln Val Ser Leu Thr
    130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
                165                 170                 175
Asp Ser Asp Gly Ser Phe Phe Leu Tyr Ser Lys Leu Thr Val Asp Lys
            180                 185                 190
Ser Arg Trp Gln Gln Gly Asn Val Phe Ser Cys Ser Val Met His Glu
        195                 200                 205
Ala Leu His Asn His Tyr Thr Gln Lys Ser Leu Ser Leu Ser Pro Gly
    210                 215                 220
Lys
225

<210> SEQ ID NO 35
<211> LENGTH: 223
<212> TYPE: PRT
<213> ORGANISM: Homo sapiens

<400> SEQUENCE: 35

Val Glu Cys Pro Pro Cys Pro Ala Pro Pro Val Ala Gly Pro Ser Val
1               5                   10                  15
Phe Leu Phe Pro Pro Lys Pro Lys Asp Thr Leu Met Ile Ser Arg Thr
            20                  25                  30
Pro Glu Val Thr Cys Val Val Val Asp Val Ser His Glu Asp Pro Glu
        35                  40                  45
Val Gln Phe Asn Trp Tyr Val Asp Gly Val Glu Val His Asn Ala Lys
```

```
            50                  55                  60
Thr Lys Pro Arg Glu Glu Gln Phe Asn Ser Thr Phe Arg Val Val Ser
 65                  70                  75                  80

Val Leu Thr Val Val His Gln Asp Trp Leu Asn Gly Lys Glu Tyr Lys
                 85                  90                  95

Cys Lys Val Ser Asn Lys Gly Leu Pro Ala Pro Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 36
<211> LENGTH: 232
<212> TYPE: PRT
<213> ORGANISM: Homo sapiens

<400> SEQUENCE: 36

Glu Pro Lys Ser Cys Asp Thr Pro Pro Pro Cys Pro Arg Cys Pro Ala
 1               5                  10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
             35                  40                  45

Val Asp Val Ser His Glu Asp Pro Glu Val Gln Phe Lys Trp Tyr Val
         50                  55                  60

Asp Gly Val Glu Val His Asn Ala Lys Thr Lys Pro Arg Glu Glu Gln
 65                  70                  75                  80

Tyr Asn Ser Thr Phe Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Thr Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205
```

```
Ser Cys Ser Val Met His Glu Ala Leu His Asn Arg Phe Thr Gln Lys
    210                 215                 220
Ser Leu Ser Leu Ser Pro Gly Lys
225                 230
```

<210> SEQ ID NO 37
<211> LENGTH: 279
<212> TYPE: PRT
<213> ORGANISM: Homo sapiens

<400> SEQUENCE: 37

```
Glu Leu Lys Thr Pro Leu Gly Asp Thr Thr His Thr Cys Pro Arg Cys
1               5                   10                  15
Pro Glu Pro Lys Ser Cys Asp Thr Pro Pro Cys Pro Arg Cys Pro
            20                  25                  30
Glu Pro Lys Ser Cys Asp Thr Pro Pro Cys Pro Arg Cys Pro Glu
            35                  40                  45
Pro Lys Ser Cys Asp Thr Pro Pro Cys Pro Arg Cys Pro Ala Pro
50                  55                  60
Glu Leu Leu Gly Gly Pro Ser Val Phe Leu Phe Pro Pro Lys Pro Lys
65                  70                  75                  80
Asp Thr Leu Met Ile Ser Arg Thr Pro Glu Val Thr Cys Val Val Val
                85                  90                  95
Asp Val Ser His Glu Asp Pro Gln Val Gln Phe Lys Trp Tyr Val Asp
            100                 105                 110
Gly Val Glu Val His Asn Ala Lys Thr Lys Pro Arg Glu Glu Gln Tyr
        115                 120                 125
Asn Ser Thr Phe Arg Val Val Ser Val Leu Thr Val Leu His Gln Asp
    130                 135                 140
Trp Leu Asn Gly Lys Glu Tyr Lys Cys Lys Val Ser Asn Lys Ala Leu
145                 150                 155                 160
Pro Ala Pro Ile Glu Lys Thr Ile Ser Lys Thr Lys Gly Gln Pro Arg
                165                 170                 175
Glu Pro Gln Val Tyr Thr Leu Pro Pro Ser Arg Glu Glu Met Thr Lys
            180                 185                 190
Asn Gln Val Ser Leu Thr Cys Leu Val Lys Gly Phe Tyr Pro Ser Asp
        195                 200                 205
Ile Ala Val Glu Trp Glu Ser Ser Gly Gln Pro Glu Asn Asn Tyr Asn
    210                 215                 220
Thr Thr Pro Pro Met Leu Asp Ser Asp Gly Ser Phe Phe Leu Tyr Ser
225                 230                 235                 240
Lys Leu Thr Val Asp Lys Ser Arg Trp Gln Gln Gly Asn Ile Phe Ser
                245                 250                 255
Cys Ser Val Met His Glu Ala Leu His Asn Arg Phe Thr Gln Lys Ser
            260                 265                 270
Leu Ser Leu Ser Pro Gly Lys
        275
```

<210> SEQ ID NO 38
<211> LENGTH: 229
<212> TYPE: PRT
<213> ORGANISM: Homo sapiens

<400> SEQUENCE: 38

```
Glu Ser Lys Tyr Gly Pro Pro Cys Pro Ser Cys Pro Ala Pro Glu Phe
1               5                   10                  15
```

-continued

```
Leu Gly Gly Pro Ser Val Phe Leu Phe Pro Pro Lys Pro Lys Asp Thr
             20                  25                  30

Leu Met Ile Ser Arg Thr Pro Glu Val Thr Cys Val Val Val Asp Val
         35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 39
<211> LENGTH: 225
<212> TYPE: PRT
<213> ORGANISM: Homo sapiens

<400> SEQUENCE: 39

Thr His Thr Cys Pro Pro Cys Pro Ala Pro Glu Leu Leu Gly Gly Pro
 1               5                  10                  15

Ser Val Phe Leu Phe Pro Pro Lys Pro Lys Asp Thr Leu Met Ile Ser
             20                  25                  30

Arg Thr Pro Glu Val Thr Cys Val Val Val Asp Val Ser His Glu Asp
         35                  40                  45

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Lys Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160
```

Ser Asn Gly Gln Pro Glu Asn Asn Tyr Lys Thr Thr Pro Pro Val Leu
                165                 170                 175

Lys Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 40
<211> LENGTH: 225
<212> TYPE: PRT
<213> ORGANISM: Homo sapiens

<400> SEQUENCE: 40

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Asp Thr Thr Pro Pro Val Leu
                165                 170                 175

Asp Ser Asp Gly Ser Phe Phe Leu Tyr Ser Asp Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 41
<211> LENGTH: 225
<212> TYPE: PRT
<213> ORGANISM: Homo sapiens

<400> SEQUENCE: 41

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Tyr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
            195                 200                 205

Ala Leu His Asn His Tyr Thr Gln Lys Ser Leu Ser Leu Ser Pro Gly
            210                 215                 220

Lys
225

<210> SEQ ID NO 42
<211> LENGTH: 225
<212> TYPE: PRT
<213> ORGANISM: Homo sapiens

<400> SEQUENCE: 42

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu

```
                145                 150                 155                 160
Ser Asn Gly Gln Pro Glu Asn Asn Tyr Lys Thr Thr Pro Val Leu
                165                 170                 175

Asp Ser Asp Gly Ser Phe Phe Leu Thr Ser Lys Leu Thr Val Asp Lys
                180                 185                 190

Ser Arg Trp Gln Gln Gly Asn Val Phe Ser Cys Ser Val Met His Glu
                195                 200                 205

Ala Leu His Asn His Tyr Thr Gln Lys Ser Leu Ser Leu Ser Pro Gly
210                 215                 220

Lys
225

<210> SEQ ID NO 43
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Cys Arg Glu Glu Met Thr Lys Asn Gln Val Ser Leu Trp
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 44
<211> LENGTH: 225
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 44

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Cys Thr
        115                 120                 125

Leu Pro Pro Ser Arg Glu Glu Met Thr Lys Asn Gln Val Ser Leu Ser
    130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Val Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

<210> SEQ ID NO 45
<211> LENGTH: 228
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 45

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95
```

```
Tyr Lys Cys Lys Val Ser Asn Lys Ala Leu Pro Ala Pro Ile Glu Lys
                100                 105                 110

Thr Ile Ser Lys Ala Lys Gly Gln Pro Phe Arg Pro Glu Val His Leu
            115                 120                 125

Leu Pro Pro Ser Arg Glu Glu Met Thr Lys Asn Gln Val Ser Leu Thr
        130                 135                 140

Cys Leu Ala Arg Gly Phe Tyr Pro Lys Asp Ile Ala Val Glu Trp Glu
145                 150                 155                 160

Ser Asn Gly Gln Pro Glu Asn Asn Tyr Lys Thr Thr Pro Ser Arg Gln
                165                 170                 175

Glu Pro Ser Gln Gly Thr Thr Thr Phe Ala Val Thr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Thr Ile Ser Leu
210                 215                 220

Ser Pro Gly Lys
225

<210> SEQ ID NO 46
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Glu Glu Leu Ala Leu Asn Glu Leu Val Thr Leu
        130                 135                 140

Thr Cys Leu Val Lys Gly Phe Tyr Pro Ser Asp Ile Ala Val Glu Trp
145                 150                 155                 160

Glu Ser Asn Gly Gln Glu Leu Pro Arg Glu Lys Tyr Leu Thr Trp Ala
                165                 170                 175

Pro Val Leu Asp Ser Asp Gly Ser Phe Phe Leu Tyr Ser Ile Leu Arg
            180                 185                 190

Val Ala Ala Glu Asp Trp Lys Lys Gly Asp Thr Phe Ser Cys Ser Val
        195                 200                 205

Met His Glu Ala Leu His Asn His Tyr Thr Gln Lys Ser Leu Asp Arg
210                 215                 220
```

Ser Pro Gly Lys
225

<210> SEQ ID NO 47
<211> LENGTH: 1032
<212> TYPE: DNA
<213> ORGANISM: Homo sapiens

<400> SEQUENCE: 47

| | | | | | |
|---|---|---|---|---|---|
| atggtccgcg | cgaggcacca | gccgggtggg | ctttgcctcc | tgctgctgct | gctctgccag | 60 |
| ttcatggagg | accgcagtgc | ccaggctggg | aactgctggc | tccgtcaagc | gaagaacggc | 120 |
| cgctgccagg | tcctgtacaa | gaccgaactg | agcaaggagg | agtgctgcag | caccggccgg | 180 |
| ctgagcacct | cgtggaccga | ggaggacgtg | aatgacaaca | cactcttcaa | gtggatgatt | 240 |
| ttcaacgggg | gcgcccccaa | ctgcatcccc | tgtaaagaaa | cgtgtgagaa | cgtggactgt | 300 |
| ggacctggga | aaaatgccg | aatgaacaag | aagaacaaac | ccgctgcgt | ctgcgccccg | 360 |
| gattgttcca | acatcacctg | gaagggtcca | gtctgcgggc | tggatgggaa | acctaccgc | 420 |
| aatgaatgtg | cactcctaaa | ggcaagatgt | aaagagcagc | agaactgga | agtccagtac | 480 |
| caaggcagat | gtaaaaagac | ttgtcgggat | gttttctgtc | caggcagctc | cacatgtgtg | 540 |
| gtggaccaga | ccaataatgc | ctactgtgtg | acctgtaatc | ggatttgccc | agagcctgct | 600 |
| tcctctgagc | aatatctctg | tgggaatgat | ggagtcacct | actccagtgc | ctgccacctg | 660 |
| agaaaggcta | cctgcctgct | gggcagatct | attggattag | cctatgaggg | aaagtgtatc | 720 |
| aaagcaaagt | cctgtgaaga | tatccagtgc | actggtggga | aaaaatgttt | atgggatttc | 780 |
| aaggttggga | gaggccggtg | ttccctctgt | gatgagctgt | gccctgacag | taagtcggat | 840 |
| gagcctgtct | gtgccagtga | caatgccact | tatgccagcg | agtgtgccat | gaaggaagct | 900 |
| gcctgctcct | caggtgtgct | actggaagta | agcactccg | gatcttgcaa | ctccatttcg | 960 |
| gaagacaccg | aggaagagga | ggaagatgaa | gaccaggact | acagctttcc | tatatcttct | 1020 |
| attctagagt | gg | | | | | 1032 |

<210> SEQ ID NO 48
<211> LENGTH: 945
<212> TYPE: DNA
<213> ORGANISM: Homo sapiens

<400> SEQUENCE: 48

| | | | | | |
|---|---|---|---|---|---|
| gggaactgct | ggctccgtca | agcgaagaac | ggccgctgcc | aggtcctgta | caagaccgaa | 60 |
| ctgagcaagg | aggagtgctg | cagcaccggc | cggctgagca | cctcgtggac | cgaggaggac | 120 |
| gtgaatgaca | acacactctt | caagtggatg | attttcaacg | gggcgcccc | caactgcatc | 180 |
| ccctgtaaag | aaacgtgtga | gaacgtggac | tgtggacctg | ggaaaaaatg | ccgaatgaac | 240 |
| aagaagaaca | aaccccgctg | cgtctgcgcc | ccggattgtt | ccaacatcac | ctggaagggt | 300 |
| ccagtctgcg | ggctggatgg | gaaaacctac | cgcaatgaat | gtgcactcct | aaaggcaaga | 360 |
| tgtaaagagc | agccagaact | ggaagtccag | taccaaggca | gatgtaaaaa | gacttgtcgg | 420 |
| gatgttttct | gtccaggcag | ctccacatgt | gtggtggacc | agaccaataa | tgcctactgt | 480 |
| gtgacctgta | atcggatttg | cccagagcct | gcttcctctg | agcaatatct | ctgtgggaat | 540 |
| gatggagtca | cctactccag | tgcctgccac | ctgagaaagg | ctacctgcct | gctgggcaga | 600 |
| tctattggat | tagcctatga | gggaaagtgt | atcaaagcaa | agtcctgtga | agatatccag | 660 |
| tgcactggtg | ggaaaaaatg | tttatgggat | ttcaaggttg | ggagaggccg | tgttccctc | 720 |

```
tgtgatgagc tgtgccctga cagtaagtcg gatgagcctg tctgtgccag tgacaatgcc      780
acttatgcca gcgagtgtgc catgaaggaa gctgcctgct cctcaggtgt gctactggaa      840
gtaaagcact ccggatcttg caactccatt tcggaagaca ccgaggaaga ggaggaagat      900
gaagaccagg actacagctt tcctatatct tctattctag agtgg                     945
```

<210> SEQ ID NO 49
<211> LENGTH: 864
<212> TYPE: DNA
<213> ORGANISM: Homo sapiens

<400> SEQUENCE: 49

```
gggaactgct ggctccgtca agcgaagaac ggccgctgcc aggtcctgta caagaccgaa       60
ctgagcaagg aggagtgctg cagcaccggc cggctgagca cctcgtggac cgaggaggac      120
gtgaatgaca acacactctt caagtggatg attttcaacg ggcgcgcccc caactgcatc      180
ccctgtaaag aaacgtgtga gaacgtggac tgtggacctg gaaaaaaatg ccgaatgaac      240
aagaagaaca aaccccgctg cgtctgcgcc ccggattgtt ccaacatcac ctggaagggt      300
ccagtctgcg ggctggatgg gaaaacctac cgcaatgaat gtgcactcct aaaggcaaga      360
tgtaaagagc agccagaact ggaagtccag taccaaggca gatgtaaaaa gacttgtcgg      420
gatgttttct gtccaggcag ctccacatgt gtggtggacc agaccaataa tgcctactgt      480
gtgacctgta atcggatttg cccagagcct gcttcctctg agcaatatct ctgtgggaat      540
gatggagtca cctactccag tgcctgccac ctgagaaagg ctacctgcct gctgggcaga      600
tctattggat tagcctatga gggaaagtgt atcaaagcaa agtcctgtga agatatccag      660
tgcactggtg ggaaaaaatg tttatgggat ttcaaggttg ggagaggccg tgttccctc      720 tgtgatgagc tgtgccctga cagtaagtcg gatgagcctg tctgtgccag tgacaatgcc      780
acttatgcca gcgagtgtgc catgaaggaa gctgcctgct cctcaggtgt gctactggaa      840
gtaaagcact ccggatcttg caac                                             864
```

<210> SEQ ID NO 50
<211> LENGTH: 876
<212> TYPE: DNA
<213> ORGANISM: Homo sapiens

<400> SEQUENCE: 50

```
gggaactgct ggctccgtca agcgaagaac ggccgctgcc aggtcctgta caagaccgaa       60
ctgagcaagg aggagtgctg cagcaccggc cggctgagca cctcgtggac cgaggaggac      120
gtgaatgaca acacactctt caagtggatg attttcaacg ggcgcgcccc caactgcatc      180
ccctgtaaag aaacgtgtga gaacgtggac tgtggacctg gaaaaaaatg ccgaatgaac      240
aagaagaaca aaccccgctg cgtctgcgcc ccggattgtt ccaacatcac ctggaagggt      300
ccagtctgcg ggctggatgg gaaaacctac cgcaatgaat gtgcactcct aaaggcaaga      360
tgtaaagagc agccagaact ggaagtccag taccaaggca gatgtaaaaa gacttgtcgg      420
gatgttttct gtccaggcag ctccacatgt gtggtggacc agaccaataa tgcctactgt      480
gtgacctgta atcggatttg cccagagcct gcttcctctg agcaatatct ctgtgggaat      540
gatggagtca cctactccag tgcctgccac ctgagaaagg ctacctgcct gctgggcaga      600
tctattggat tagcctatga gggaaagtgt atcaaagcaa agtcctgtga agatatccag      660
tgcactggtg ggaaaaaatg tttatgggat ttcaaggttg ggagaggccg tgttccctc      720
```

| | |
|---|---:|
| tgtgatgagc tgtgccctga cagtaagtcg gatgagcctg tctgtgccag tgacaatgcc | 780 |
| acttatgcca gcgagtgtgc catgaaggaa gctgcctgct cctcaggtgt gctactggaa | 840 |
| gtaaagcact ccggatcttg caactccatt tcgtgg | 876 |

<210> SEQ ID NO 51
<211> LENGTH: 789
<212> TYPE: DNA
<213> ORGANISM: Homo sapiens

<400> SEQUENCE: 51

| | |
|---|---:|
| atgcgtcccg gggcgccagg gccactctgg cctctgccct gggggggccct ggcttgggcc | 60 |
| gtgggcttcg tgagctccat gggctcgggg aaccccgcgc ccggtggtgt ttgctggctc | 120 |
| cagcagggcc aggaggccac ctgcagcctg gtgctccaga ctgatgtcac ccgggccgag | 180 |
| tgctgtgcct ccggcaacat tgacaccgcc tggtccaacc tcacccaccc ggggaacaag | 240 |
| atcaacctcc tcggcttctt gggccttgtc cactgcctcc cctgcaaaga ttcgtgcgac | 300 |
| ggcgtggagt gcgccccggg caaggcgtgc cgcatgctgg ggggccgccc cgcgctgcgag | 360 |
| tgcgcgcccg actgctcggg gctcccggcg cggctgcagg tctgcggctc agacggcgcc | 420 |
| acctaccgcg acgagtgcga gctgcgcgcc gcgcgctgcc gcggccaccc ggacctgagc | 480 |
| gtcatgtacc ggggccgctg ccgcaagtcc tgtgagcacg tggtgtgccc gcggccacag | 540 |
| tcgtgcgtcg tggaccagac gggcagcgcc cactgcgtgg tgtgtcgagc ggcgccctgc | 600 |
| cctgtgccct ccagccccgg ccaggagctt tgcggcaaca acaacgtcac ctacatctcc | 660 |
| tcgtgccaca tgcgccaggc cacctgcttc ctgggccgct ccatcggcgt gcgccacgcg | 720 |
| ggcagctgcg caggcacccc tgaggagccg ccaggtggtg agtctgcaga agaggaagag | 780 |
| aacttcgtg | 789 |

<210> SEQ ID NO 52
<211> LENGTH: 711
<212> TYPE: DNA
<213> ORGANISM: Homo sapiens

<400> SEQUENCE: 52

| | |
|---|---:|
| atgggctcgg ggaaccccgc gcccggtggt gtttgctggc tccagcaggg ccaggaggcc | 60 |
| acctgcagcc tggtgctcca gactgatgtc acccgggccg agtgctgtgc ctccggcaac | 120 |
| attgacaccg cctggtccaa cctcacccac ccggggaaca agatcaacct cctcggcttc | 180 |
| ttgggccttg tccactgcct ccctgcaaa gattcgtgcg acggcgtgga gtgcggcccg | 240 |
| ggcaaggcgt gccgcatgct ggggggccgc ccgcgctgcg agtgcgcgcc cgactgctcg | 300 |
| gggctcccgg cgcggctgca ggtctgcggc tcagacggcg ccacctaccg cgacgagtgc | 360 |
| gagctgcgcg ccgcgcgctg ccgcggccac ccggacctga gcgtcatgta ccggggccgc | 420 |
| tgccgcaagt cctgtgagca cgtggtgtgc ccgcggccac agtcgtgcgt cgtggaccag | 480 |
| acgggcagcg cccactgcgt ggtgtgtcga gcggcgccct gccctgtgcc ctccagcccc | 540 |
| ggccaggagc tttgcggcaa caacaacgtc acctacatct cctcgtgcca catgcgccag | 600 |
| gccacctgct tcctgggccg ctccatcggc gtgcgccacg cgggcagctg cgcaggcacc | 660 |
| cctgaggagc cgccaggtgg tgagtctgca gaagaggaag agaacttcgt g | 711 |

<210> SEQ ID NO 53
<211> LENGTH: 1644
<212> TYPE: DNA
<213> ORGANISM: Homo sapiens

<400> SEQUENCE: 53

```
atgcccgccc tacgtccact cctgccgctc ctgctcctcc tccggctgac ctcgggggct      60
ggcttgctgc cagggctggg gagccacccg ggcgtgtgcc ccaaccagct cagccccaac     120
ctgtgggtgg acgcccagag cacctgtgag cgcgagtgta gcagggacca ggactgtgcg     180
gctgctgaga agtgctgcat caacgtgtgt ggactgcaca gctgcgtggc agcacgcttc     240
cccggcagcc cagctgcgcc gacgacagcg gcctcctgcg agggctttgt gtgcccacag     300
cagggctcgg actgcgacat ctgggacggg cagcccgtgt gccgctgccg cgaccgctgt     360
gagaaggagc ccagcttcac ctgcgcctcg gacggcctca cctactacaa ccgctgctat     420
atggacgccg aggcctgcct gcggggcctg cacctccaca tcgtgccctg caagcacgtg     480
ctcagctggc cgcccagcag cccggggccg ccggagacca ctgcccgccc cacacctggg     540
gccgcgcccg tgcctcctgc cctgtacagc agcccctccc cacaggcggt gcaggttggg     600
ggtacggcca gctccactg cgacgtcagc ggccgcccgc cgcctgctgt gacctgggag     660
aagcagagtc accagcgaga gaacctgatc atgcgccctg atcagatgta tggcaacgtg     720
gtggtcacca gcatcgggca gctggtgctc tacaacgcgc ggcccgaaga cgccggcctg     780
tacacctgca ccgcgcgcaa cgctgctggg ctgctgcggg ctgacttccc actctctgtg     840
gtccagcgag agccggccag ggacgcagcc cccagcatcc cagccccggc cgagtgcctg     900
ccggatgtgc aggcctgcac gggccccact tccccacacc ttgtcctctg gcactacgac     960
ccgcagcggg gcggctgcat gaccttcccg gccgtggct gtgatggggc ggcccgcggc    1020
tttgagacct acgaggcatg ccagcaggcc tgtgcccgcg gccccggcga cgcctgcgtg    1080
ctgcctgccg tgcagggccc ctgccggggc tgggagccgc gctgggccta cagcccgctg    1140
ctgcagcagt gccatcccctt cgtgtacggt ggctgcgagg caacggcaa caacttccac    1200
agccgcgaga gctgcgagga tgcctgcccc gtgccgcgca caccgccctg ccgcgcctgc    1260
cgcctccgga gcaagctggc gctgagcctg tgccgcagcg acttcgccat cgtggggcgg    1320
ctcacggagg tgctggagga gcccgaggcc gccggcggca tcgcccgcgt ggcgctcgag    1380
gacgtgctca aggatgacaa gatgggcctc aagttcttgg gcaccaagta cctggaggtg    1440
acgctgagtg gcatggactg ggcctgcccc tgccccaaca tgacggcggg cgacgggccg    1500
ctggtcatca tgggtgaggt gcgcgatggc gtggccgtgc tggacgccgg cagctacgtc    1560
cgcgccgcca gcgagaagcg cgtcaagaag atcttggagc tgctggagaa gcaggcctgc    1620
gagctgctca accgcttcca ggac                                            1644
```

<210> SEQ ID NO 54
<211> LENGTH: 1587
<212> TYPE: DNA
<213> ORGANISM: Homo sapiens

<400> SEQUENCE: 54

```
gctggcttgc tgccagggct ggggagccac ccggggcgtgt gccccaacca gctcagcccc      60
aacctgtggg tggacgccca gagcacctgt gagcgcgagt gtagcaggga ccaggactgt     120
gcggctgctg agaagtgctg catcaacgtg tgtggactgc acagctgcgt ggcagcacgc     180
ttccccggca gcccagctgc gccgacgaca gcggcctcct gcgagggctt tgtgtgccca     240
cagcagggct cggactgcga catctgggac gggcagcccg tgtgccgctg ccgcgaccgc     300
tgtgagaagg agcccagctt cacctgcgcc tcggacggcc tcacctacta caaccgctgc     360
```

-continued

```
tatatggacg ccgaggcctg cctgcggggc ctgcacctcc acatcgtgcc ctgcaagcac      420
gtgctcagct ggccgcccag cagcccgggg ccgccggaga ccactgcccg cccacacct       480 ggggccgcgc ccgtgcctcc tgccctgtac agcagcccct cccacaggc ggtgcaggtt      540 gggggtacgg ccagcctcca ctgcgacgtc agcggccgcc cgccgcctgc tgtgacctgg      600
gagaagcaga gtcaccagcg agagaacctg atcatgcgcc ctgatcagat gtatggcaac     660
gtggtggtca ccagcatcgg gcagctggtg ctctacaacg cgcggcccga agacgccggc     720
ctgtacacct gcaccgcgcg caacgctgct gggctgctgc gggctgactt cccactctct    780
gtggtccagc gagagccggc cagggacgca gccccagca tcccagcccc ggccgagtgc      840
ctgccggatg tgcaggcctg cacgggcccc acttccccac accttgtcct ctggcactac    900
gacccgcagc ggggcggctg catgaccttc ccggcccgtg gctgtgatgg ggcggcccgc    960
ggctttgaga cctacgaggc atgccagcag gcctgtgccc gcggcccggg cgacgcctgc   1020
gtgctgcctg ccgtgcaggg ccctgccgg gctgggagc cgcgctgggc ctacagcccg      1080
ctgctgcagc agtgccatcc cttcgtgtac ggtggctgca gggcaacgg caacaacttc     1140 cacagccgcg agagctgcga ggatgcctgc cccgtgccgc gcacaccgcc ctgccgcgcc    1200
tgccgcctcc ggagcaagct ggcgctgagc ctgtgccgca gcgacttcgc catcgtgggg   1260
cggctcacgg aggtgctgga ggagcccgag gccgccggcg gcatcgcccg cgtggcgctc   1320
gaggacgtgc tcaaggatga caagatgggc ctcaagttct ggggcaccaa gtacctggag    1380
gtgacgctga gtggcatgga ctgggcctgc ccctgcccca acatgacggc gggcgacggg   1440
ccgctggtca tcatgggtga ggtgcgcgat ggcgtggccg tgctggacgc cggcagctac   1500
gtccgcgccg ccagcgagaa gcgcgtcaag aagatcttgg agctgctgga gaagcaggcc   1560
tgcgagctgc tcaaccgctt ccaggac                                          1587
```

<210> SEQ ID NO 55
<211> LENGTH: 1728
<212> TYPE: DNA
<213> ORGANISM: Homo sapiens

<400> SEQUENCE: 55

```
atgtgggccc caaggtgtcg ccggttctgg tctcgctggg agcaggtggc agcgctgctg     60
ctgctgctgc tactgctcgg ggtgcccccg cgaagcctgg cgctgccgcc catccgctat    120
tcccacgccg gcatctgccc caacgacatg aatcccaacc tctgggtgga cgcacagagc   180
acctgcaggc gggagtgtga cacggaccag gagtgtgaga cctatgagaa gtgctgcccc   240
aacgtatgtg ggaccaagag ctgcgtggcg gcccgctaca tggacgtgaa agggaagaag   300
ggcccagtgg gcatgcccaa ggaggccaca tgtgaccact tcatgtgtct gcagcagggc   360
tctgagtgtg acatctggga tggccagccc gtgtgtaagt gcaaagaccg ctgtgagaag   420
gagcccagct ttacctgcgc ctcggacggc ctcacctact ataaccgctg ctacatggat   480
gccgaggcct gctccaaagg catcacactg gccgttgtaa cctgccgcta tcacttcacc   540
tggcccaaca ccagcccccc accacctgag accaccatgc ccccaccac agcctcccca   600 gagacccctg agctggacat ggcggcccct gcgctgctca caaccctgt gcaccagtcg   660 gtcaccatgg gtgagacagt gagcttcctc tgtgatgtgg tgggccggcc ccggcctgag    720
atcacctgga gaagcagtt ggaggatcgg gagaatgtgg tcatgcggcc caaccatgtg   780
cgtggcaacg tggtggtcac caacattgcc cagctgtca tctataacgc ccagctgcag   840
gatgctggga tctacacctg cacggcccgg aacgtggctg gggtcctgag ggctgatttc   900
```

```
ccgctgtcgg tggtcagggg tcatcaggct gcagccacct cagagagcag ccccaatggc    960
acggctttcc cggcggccga gtgcctgaag cccccagaca gtgaggactg tggcgaagag   1020
cagacccgct ggcacttcga tgcccaggcc aacaactgcc tgaccttcac cttcggccac   1080
tgccaccgta acctcaacca ctttgagacc tatgaggcct gcatgctggc ctgcatgagc   1140
gggccgctgg ccgcgtgcag cctgcccgcc ctgcaggggc cctgcaaagc ctacgcgcct   1200
cgctgggctt acaacagcca gacgggccag tgccagtcct ttgtctatgg tggctgcgag   1260
ggcaatggca caactttga gagccgtgag gcctgtgagg agtcgtgccc cttccccagg    1320
gggaaccagc gctgtcgggc ctgcaagcct cggcagaagc tcgttaccag cttctgtcgc   1380
agcgactttg tcatcctggg ccgagtctct gagctgaccg aggagcctga ctcgggccgc   1440
gccctggtga ctgtggatga ggtcctaaag gatgagaaaa tgggcctcaa gttcctgggc   1500
caggagccat ggaggtcac tctgcttcac gtggactggg catgcccctg ccccaacgtg    1560
accgtgagcg agatgccgct catcatcatg ggggaggtgg acggcggcat ggccatgctg   1620
cgccccgata gctttgtggg cgcatcgagt gcccgccggg tcaggaagct tcgtgaggtc   1680
atgcacaaga agacctgtga cgtcctcaag gagtttcttg gcttgcac               1728

<210> SEQ ID NO 56
<211> LENGTH: 1626
<212> TYPE: DNA
<213> ORGANISM: Homo sapiens

<400> SEQUENCE: 56
ctgccgccca tccgctattc ccacgccggc atctgcccca acgacatgaa tcccaacctc     60
tgggtggacg cacagagcac ctgcaggcgg gagtgtgaga cggaccagga gtgtgagacc    120
tatgagaagt gctgccccaa cgtatgtggg accaagagct gcgtggcggc ccgctacatg    180
gacgtgaaag ggaagaaggg cccagtgggc atgcccaagg aggccacatg tgaccacttc    240
atgtgtctgc agcagggctc tgagtgtgac atctgggatg ccagcccgt gtgtaagtgc     300 aaagaccgct gtgagaagga gcccagcttt acctgcgcct cggacggcct cacctactat    360
aaccgctgct acatggatgc cgaggcctgc tccaaaggca tcacactggc cgttgtaacc    420
tgccgctatc acttcacctg gcccaacacc agcccccac cacctgagac caccatgcac    480
cccaccacag cctccccaga gacccctgag ctggacatgg cggcccctgc gctgctcaac    540
aaccctgtgc accagtcggt caccatgggt gagacagtga gcttcctctg tgatgtggtg    600
ggccggcccc ggcctgagat cacctgggag aagcagttgg aggatcggga gaatgtggtc    660
atgcggccca accatgtgcg tggcaacgtg gtggtcacca acattgccca gctggtcatc    720
tataacgccc agctgcagga tgctgggatc tacacctgca cggcccggaa cgtggctggg    780
gtcctgaggg ctgatttccc gctgtcggtg gtcagggtc atcaggctgc agccacctca    840
gagagcagcc ccaatggcac ggcttttccg cggccgagt gcctgaagcc cccagacagt    900
gaggactgtg gcgaagagca gacccgctgg cacttcgatg cccaggccaa caactgcctg    960
accttcacct tcggccactg ccaccgtaac ctcaaccact ttgagaccta tgaggcctgc   1020
atgctggcct gcatgagcgg gccgctgcc gcgtgcagcc tgcccgccct gcaggggccc   1080
tgcaaagcct acgcgcctcg ctgggcttac aacagccaga cgggccagtg ccagtccttt   1140
gtctatggtg gctgcgaggg caatggcaac aactttgaga gccgtgaggc ctgtgaggag   1200
tcgtgcccct tccccagggg gaaccagcgc tgtcgggcct gcaagcctcg gcagaagctc   1260
```

-continued

```
gttaccagct tctgtcgcag cgactttgtc atcctgggcc gagtctctga gctgaccgag    1320
gagcctgact cgggccgcgc cctggtgact gtggatgagg tcctaaagga tgagaaaatg    1380
ggcctcaagt tcctgggcca ggagccattg gaggtcactc tgcttcacgt ggactgggca    1440 tgccctgcc ccaacgtgac cgtgagcgag atgccgctca tcatcatggg ggaggtggac    1500
ggcggcatgg ccatgctgcg ccccgatagc tttgtgggcg catcgagtgc ccgccgggtc    1560
aggaagcttc gtgaggtcat gcacaagaag acctgtgacg tcctcaagga gtttcttggc    1620
ttgcac                                                               1626
```

<210> SEQ ID NO 57
<211> LENGTH: 788
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Leu Pro Pro Ile Arg Tyr Ser His Ala Gly Ile Cys Pro Asn Asp Met
 1               5                  10                  15

Asn Pro Asn Leu Trp Val Asp Ala Gln Ser Thr Cys Arg Arg Glu Cys
             20                  25                  30

Glu Thr Asp Gln Glu Cys Glu Thr Tyr Glu Lys Cys Cys Pro Asn Val
         35                  40                  45

Cys Gly Thr Lys Ser Cys Val Ala Ala Arg Tyr Met Asp Val Lys Gly
     50                  55                  60

Lys Lys Gly Pro Val Gly Met Pro Lys Glu Ala Thr Cys Asp His Phe
 65                  70                  75                  80

Met Cys Leu Gln Gln Gly Ser Glu Cys Asp Ile Trp Asp Gly Gln Pro
                 85                  90                  95

Val Cys Lys Cys Lys Asp Arg Cys Glu Lys Glu Pro Ser Phe Thr Cys
            100                 105                 110

Ala Ser Asp Gly Leu Thr Tyr Tyr Asn Arg Cys Tyr Met Asp Ala Glu
        115                 120                 125

Ala Cys Ser Lys Gly Ile Thr Leu Ala Val Val Thr Cys Arg Tyr His
    130                 135                 140

Phe Thr Trp Pro Asn Thr Ser Pro Pro Pro Glu Thr Thr Met His
145                 150                 155                 160

Pro Thr Thr Ala Ser Pro Glu Thr Pro Glu Leu Asp Met Ala Ala Pro
                165                 170                 175

Ala Leu Leu Asn Asn Pro Val His Gln Ser Val Thr Met Gly Glu Thr
            180                 185                 190

Val Ser Phe Leu Cys Asp Val Val Gly Arg Pro Arg Pro Glu Ile Thr
        195                 200                 205

Trp Glu Lys Gln Leu Glu Asp Arg Glu Asn Val Met Arg Pro Asn
    210                 215                 220

His Val Arg Gly Asn Val Val Thr Asn Ile Ala Gln Leu Val Ile
225                 230                 235                 240

Tyr Asn Ala Gln Leu Gln Asp Ala Gly Ile Tyr Thr Cys Thr Ala Arg
                245                 250                 255

Asn Val Ala Gly Val Leu Arg Ala Asp Phe Pro Leu Ser Val Val Arg
            260                 265                 270

Gly His Gln Ala Ala Ala Thr Ser Glu Ser Ser Pro Asn Gly Thr Ala
        275                 280                 285
```

```
Phe Pro Ala Ala Glu Cys Leu Lys Pro Pro Asp Ser Glu Asp Cys Gly
290                 295                 300

Glu Glu Gln Thr Arg Trp His Phe Asp Ala Gln Ala Asn Asn Cys Leu
305                 310                 315                 320

Thr Phe Thr Phe Gly His Cys His Arg Asn Leu Asn His Phe Glu Thr
                325                 330                 335

Tyr Glu Ala Cys Met Leu Ala Cys Met Ser Gly Pro Leu Ala Ala Cys
                340                 345                 350

Ser Leu Pro Ala Leu Gln Gly Pro Cys Lys Ala Tyr Ala Pro Arg Trp
            355                 360                 365

Ala Tyr Asn Ser Gln Thr Gly Gln Cys Gln Ser Phe Val Tyr Gly Gly
370                 375                 380

Cys Glu Gly Asn Gly Asn Asn Phe Glu Ser Arg Glu Ala Cys Glu Glu
385                 390                 395                 400

Ser Cys Pro Phe Pro Arg Gly Asn Gln Arg Cys Arg Ala Cys Lys Pro
                405                 410                 415

Arg Gln Lys Leu Val Thr Ser Phe Cys Arg Ser Asp Phe Val Ile Leu
                420                 425                 430

Gly Arg Val Ser Glu Leu Thr Glu Glu Pro Asp Ser Gly Arg Ala Leu
            435                 440                 445

Val Thr Val Asp Glu Val Leu Lys Asp Glu Lys Met Gly Leu Lys Phe
450                 455                 460

Leu Gly Gln Glu Pro Leu Glu Val Thr Leu Leu His Val Asp Trp Ala
465                 470                 475                 480

Cys Pro Cys Pro Asn Val Thr Val Ser Glu Met Pro Leu Ile Ile Met
                485                 490                 495

Gly Glu Val Asp Gly Gly Met Ala Met Leu Arg Pro Asp Ser Phe Val
                500                 505                 510

Gly Ala Ser Ser Ala Arg Arg Val Arg Lys Leu Arg Glu Val Met His
            515                 520                 525

Lys Lys Thr Cys Asp Val Leu Lys Glu Phe Leu Gly Leu His Thr Gly
            530                 535                 540

Gly Gly Gly Ser Gly Gly Gly Ser Gly Gly Gly Ser Gly Gly Ser Gly
545                 550                 555                 560

Gly Gly Ser Thr His Thr Cys Pro Pro Cys Pro Ala Pro Glu Leu Leu
                565                 570                 575

Gly Gly Pro Ser Val Phe Leu Phe Pro Pro Lys Pro Lys Asp Thr Leu
            580                 585                 590

Met Ile Ser Arg Thr Pro Glu Val Thr Cys Val Val Val Asp Val Ser
            595                 600                 605

His Glu Asp Pro Glu Val Lys Phe Asn Trp Tyr Val Asp Gly Val Glu
610                 615                 620

Val His Asn Ala Lys Thr Lys Pro Arg Glu Glu Gln Tyr Asn Ser Thr
625                 630                 635                 640

Tyr Arg Val Val Ser Val Leu Thr Val Leu His Gln Asp Trp Leu Asn
                645                 650                 655

Gly Lys Glu Tyr Lys Cys Lys Val Ser Asn Lys Ala Leu Pro Ala Pro
            660                 665                 670

Ile Glu Lys Thr Ile Ser Lys Ala Lys Gly Gln Pro Arg Glu Pro Gln
                675                 680                 685

Val Tyr Thr Leu Pro Pro Ser Arg Lys Glu Met Thr Lys Asn Gln Val
690                 695                 700

Ser Leu Thr Cys Leu Val Lys Gly Phe Tyr Pro Ser Asp Ile Ala Val
```

```
                705                 710                 715                 720
Glu Trp Glu Ser Asn Gly Gln Pro Gly Asn Asn Tyr Lys Thr Thr Pro
                    725                 730                 735

Pro Val Leu Lys Ser Asp Gly Ser Phe Phe Leu Tyr Ser Lys Leu Thr
                740                 745                 750

Val Asp Lys Ser Arg Trp Gln Gln Gly Asn Val Phe Ser Cys Ser Val
                755                 760                 765

Met His Glu Ala Leu His Asn His Tyr Thr Gln Lys Ser Leu Ser Leu
    770                 775                 780

Ser Pro Gly Lys
785

<210> SEQ ID NO 58
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ser Asn Thr Lys Val Asp Lys Arg Val Thr Gly Gly Gly Thr His Thr
1               5                   10                  15

Cys Pro Pro Cys Pro Ala Pro Glu Leu Leu Gly Gly Pro Ser Val Phe
                20                  25                  30

Leu Phe Pro Pro Lys Pro Lys Asp Thr Leu Met Ile Ser Arg Thr Pro
            35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
                100                 105                 110

Lys Val Ser Asn Lys Ala Leu Pro Ala Pro Ile Glu Lys Thr Ile Ser
            115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Asp Thr Thr Pro Val Leu Asp Ser Asp
            180                 185                 190

Gly Ser Phe Phe Leu Tyr Ser Asp Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235

<210> SEQ ID NO 59
<211> LENGTH: 2364
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 59

```
ctgccgccca tccgctattc ccacgccggc atctgcccca cgacatgaa tcccaacctc      60
tgggtggacg cacagagcac ctgcaggcgg gagtgtgaga cggaccagga gtgtgagacc     120
tatgagaagt gctgcccccaa cgtatgtggg accaagagct gcgtggcggc ccgctacatg    180
gacgtgaaag ggaagaaggg cccagtgggc atgcccaagg aggccacatg tgaccacttc     240
atgtgtctgc agcagggctc tgagtgtgac atctgggatg ccagcccgt gtgtaagtgc      300
aaagaccgct gtgagaagga gcccagcttt acctgcgcct cggacggcct cacctactat    360
aaccgctgct acatggatgc cgaggcctgc tccaaaggca tcacactggc cgttgtaacc    420
tgccgctatc acttcacctg gcccaacacc agcccccac cacctgagac caccatgcac     480
cccaccacag cctccccaga ccccctgag ctggacatgg cggcccctgc gctgctcaac     540
aaccctgtgc accagtcggt caccatgggt gagacagtga gcttcctctg tgatgtggtg    600
ggccggcccc ggcctgagat cacctgggag aagcagttgg aggatcggga gaatgtggtc    660
atgcggccca accatgtgcg tggcaacgtg gtggtcacca acattgccca gctggtcatc   720
tataacgccc agctgcagga tgctgggatc tacacctgca cggcccggaa cgtggctggg   780
gtcctgaggg ctgatttccc gctgtcggtg gtcaggggtc atcaggctgc agccacctca   840
gagagcagcc ccaatggcac ggcttttccg gcggccgagt gcctgaagcc ccccgacagt   900
gaggactgtg gcgaagagca gacccgctgg cacttcgatg cccaggccaa caactgcctg   960
accttcacct tcggccactg ccaccgtaac ctcaaccact ttgagaccta tgaggcctgc  1020
atgctggcct gcatgagcgg gccgctggcc gcgtgcagcc tgcccgccct gcaggggccc  1080
tgcaaagcct acgcgcctcg ctgggcttac aacagccaga cgggccagtg ccagtccttt  1140
gtctatggtg gctgcgaggg caatggcaac aactttgaga gccgtgaggc ctgtgaggag  1200
tcgtgccccct tccccagggg gaaccagcgc tgtcgggcct gcaagcctcg gcagaagctc  1260
gttaccagct tctgtcgcag cgactttgtc atcctgggcc gagtctctga gctgaccgag  1320
gagcctgact cgggccgcgc cctggtgact gtggatgagg tcctaaagga tgagaaaatg  1380
ggcctcaagt tcctgggcca ggagccattg gaggtcactc tgcttcacgt ggactgggca  1440
tgcccctgcc ccaacgtgac cgtgagcgag atgccgctca tcatcatggg ggaggtggac  1500
ggcggcatgg ccatgctgcg cccgatagc tttgtgggcg catcgagtgc ccgccgggtc  1560
aggaagcttc gtgaggtcat gcacaagaag acctgtgacg tcctcaagga gtttcttggc  1620
ttgcacaccg gtggtggagg ttctggaggt ggaggaagtg gtggaggtgg ttctggaggt  1680
ggtgaagta ctcacacatg cccaccgtgc ccagcacctg aactcctggg gggaccgtca  1740
gtcttcctct tccccccaaa acccaaggac accctcatga tctcccggac ccctgaggtc  1800
acatgcgtgt ggtggacgt gagccacgaa gaccctgagg tcaagttcaa ctggtacgtg  1860
gacggcgtgg aggtgcataa tgccaagaca aagccgcggg aggagcagta caacagcacg  1920
taccgtgtgg tcagcgtcct caccgtcctg caccaggact ggctgaatgg caaggagtac  1980
aagtgcaagg tctccaacaa agccctccca gcccccatcg agaaaaccat ctccaaagcc  2040
aaagggcagc cccgagaacc acaggtgtac accctgcccc catcccggaa ggagatgacc  2100
aagaaccagg tcagcctgac ctgcctggtc aaaggcttct atcccagcga catcgccgtg  2160
gagtgggaga gcaatgggca gccggagaac aactacaaga ccacgcctcc cgtgctgaag  2220
```

```
tccgacggct ccttcttcct ctatagcaag ctcaccgtgg acaagagcag gtggcagcag    2280
gggaacgtct tctcatgctc cgtgatgcat gaggctctgc acaaccacta cacgcagaag    2340
agcctctccc tgtctccggg taaa                                           2364
```

<210> SEQ ID NO 60
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
agcaacacca aggtggacaa gagagttacc ggtggtggaa ctcacacatg cccaccgtgc      60
ccagcacctg aactcctggg gggaccgtca gtcttcctct tccccccaaa acccaaggac     120
accctcatga tctcccggac ccctgaggtc acatgcgtgg tggtggacgt gagccacgaa     180
gaccctgagg tcaagttcaa ctggtacgtg gacggcgtgg aggtgcataa tgccaagaca     240
aagccgcggg aggagcagta caacagcacg taccgtgtgg tcagcgtcct caccgtcctg     300
caccaggact ggctgaatgg caaggagtac aagtgcaagg tctccaacaa agccctccca     360
gcccccatcg agaaaaccat ctccaaagcc aagggcagc cccgagaacc acaggtgtac      420
accctgcccc catcccggga ggagatgacc aagaaccagg tcagcctgac ctgcctggtc     480
aaaggcttct atcccagcga catcgccgtg gagtgggaga gcaatgggca gccggagaac     540
aactacgaca ccacgcctcc cgtgctggac tccgacggct ccttcttcct ctatagcgac     600
ctcaccgtgg acaagagcag gtggcagcag gggaacgtct tctcatgctc cgtgatgcat     660
gaggctctgc acaaccacta cacgcagaag agcctctccc tgtctccggg taaa           714
```

<210> SEQ ID NO 61
<211> LENGTH: 29
<212> TYPE: PRT
<213> ORGANISM: Homo sapiens

<400> SEQUENCE: 61

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala
            20                  25

<210> SEQ ID NO 62
<211> LENGTH: 26
<212> TYPE: PRT
<213> ORGANISM: Homo sapiens

<400> SEQUENCE: 62

Met Arg Pro Gly Ala Pro Gly Pro Leu Trp Pro Leu Pro Trp Gly Ala
1               5                   10                  15

Leu Ala Trp Ala Val Gly Phe Val Ser Ser
            20                  25

<210> SEQ ID NO 63
<211> LENGTH: 19
<212> TYPE: PRT
<213> ORGANISM: Homo sapiens

<400> SEQUENCE: 63

Met Pro Ala Leu Arg Pro Leu Leu Pro Leu Leu Leu Leu Leu Arg Leu
1               5                   10                  15

Thr Ser Gly

<210> SEQ ID NO 64
<211> LENGTH: 34
<212> TYPE: PRT
<213> ORGANISM: Homo sapiens

<400> SEQUENCE: 64

Met Trp Ala Pro Arg Cys Arg Arg Phe Trp Ser Arg Trp Glu Gln Val
1               5                   10                  15

Ala Ala Leu Leu Leu Leu Leu Leu Leu Gly Val Pro Pro Arg Ser
            20                  25                  30

Leu Ala

<210> SEQ ID NO 65
<211> LENGTH: 22
<212> TYPE: PRT
<213> ORGANISM: Unknown
<220> FEATURE:
<223> OTHER INFORMATION: Description of Unknown:
      Tissue plasminogen activator peptide

<400> SEQUENCE: 65

Met Asp Ala Met Lys Arg Gly Leu Cys Cys Val Leu Leu Leu Cys Gly
1               5                   10                  15

Ala Val Phe Val Ser Pro
            20

<210> SEQ ID NO 66
<211> LENGTH: 21
<212> TYPE: PRT
<213> ORGANISM: Apis mellifera

<400> SEQUENCE: 66

Met Lys Phe Leu Val Asn Val Ala Leu Val Phe Met Val Val Tyr Ile
1               5                   10                  15

Ser Tyr Ile Tyr Ala
            20

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71
<211> LENGTH: 771
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

```
Leu Pro Pro Ile Arg Tyr Ser His Ala Gly Ile Cys Pro Asn Asp Met
1               5                   10                  15

Asn Pro Asn Leu Trp Val Asp Ala Gln Ser Thr Cys Arg Arg Glu Cys
            20                  25                  30

Glu Thr Asp Gln Glu Cys Glu Thr Tyr Glu Lys Cys Cys Pro Asn Val
        35                  40                  45

Cys Gly Thr Lys Ser Cys Val Ala Ala Arg Tyr Met Asp Val Lys Gly
    50                  55                  60

Lys Lys Gly Pro Val Gly Met Pro Lys Glu Ala Thr Cys Asp His Phe
65                  70                  75                  80

Met Cys Leu Gln Gln Gly Ser Glu Cys Asp Ile Trp Asp Gly Gln Pro
                85                  90                  95

Val Cys Lys Cys Lys Asp Arg Cys Glu Lys Glu Pro Ser Phe Thr Cys
            100                 105                 110

Ala Ser Asp Gly Leu Thr Tyr Tyr Asn Arg Cys Tyr Met Asp Ala Glu
        115                 120                 125

Ala Cys Ser Lys Gly Ile Thr Leu Ala Val Val Thr Cys Arg Tyr His
    130                 135                 140

Phe Thr Trp Pro Asn Thr Ser Pro Pro Pro Glu Thr Thr Met His
145                 150                 155                 160

Pro Thr Thr Ala Ser Pro Glu Thr Pro Glu Leu Asp Met Ala Ala Pro
                165                 170                 175

Ala Leu Leu Asn Asn Pro Val His Gln Ser Val Thr Met Gly Glu Thr
            180                 185                 190

Val Ser Phe Leu Cys Asp Val Gly Arg Pro Arg Pro Glu Ile Thr
        195                 200                 205

Trp Glu Lys Gln Leu Glu Asp Arg Glu Asn Val Val Met Arg Pro Asn
    210                 215                 220

His Val Arg Gly Asn Val Val Val Thr Asn Ile Ala Gln Leu Val Ile
225                 230                 235                 240

Tyr Asn Ala Gln Leu Gln Asp Ala Gly Ile Tyr Thr Cys Thr Ala Arg
                245                 250                 255

Asn Val Ala Gly Val Leu Arg Ala Asp Phe Pro Leu Ser Val Val Arg
            260                 265                 270

Gly His Gln Ala Ala Thr Ser Glu Ser Ser Pro Asn Gly Thr Ala
        275                 280                 285

Phe Pro Ala Ala Glu Cys Leu Lys Pro Pro Asp Ser Glu Asp Cys Gly
    290                 295                 300

Glu Glu Gln Thr Arg Trp His Phe Asp Ala Gln Ala Asn Asn Cys Leu
305                 310                 315                 320

Thr Phe Thr Phe Gly His Cys His Arg Asn Leu Asn His Phe Glu Thr
                325                 330                 335

Tyr Glu Ala Cys Met Leu Ala Cys Met Ser Gly Pro Leu Ala Ala Cys
            340                 345                 350

Ser Leu Pro Ala Leu Gln Gly Pro Cys Lys Ala Tyr Ala Pro Arg Trp
        355                 360                 365
```

-continued

```
Ala Tyr Asn Ser Gln Thr Gly Gln Cys Gln Ser Phe Val Tyr Gly Gly
370                 375                 380

Cys Glu Gly Asn Gly Asn Asn Phe Glu Ser Arg Glu Ala Cys Glu Glu
385                 390                 395                 400

Ser Cys Pro Phe Pro Arg Gly Asn Gln Arg Cys Arg Ala Cys Lys Pro
            405                 410                 415

Arg Gln Lys Leu Val Thr Ser Phe Cys Arg Ser Asp Phe Val Ile Leu
            420                 425                 430

Gly Arg Val Ser Glu Leu Thr Glu Pro Asp Ser Gly Arg Ala Leu
            435                 440                 445

Val Thr Val Asp Glu Val Leu Lys Asp Glu Lys Met Gly Leu Lys Phe
450                 455                 460

Leu Gly Gln Glu Pro Leu Glu Val Thr Leu Leu His Val Asp Trp Ala
465                 470                 475                 480

Cys Pro Cys Pro Asn Val Thr Val Ser Glu Met Pro Leu Ile Ile Met
                485                 490                 495

Gly Glu Val Asp Gly Gly Met Ala Met Leu Arg Pro Asp Ser Phe Val
            500                 505                 510

Gly Ala Ser Ser Ala Arg Arg Val Arg Lys Leu Arg Glu Val Met His
            515                 520                 525

Lys Lys Thr Cys Asp Val Leu Lys Glu Phe Leu Gly Leu His Thr Gly
530                 535                 540

Gly Gly Thr His Thr Cys Pro Pro Cys Pro Ala Pro Glu Leu Leu Gly
545                 550                 555                 560

Gly Pro Ser Val Phe Leu Phe Pro Pro Lys Pro Lys Asp Thr Leu Met
            565                 570                 575

Ile Ser Arg Thr Pro Glu Val Thr Cys Val Val Val Asp Val Ser His
            580                 585                 590

Glu Asp Pro Glu Val Lys Phe Asn Trp Tyr Val Asp Gly Val Glu Val
            595                 600                 605

His Asn Ala Lys Thr Lys Pro Arg Glu Glu Gln Tyr Asn Ser Thr Tyr
    610                 615                 620

Arg Val Val Ser Val Leu Thr Val Leu His Gln Asp Trp Leu Asn Gly
625                 630                 635                 640

Lys Glu Tyr Lys Cys Lys Val Ser Asn Lys Ala Leu Pro Ala Pro Ile
                645                 650                 655

Glu Lys Thr Ile Ser Lys Ala Lys Gly Gln Pro Arg Glu Pro Gln Val
            660                 665                 670

Tyr Thr Leu Pro Pro Cys Arg Glu Glu Met Thr Lys Asn Gln Val Ser
            675                 680                 685

Leu Trp Cys Leu Val Lys Gly Phe Tyr Pro Ser Asp Ile Ala Val Glu
690                 695                 700

Trp Glu Ser Asn Gly Gln Pro Glu Asn Asn Tyr Lys Thr Thr Pro Pro
705                 710                 715                 720

Val Leu Asp Ser Asp Gly Ser Phe Phe Leu Tyr Ser Lys Leu Thr Val
            725                 730                 735

Asp Lys Ser Arg Trp Gln Gln Gly Asn Val Phe Ser Cys Ser Val Met
            740                 745                 750

His Glu Ala Leu His Asn His Tyr Thr Gln Lys Ser Leu Ser Leu Ser
            755                 760                 765

Pro Gly Lys
770
```

```
<210> SEQ ID NO 72
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ser Asn Thr Lys Val Asp Lys Arg Val Thr Gly Gly Thr His Thr
1               5                   10                  15

Cys Pro Pro Cys Pro Ala Pro Glu Leu Leu Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Cys Thr Leu Pro Pro
    130                 135                 140

Ser Arg Glu Glu Met Thr Lys Asn Gln Val Ser Leu Ser Cys Ala Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Val Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 73

Thr Gly Gly Gly
1

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 74
```

```
Thr Gly Gly Gly Gly
1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 75

Ser Gly Gly Gly Gly
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 76

Gly Gly Gly Gly Ser
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 77

His His His His His His
1               5
```